United States Patent
Mayevsky

(10) Patent No.: US 11,832,975 B2
(45) Date of Patent: Dec. 5, 2023

(54) TISSUE METABOLIC SCORE FOR PATIENT MONITORING

(71) Applicant: MDX Life Sciences, Inc., Newton, MA (US)

(72) Inventor: Avraham Mayevsky, Ramat Gan (IL)

(73) Assignee: MDX Life Sciences, Inc., Newton, MA (US)

( * ) Notice: Subject to any disclaimer, the term of this patent is extended or adjusted under 35 U.S.C. 154(b) by 318 days.

(21) Appl. No.: 17/102,479

(22) Filed: Nov. 24, 2020

(65) Prior Publication Data

US 2021/0153816 A1    May 27, 2021

Related U.S. Application Data

(60) Provisional application No. 62/941,584, filed on Nov. 27, 2019.

(51) Int. Cl.
*A61B 5/1455* (2006.01)
*A61B 5/00* (2006.01)
(Continued)

(52) U.S. Cl.
CPC .......... *A61B 5/746* (2013.01); *A61B 5/02055* (2013.01); *A61B 5/0261* (2013.01);
(Continued)

(58) Field of Classification Search
CPC ..... A61B 5/1455; A61B 5/746; A61B 5/0261; A61B 5/6852; A61B 5/7275
See application file for complete search history.

(56) References Cited

U.S. PATENT DOCUMENTS 5,685,313 A    11/1997    Mayevsky
5,916,171 A    6/1999    Mayevsky
(Continued)

OTHER PUBLICATIONS

John Allen, Photoplethysmography and its application in clinical physiological measurement, Physiol. Meas. 28 (2007) R1-R39, doi:10.1088/0967-3334/28/3/R01.
(Continued)

*Primary Examiner* — Marjan Fardanesh
(74) *Attorney, Agent, or Firm* — Potomac Law Group, PLLC; David E. Boundy

(57) ABSTRACT

In an organ of interest in a patient is emplaced a set of sensors designed to monitor parameters of the organ of interest, including at least nicotinamide adenine dinucleotide level and at least one parameter from among the group consisting of tissue blood flow, blood hemoglobin, and tissue reflectance. Substantially continuously, a vitality index of the organ of interest is computed based at least in part on the parameters monitored by the sensors at the organ of interest. Another point of the patient is monitored continuously for a systemic reference, NADH level and at least two parameters from among the group consisting of blood flow ($BF_S$), blood hemoglobin, and tissue reflectance. Substantially continuously, a systemic vitality index is computed from the measured systemic parameters. The vitality index of the organ of interest and systemic vitality index are monitored for a divergence in the temporal trend. Based on the detection of the divergence, an alarm is raised to a physician to warn the physician of a change in the patient's condition.

19 Claims, 35 Drawing Sheets

NAD - nicotinamide adenine dinucleotide

(51) Int. Cl.
    A61B 5/145      (2006.01)
    A61B 5/0205     (2006.01)
    A61B 5/026      (2006.01)
    A61B 5/024      (2006.01)
    A61B 5/08       (2006.01)
    A61B 5/0215     (2006.01)
(52) U.S. Cl.
    CPC ...... *A61B 5/14539* (2013.01); *A61B 5/14546* (2013.01); *A61B 5/14551* (2013.01); *A61B 5/6852* (2013.01); *A61B 5/7275* (2013.01); *A61B 5/0215* (2013.01); *A61B 5/02416* (2013.01); *A61B 5/0816* (2013.01); *A61B 2560/0228* (2013.01)

(56) References Cited

U.S. PATENT DOCUMENTS

| | | | |
|---|---|---|---|
| 7,130,672 | B2 | 10/2006 | Pewsner |
| 7,313,424 | B2 | 12/2007 | Mayevsky |
| 8,666,468 | B1 | 3/2014 | Al-Ali |
| 9,066,666 | B2 | 6/2015 | Kiani |
| 2004/0054270 | A1 | 3/2004 | Pewzner |
| 2005/0043606 | A1 | 2/2005 | Pewzner |
| 2005/0234315 | A1 | 10/2005 | Mayevsky |
| 2006/0161055 | A1 | 7/2006 | Pewzner |
| 2007/0179366 | A1 | 8/2007 | Pewzner |

OTHER PUBLICATIONS

Jesse F. Ashruf, Hajo A. Bruining, and Can Ince, New insights into the pathophysiology of cardiogenic shock—the role of the microcirculation, Current Opinion in Critical Care 19(5):381-386 (Oct. 2013).
Mary Kay Bader, Linda R. Littlejohns, Karen Mar., Brain Tissue Oxygen Monitoring in Severe Brain Injury, II: Implications for Critical Care Teams and Case Study, Critical Care Nurse, 23:29-44 (2003).
Thomas S. Blacker, et al., Separating NADH and NADPH fluorescence in live cells and tissues using FLIM, Nature Communications, 5:3936 (May 29, 2014) DOI: 10.1038/ncomms4936.
Thomas S. Blacker & Michael R. Duchen, Investigating mitochondrial redox state using NADH and NADPH autofluorescence, Free Radical Biology & Medicine 100: 53-65 (Nov. 2016); doi: 10.1016/j.freeradbiomed.2016.08.010.
Eliezer L. Bose, Marilyn Hravnak, and Michael R. Pinsky, The Interface between Monitoring and Physiology at the bedside, Critical Care Clinics 31(1):1-24 (Jan. 2015).
Eliezer Bose, Leslie Hoffman, Marilyn Hravnak, Monitoring Cardiorespiratory Instability: Current Approaches and Implications for Nursing Practice, Intensive Crit Care Nursing, 34: 73-80 (Jun. 2016).
California Institute for Regenerative Medicine, Engineering Strategies, Opportunities, and Challenges for Tissue Repair and Regeneration: CIRM Workshop Summary and. Recommendations—San Francisco, CA; (Jan. 12-13, 2012).
Luigi Camporota and Richard Beale, Pitfalls in haemodynamic monitoring based on the arterial pressure waveform, Critical Care 14:124 (Mar. 5, 2010).
A. Gil Cano, M.I. Monge Garcia, F. Baigorri Gonzalez, Evidence on the utility of hemodynamic monitorization in the critical patient, Med Intensiva 36 (9), 650-655 (Sep. 7, 2012).
Britton Chance, N. Oshino, T. Sugano, Avraham Mayevsky, Basic principles of tissue oxygen determination from mitochondrial signals. Adv. Exp. Med. Biol., 37A: 277-292 (1973).
Britton Chance, Clyde Barlow, John Haselgrove, Yuzo Nakase, Bjørn Quistorff, Franz Matschinsky; Avraham Mayevsky, A Microheterogeneities of redox states of perfused and intact organs. In Srere P (ed) Microenvironments and Metabolic Compartmentation. Academic Press, New York, pp. 131-148 (1978).
Assaf Deutsch, Eliyahu Pevzner, Alex Jaronkin, Avraham Mayevsky, Real time evaluation of tissue vitality by monitoring of microcirculatory blood flow, $HbO_2$ and mitochondrial NADH redox state. Optical Fibers and Sensors for Medical Applications IV, Proc. SPIE, vol. 5317, Ed. I. Gannot, pp. 116-127 (2004).
Abele Donati, Roberta Domizi, Elisa Damiani, Erica Adrario, Paolo Pelaia, and Can Ince, From Macrohemodynamic to the Microcirculation, Critical Care Research and Practice, vol. 2013, Article ID 892710, 8 pages.
Abele Donati, Dick Tibboel, Can Ince, Towards integrative physiological monitoring of the critically ill: from cardiovascular to microcirculatory and cellular function monitoring at the bedside, Critical Care 17(Suppl 1):S5 (Mar. 2012).
Alex Dyson, S. Cone, M. Singer and G. L. Ackland, Microvascular and macrovascular flow are uncoupled in early polymicrobial sepsis, British Journal of Anaesthesia 108 (6):973-78 (Mar. 2012).
Nasirul J. Ekbal, Alex Dyson, Claire Black, Mervyn Singer, Monitoring Tissue Perfusion, Oxygenation, and Metabolism in Critically Ill Patients, Chest 143(6):1799-1808 (Jun. 2013).
Mohamed Elgendi, Yongbo Liang, and Rabab Ward, Toward Generating More Diagnostic Features from Photoplethysmogram Waveforms, Diseases 6, 20 (2018); doi:10.3390/diseases6010020.
Mohamed Elgendi, Richard Fletcher, Yongbo Liang, Newton Howard, Nigel H. Lovell, Derek Abbott, Kenneth Lim, and Rabab Ward, The use of photoplethysmography for assessing hypertension, Digital Medicine 2:60 (2019); doi 10.1038/s41746-019-0136-7.
Mathieu Guillame-Bert, Artur Dubrawski, Donghan Wang, Marilyn Hravnak, Gilles Clermont, Michael R Pinsky, Learning temporal rules to forecast instability in continuously monitored patients, Journal of the American Medical Informatics Association, 24(1):47-53 (Jun. 2016).
Mark Helfand, Vivian Christensen, Johanna Anderson, Technology Assessment: EarlySense for Monitoring Vital Signs in Hospitalized Patients, Department of Veterans Affairs, Health Services Research & Development Service, Evidence-based Synthesis Program (May 2016).
Andre L. Holder, Michael R. Pinsky, Applied physiology at the bedside to drive resuscitation algorithms, J Cardiothorac Vasc Anesth. Dec. 2014 ; 28(6):1642-1659 (Dec. 2014).
Marilyn Hravnak, Leslie Edwards, Amy Clontz, Cynthia Valenta, Michael A. De Vita, Michael R. Pinsky, Defining the Incidence of Cardiorespiratory Instability in Patients in Step-down Units Using an Electronic Integrated Monitoring System, Archives of Internal Medicine vol. 168 No. 12 pp. 1300-1308 (Jun. 23, 2008).
Marilyn Hravnak, Michael A. De Vita, Amy Clontz, Leslie Edwards, Cynthia Valenta, Michael R. Pinsky, Cardiorespiratory instability before and after implementing an integrated monitoring system, Critical Care Medicine, 39(1):65-72 (Jan. 2011).
Marilyn Hravnak, Lujie Chen, Artur Dubrawski, Eliezer Bose, Gilles Clermont, Michael R. Pinsky, Real alerts and artifact classification in archived multi-signal vital sign monitoring data: implications for mining big data, J Clin Monit Comput 30(6):875-888 (Oct. 2015).
Can Ince, The Great Fluid Debate: When Will Physiology Prevail?, Anesthesiology 119(2):248-249 (Aug. 2013).
Andrew A. Kanner; Zvi Harry Rappaport; Tamar Manor; Avraham Mayevsky, Multiparametric monitoring of rat brain retraction, Proc. SPIE (International Society for Optical Engineering) 4623, Functional Monitoring and Drug-Tissue Interaction, (Jun. 5, 2002); doi: 10.1117/12.491257.
Ari Kraut, Efrat Barbiro-Michaely, Avraham Mayevsky, Differential effect of norepinephrine on brain and other less vital organs detected by a Multisite Multiparametric Monitoring system. *Medical Science Monitor* 10: BR215-220 (2004).
Hofit Kutai-Asis, Efrat Barbiro-Michaely, Assaf Deutsch, Avraham Mayevsky, Fiber optic based multiparametric spectroscopy in vivo: Toward a new quantitative tissue vitality index. *SPIE Proc.* 6083: 10-1-10-10 (2006).
Miram Mandelbaum, Efrat Barbiro-Michaely, Michael Tolmasov, Avraham Mayevsky, Effects of severe hemorrhage on in vivo brain and small intestine mitochondrial NADH and microcirculatory blood flow, Proceedings of the 6th International Conference on

(56) References Cited

OTHER PUBLICATIONS

Photonics and Imaging in Biology and Medicine (PIBM 2007) Wuhan, P R China (Nov. 4-6, 2007), *J. of Innovative Optical Health Sciences* 1: 177-183 (2008).
Avraham Mayevsky, Brain energy metabolism of the conscious rat exposed to various physiological and pathological situations. Brain Res. 113: 327-338 (1976).
Avraham Mayevsky, Ischemia in the Brain: The Effects of Carotid Artery Ligation and Decapitation on the Energy State of the Awake and Anesthetized Rat. Brain Res 140 (2), 217-230. (Jan. 27, 1978).
Avraham Mayevsky, Britton Chance, Intracellular oxidation reduction state measured in situ by a multichannel fiber-optic-surface fluorometer. Science 217: 537-540 (1982).
Avraham Mayevsky, N. Zarchin, C.M. Friedli, Factors affecting the oxygen balance in the awake cerebral cortex exposed to spreading depression. Brain Res. vol. 236 pp. 93-105 (Mar. 18, 1982).
Mayevsky A, Zarchin N, Kaplan H, Haveri J, Haselgrove J, Chance B Brain metabolic responses to ischemia in the Mongolian gerbil: in vivo and freeze trapped redox state scanning. Brain Res 276:95-107 (1983).
Avraham Mayevsky, E.S. Flamm, William Pennie, Britton Chance, A fiber optic based multiprobe system for intraoperative monitoring of brain functions. SPIE (International Society for Optical Engineering) Proc vol. 1431, pp. 303-313 (May 1991) doi: 10.1117/12.44201.
Avraham Mayevsky, Aurbach Doron A, Tamar Manor, Sigal Meilin, N. Zarchin, G.E. Ouaknine, Cortical spreading depression recorded from the human brain using a multiparametric monitoring system. Brain Res 740 No. 1-2, pp. 268-274 (Nov. 18, 1996).
Avraham Mayevsky, Sigal Meilin, Tamar Manor, Eugene Ornstein, N. Zarchin, Judith Sonn (1998) Multiparametric monitoring of brain oxygen balance under experimental and clinical conditions. Neurol Res 20 Suppl. 1 pp. S76-S80 (1998).
Avraham Mayevsky, Tamar Manor, Sigal Meilin, Aurbach Doron, G.E. Ouaknine, Real-time multiparametric monitoring of the injured human cerebral cortex—a new approach. Acta Neurochirurgica Supplements, vol. 71. Springer, Vienna, vol. 71 pp. 78-81 (1998).
Avraham Mayevsky, Aurbach Doron, Sigal Meilin, Tamar Manor, Eugene Ornstein, G.E. Ouaknine (1999) Brain viability and function analyzer: multiparametric real-time monitoring in neurosurgical patients, Neuromonitoring in Brain Injury, Acta Neurochir Suppl (Wien) vol. 75 pp. 63-66 (1999).
Avraham Mayevsky, Gennady G. Rogatsky, Judith Sonn, New multiparametric monitoring approach for real-time evaluation of drug tissue interaction in vivo. Drug Dev. Res., 50: 457-470 (Jul.-Aug. 2000).
Avraham Mayevsky, Ari Kraut, Tamar Manor, Judith Sonn, Yehuda Zurovsky, Optical monitoring of tissue viability using reflected spectroscopy in vivo, Proceedings of SPIE—The International Society for Optical Engineering, vol. 4241, pp. 409-417 (May 2001).
Mayevsky A, Manor T, Meilin S, Razon N, Ouaknine GE, Multiparametric monitoring of tissue vitality in clinical situations. Proc SPIE 4255:33-39 (2001).
Mayevsky, A., Manor, T., Pevzner, E., Deutsch, A., Etziony, R. and Dekel, N. Real time optical monitoring of tissue vitality in vivo. Ed. I. Gannot. *Proc. SPIE* 4616: 30-39 (2002).
Avraham Mayevsky, Eugene Ornstein, Sigal Meilin, N. Razon, G.E. Ouaknine, The evaluation of brain CBF and mitochondrial function by a fiber optic tissue spectroscope in neurosurgical patients. Acta neurochirurgica. Supplement 81(81):367-371 (Feb. 2002).
Avraham Mayevsky, Judith Sonn, Merav Luger-Hamer, Richard Nakache, Real-Time assessment of organ vitality during the transplantation procedure, Transplantation Reviews, vol. 17, issue 2, pp. 96-116 (Apr. 2003).
Mayevsky, A., Manor, T., Pevzner, E., Deutsch, A., Etziony, R., Dekel, N. and Jaronkin, A. Tissue spectroscope: a novel in vivo approach to real time monitoring of tissue vitality. *J. Biomed. Optics* 9: 1028-1045 (2004).
Mayevsky, A., Barbiro-Michaeli, E., Kutai-Asis, H., Deutsch, A. and Jaronkin, A. Brain physiological state evaluated by real time multiparametric tissue spectroscopy in vivo. In: Optical Biopsy V, Proc. SPIE, vol. 5326, Eds. R.R. Alfano and A. Katz, pp. 98-105 (2004).
Mayevsky, A., Deutsch, A., Dekel, N., Pevzner, L. and Jaronkin, A. New biomedical device for in vivo multiparametric evaluation of tissue vitality in critical care medicine. In: Advanced Biomedical and Clinical Diagnosis System III, *Proc. SPIE*, vol. 5692, Eds. T. Vo-Dinh, W.S. Grundfest, D.A. Benaron and G.E. Cohn, pp. 60-70 (2005).
Mayevsky, A., Blum, Y., Dekel, N., Deutsch, A., Halfon, R., Kremer, S., Pewzner, E., Sherman, E. and Barnea, O. The CritiView—A new fiber optic based optical device for the assessment of tissue vitality. *SPIE Proc.* 6083: 02-1-02-10 (2006).
Mayevsky, A. and Rogatsky, G.G. Mitochondrial function in vivo evaluated by NADH fluorescence: From animal models to human studies. *Am. J. Physiol. Cell Physiol.* 292: C615-C640 (2007).
Avraham Mayevsky, Nava Dekel, Levi Oren, Assaf Deutsch, Eliyahu Pewzner, Mitochondrial dysfunction: Bench-to-bedside optical monitoring of tissue vitality. SPIE Proc. 6853, Biomedical Optical Spectroscopy, 1B1-1B11 (2008).
Avraham Mayevsky, Raphael Walden, Eliyahu Pewzner, Assaf Deutsch, Eitan Heldenberg, Jacob Lavee, Salis Tager, Erez Kachel, Ehud Raanani, Sergey Preisman, Violete Glauber, Eran Segal, Mitochondrial function and tissue vitality: bench-to-bedside real-time optical monitoring system. Journal of Biomedical Optics 16(6):067004 (Jun. 2011).
Avraham Mayevsky, Mitochondrial Function In Vivo Evaluated by NADH Fluorescence, Springer International Publishing Switzerland pp. 1-276 (2015).
Avraham Mayevsky, Michael Tolmasov and Mira Mandelbaum, Perioperative Cardiovascular Evaluation of Patients Oxygen Balance and Tissue Metabolic Score (TMS), American Journal of Cardiovascular Thoracic Surgery 3(3):1-17. Doi: 10.15226/2573-864X/3/3/00145 (2018).
Avraham Mayevsky, Elhanan Meirovithz, Amir Livnat, Michael Tolmasov, Hofit Kutai-Asis, Mira Mandelbaum, Urethral Tissue Metabolic Score (TMS) as a Surrogate Marker of Brain Oxygen Balance in Stroke, ARDS and Critical Care Patients Exposed to Oxygen Therapy, EC Emergency Medicine and Critical Care SI.01 (2020): 05-40.
Sigal Meilin, Nili Zarchin, Avaraham Mayevsky, and Shlomo Shapira, Multiparametric responses to Cortical Spreading Depression under Nitric Oxide Synthesis Inhibition, in Weissman B.A., Allon N., Shapira S. (eds) Biochemical, Pharmacological, and Clinical Aspects of Nitric Oxide. Springer, Boston, MA, 195-204 (1995).
Sigal Meilin, A. Mendelman, Judith Sonn, T. Manor, Nili Zarchin, Avraham Mayevsky, Metabolic and hemodynamic oscillations monitored optically in the brain exposed to various pathological states. Adv Exp Med Biol 471:141-146; in Eke and Delpy eds., Oxygen Transport to Tissue XXI pp. 141-146 (1999).
Elhanan Meirovithz, Judith Sonn, Avraham Mayevsky. Effect of hyperbaric oxygenation on brain hemodynamics, hemoglobin oxygenation and mitochondrial NADH, Brain Research Reviews 54(2):294-304 (2007).
Anushirvan Minokadeh, Michael R. Pinsky, Postoperative hemodynamic instability and monitoring, Current Opinion in Critical Care 22(4):393-400 (Aug. 2016).
John M. Murkin, Sandra J. Adams, Ricahrd J. Novick, Mackenzie Quantz, Daniel Bainbridge, Ivan Iglesias, Andrew Cleland, Betsy Schaefer, Beverly Irwin, Stephanie Fox, Monitoring brain oxygen saturation during coronary bypass surgery: a randomized, prospective study. Anesthesia & Analgesia, vol. 104, issue 1, pp. 51-58 (Jan. 2007).
Llewellyn C. Padayachy, Anthony A. Figaji, Malcolm Ross Bullock, Intracranial pressure monitoring for traumatic brain injury in the modern era, Childs Nerv Syst. 26(4):441-452 (Apr. 2010).
Péter Palágyi, József Kaszaki, Andrea Rostás, Dániel Érces, Márton Németh, Mihály Boros, Zsolt Molnár, Monitoring Microcirculatory

(56) References Cited

OTHER PUBLICATIONS

Blood Flow with a New Sublingual Tonometer in a Porcine Model of Hemorrhagic Shock, BioMed Research International, vol. 2015, Article ID 847152 (Oct. 2015).

Pierre Pandin, Marie Renard, Alessia Bianchini, Philippe Desjardin, Luc Van Obbergh, Monitoring Brain and Spinal Cord Metabolism and Function, Open Journal of Anesthesiology 4, 131-152 (Jun. 2014).

Michael R. Pinsky, Gilles Clermont, Marilyn Hravnak, Predicting cardiorespiratory instability, Critical Care 20:70 (Mar. 2016).

Michael R Pinsky, The cost of shock resuscitation treatment decisions, Lancet Respiratory Medicine 4(1):769-770 (Oct. 2016).

Richard Pullinger, Sarah Wilson, Rob Way, Mauro Santos, David Wong, David Clifton, Jacqueline Birks, Lionel Tarassenko, Implementing an electronic observation and early warning score chart in the emergency department: a feasibility study, European Journal of Emergency Medicine 24(6):e11-e16 (Feb. 2016).

Kim Z.Rokamp, Niels H.Secher, Jonas Eiberg, Lars Lønn, Henning B.Nielsen, $O_2$ supplementation to secure the near-nfrared spectroscopy determined brain and muscle oxygenation in vascular surgical patients: a presentation of 100 cases, Frontiers in Physiology vol. 5 article No. 66 (Feb. 2014).

Zoltán Rózsavölgyi, Domokos Boda, Andrea Hajnal, Krisztina Boda, and Attila Somfay, A Newly Developed Sublingual Tonometric Method for the Evaluation of Tissue Perfusion and Its Validation In Vitro and in Healthy Persons In Vivo and the Results of the Measurements in COPD Patients, Critical Care Research and Practice, vol. 2014, Article ID 534130 (Dec. 2014).

Patrick Schober, Lothar Schwarte, From system to organ to cell: oxygenation and perfusion measurement in anesthesia and critical care, J Clin Monit Comput, 26(4):255-265 (Mar. 2012).

Mervyn Singer, The role of mitochondrial dysfunction in sepsis-induced multi-organ failure, Virulence 5(1):66-72 (Jan. 2014).

Judith Sonn, Avraham Mayevsky, Responses to cortical spreading depression under oxygen deficiency. The Open Neurol. J. 6: 6-17 (2012).

Eric M. Suess, Michael R. Pinsky, Hemodynamic Monitoring for the Evaluation and Treatment of Shock: What Is the Current State of the Art? Seminars in Respiratory and Critical Care Medicine 36(6):1-9 (2015).

Michel E. van Genderen, Sebastiaan A. Bartels, Alexandre Lima, Rick Bezemer, Can Ince, Jan Bakker, Jasper van Bommel, Peripheral Perfusion Index as an Early Predictor for Central Hypovolemia in Awake Healthy Volunteers, Anashtesia And Analgesia 116(2):351-356 (Feb. 2013).

Larisa Vatov, Ziv Kizner, Eytan Ruppin, Sigal Meilin, Tamar Manor, Avraham Mayevsky, Modeling brain energy metabolism and function: A multiparametric monitoring approach. Bulletin of Mathematical Biology 68:275-291 (2006).

Jean-Louis Vincent, Paolo Pelosi, Rupert Pearse, Didier Payen, Azriel Perel, Andreas Hoeft, Stefano Romagnoli, V Marco Ranieri, Carole Ichai, Patrice Forget, Giorgio Della Rocca, Andrew Rhodes, Perioperative cardiovascular monitoring of high-risk patients: a consensus of 12, Critical Care 19:224 (2015).

Eyal Zimlichman, Martine Szyper-Kravitz, Zvika Shinar, Tal Klap, Shiraz Levkovich, Avraham Unterman, Ronen Rozenblum, Jeffrey M. Rothschild, Howard Amital, Yehuda Shoenfeld, Early Recognition of Acutely Deteriorating Patients in Non-Intensive Care Units: Assessment of an Innovative Monitoring Technology, J. Hospital Medicine 7(8):628-633 (Oct. 2012).

NAD - nicotinamide adenine dinucleotide

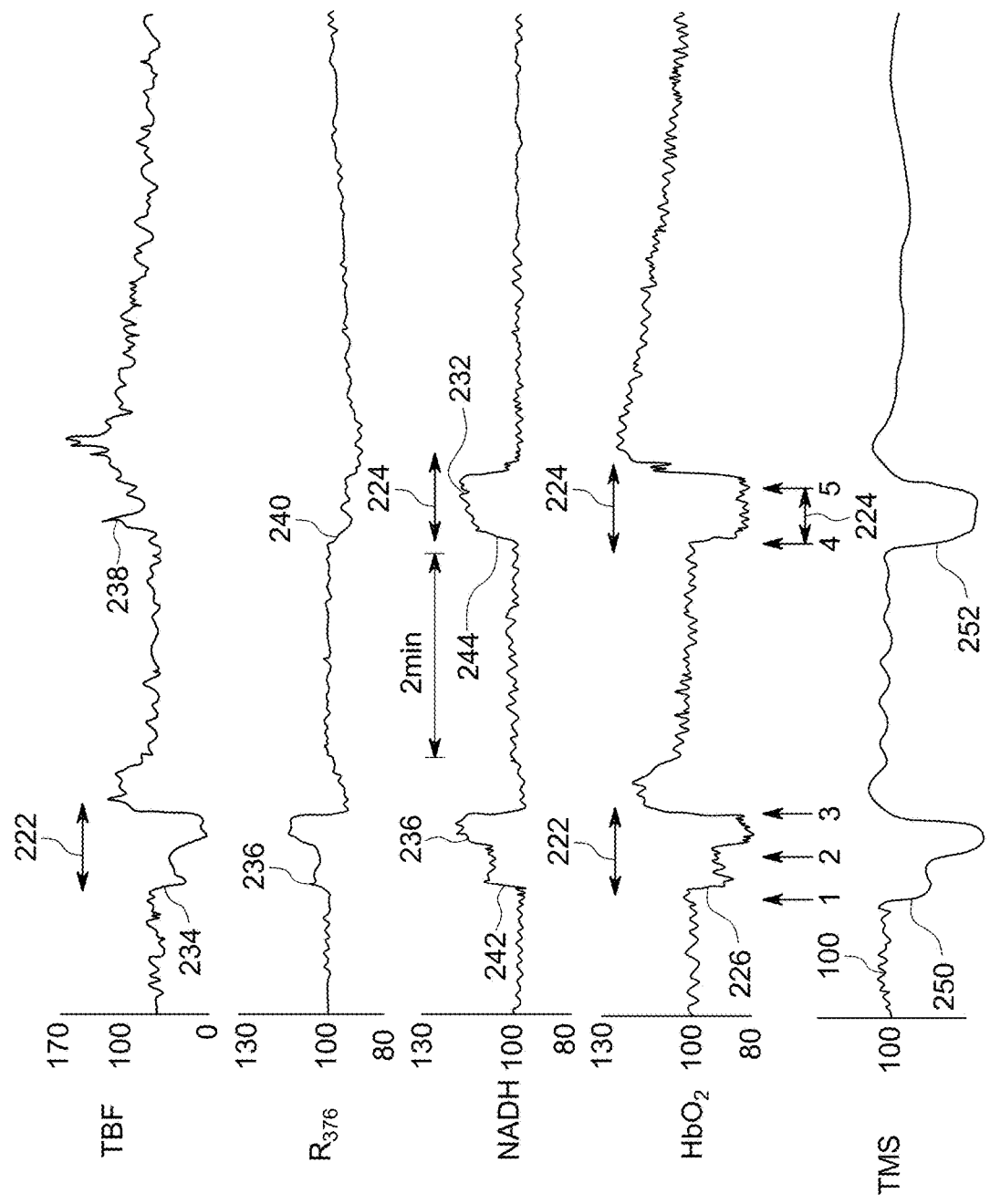

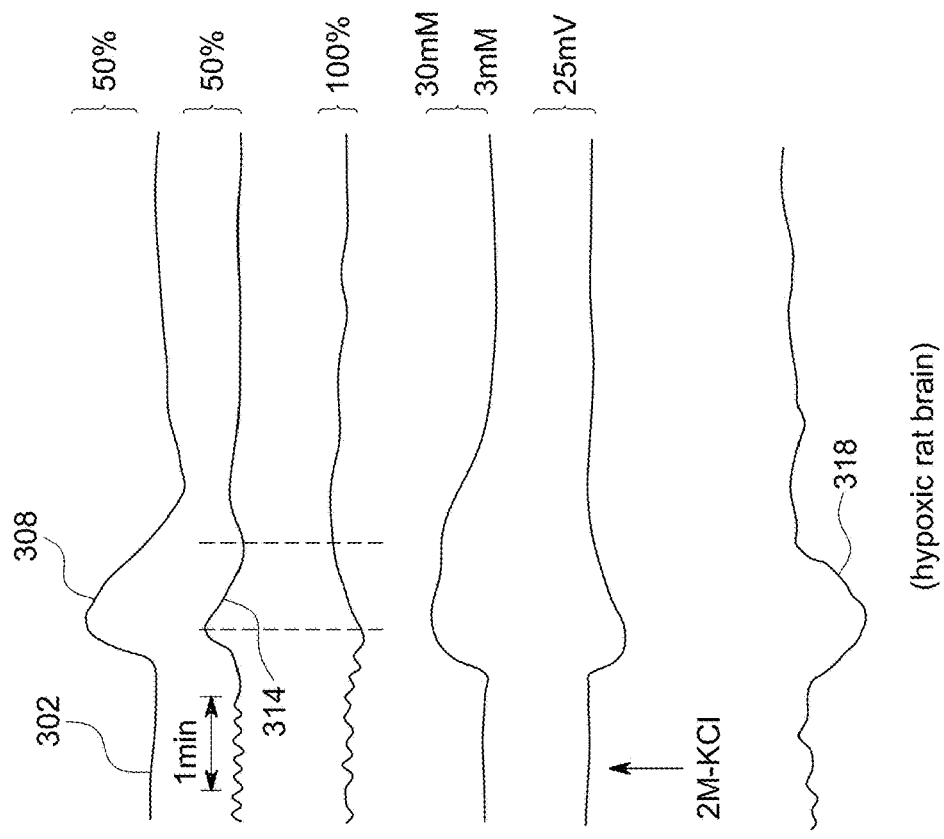
FIG. 4B (hypoxic rat brain)
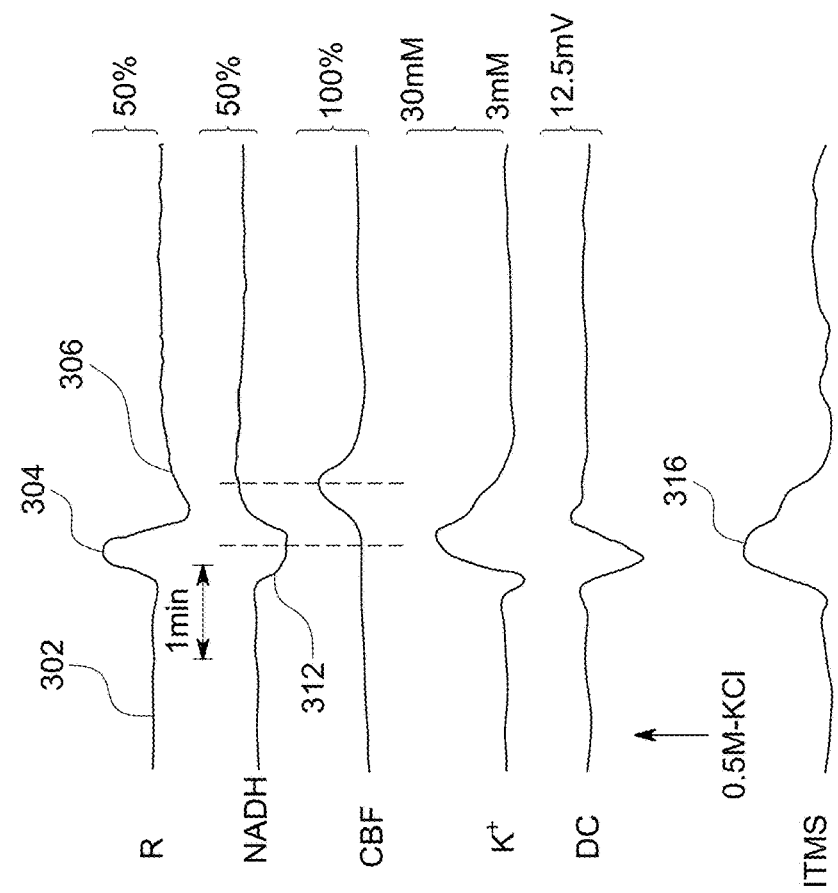
FIG. 4A (normoxic rat brain)

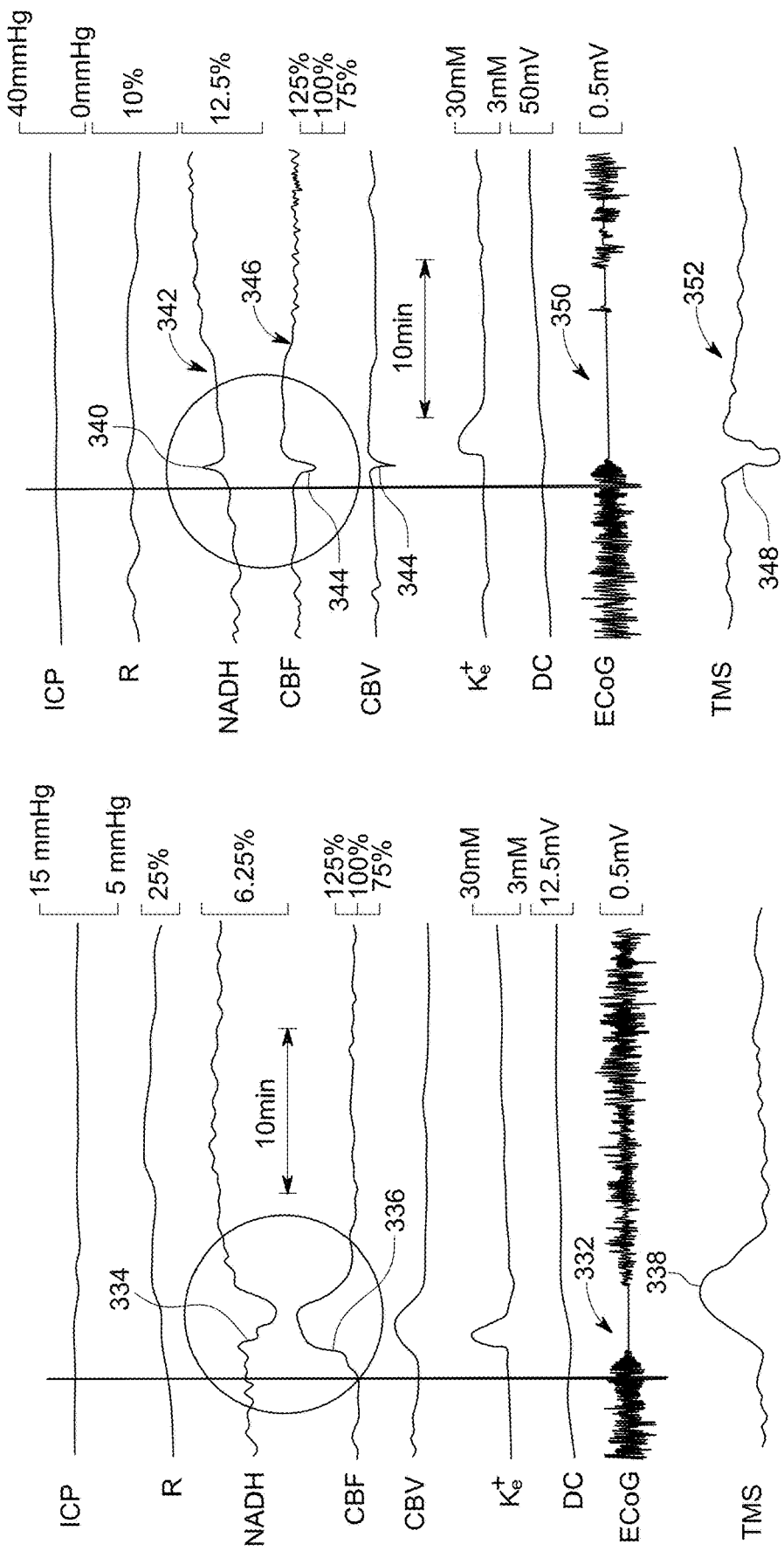

TISSUE METABOLIC SCORE FOR PATIENT MONITORING

This application is a nonprovisional of U.S. Provisional App. Ser. No. 62/941,584, filed Nov. 27, 2019, incorporated by reference.

BACKGROUND

This application relates to monitoring of medical patients.

Mitochondria are the intracellular organelles that convert nutrients and oxygen to adenosine triphosphate (ATP), which is, in turn, the primary fuel consumed by all cells in the body. Mitochondria receive oxygen from the blood. In tissues of a body, oxygen (energy) supply is in a balance with demand/consumption. The supply of oxygen or energy in a tissue is dependent upon microcirculatory blood flow (TBF), blood volume (TBV), and the level of oxygen bound to the hemoglobin ($HbO_2$) in the small blood vessels of the microcirculation. The level of oxygenated hemoglobin in the microcirculation is affected by two factors, namely, oxygen supply in the microcirculatory blood flow and volume, less oxygen consumption by the mitochondria. This oxygen balance between supply and consumption takes place in all organs and tissues in the body. This supply side is typically similar in all tissues of the body. The demand for oxygen is affected by the specific activities taking place in each organ of the body and may be evaluated by monitoring of different parameters in each organ. Energy demand varies between the different tissues and may include ionic homeostasis, signal conduction, muscle contraction, glandular secretion, gastrointestinal tract activities and kidney function.

Referring to FIGS. 1A and 1B, one of the molecules in the mitochondria that participates in the consumption of oxygen is NAD (nicotinamide adenine dinucleotide) 20. NAD occurs in two redox forms, NAD+ (the oxidized form) 22 and NADH (the reduced form) 24. In the intra-cell metabolic cycle, NAD+ is reduced to NADH and oxidized back to NAD+ in a cycle 7A that maintains a healthy ratio of the two forms. The nicotinamide group 28 is the "functional" part of both molecules i.e., the portion of the molecule where oxidation and reduction take place. FIG. 1B shows the transition between oxidized and reduced NADH.

Referring to FIGS. 1C and 1D, mitochondrial NADH redox state serves as an indicator for tissue energy or oxygen balance and the state of mitochondrial oxidative phosphorylation enzymes. NADH absorbs light at 320-380 nm (ultraviolet) and fluoresces 42 at 420-480 nm range (blue). The oxidized form $NAD^+$ does not absorb 44 light in the 320 nm-380 nm range (and thus does not fluoresce). FIG. 1C shows the absorption Spectra of NAD+ and NADH. FIG. 1D shows the excitation and emission spectra of NADH. Mitochondrial function in vivo may be evaluated by measuring the NADH redox state. That NADH redox state of the mitochondria may be monitored by measuring the UV absorbance 40 or blue fluorescence 42 of NADH, which in turn allows an inference of the balance between oxygen consumption and supply. Oxygen levels in the mitochondria are very sensitive to changes in the supply of oxygen via the vascular system.

Tissue reflectance is a measure of the amount of light reflected back from the tissue at the excitation wavelength range of NADH (320-380 nm). This parameter is related to the blood volume in the tissue. More blood will absorb more light so the reflectance will decrease and vice versa.

Oxygen delivery to a tissue of the body is the product of blood flow volume times the quantity of available oxygen carried by that blood flow.

Microcirculation is the circulation of the blood in the smallest blood vessels, present in the vasculature embedded within organ tissues. The microcirculation is composed of terminal arterioles, capillaries, and venules that drain capillary blood, and the diffusion of oxygen across capillary walls and cell membranes. This contrasts with macrocirculation, which is the circulation of blood to and from the organs via the larger arteries and veins.

Referring to FIG. 1E, the microcirculation is composed of terminal arterioles, capillaries, and venules that drain capillary blood. The arterioles are 10-100 μm in diameter, well innervated, and surrounded by smooth muscle cells. The capillaries are about 5-8 μm in diameter, not innervated, and have no smooth muscle. The venules have a diameter of 10-200 μm, and have little smooth muscle. In addition to these blood vessels, the microcirculation also includes lymphatic capillaries and collecting ducts. The main functions of the microcirculation are the delivery of oxygen and nutrients and the removal of carbon dioxide. It also serves to regulate blood flow and tissue perfusion thereby affecting blood pressure and responses to inflammation which can include edema (swelling).

Most vessels of the microcirculation are lined by flattened cells of the endothelium and many of them are surrounded by contractile cells called pericytes. The endothelium provides a smooth surface for the flow of blood and regulates the movement of water and dissolved materials in the interstitial plasma between the blood and the tissues. The endothelium also produces molecules that discourage the blood from clotting unless there is a leak. Pericyte cells can contract and decrease the size of the arterioles and thereby regulate blood flow and blood pressure.

SUMMARY

In general, in a first aspect, the invention features a method. In an organ of interest in a patient is emplaced a set of sensors designed to monitor parameters of the organ of interest, including at least nicotinamide adenine dinucleotide ($NADH_I$) level and at least one parameter from among the group consisting of tissue blood flow ($BF_I$), blood hemoglobin ($HbO_{2I}$), and tissue reflectance ($TR_I$). Substantially continuously, a vitality index of the organ of interest is computed based at least in part on the parameters monitored by the sensors at the organ of interest. Another point of the patient is monitored continuously for a systemic reference, NADH ($NADH_S$) level and at least two parameters from among the group consisting of blood flow ($BF_S$), blood hemoglobin ($HbO_{2S}$), and tissue reflectance ($TR_S$). Substantially continuously, a systemic vitality index is computed from the measured systemic parameters. The vitality index of the organ of interest and systemic vitality index are monitored for a divergence in the temporal trend. Based on the detection of the divergence, an alarm is raised to a physician to warn the physician of a change in the patient's condition.

In general, in a second aspect, the invention features a method. A plurality of vitality properties of a tissue of a patient are monitored substantially continuously, at least one of which is NADH fluorescence or absorption. A function of the parameters is computed to combine the numerical values of the tissue vitality properties substantially in real time, to compute a tissue metabolic score value. The monitoring of the tissue vitality properties and computing of tissue metabolic score continues over time. If the tissue metabolic score value improves, based on that score improvement, medical treatment of the patient is maintained. If the tissue metabolic score value deteriorates, based on that deterioration, treatment of the patient is changed in order to drive the tissue vitality parameters in a desired direction.

In general, in a third aspect, the invention features a method. A plurality of vitality properties of two or more tissues of a patient are measured continuously. For each of the two tissues, at least one of the parameters is NADH fluorescence or absorption. The numerical values of the vitality properties are combined to compute respective tissue metabolic score values of the two or more tissues. The monitoring of the tissue vitality properties and computing of tissue metabolic score continues over time. If the metabolic scores move relative to each other, then based on that movement, medical treatment of one of the tissues is adjusted. If the metabolic scores move together in a favorable direction, then, based on that movement, treatment of the patient is maintained. If the metabolic scores move together in an unfavorable direction, then, based on that movement, treatment of the patient is changed to drive the metabolic scores back to a more favorable value.

In general, in a fourth aspect, the invention features a urethral catheter. A tube encloses a fluid passage from a patient's urinary bladder to a collection receptacle outside the patient's body. On the wall of the tube are arrayed sensors designed to detect at least the following parameters: TBF tissue blood flow, NADH (nicotinamide adenine dinucleotide) fluorescence, Tissue Reflectance and $HbO_2$ blood hemoglobin, and sensors designed to detect at least two vital signs, drawn from the group consisting of pulse rate, temperature, respiration rate, blood pressure, blood level of CO2, and blood pH.

In general, in a fifth aspect, the invention features a method. A plurality of metabolic properties is continuously measured at the wall of a patient's urethra, including at least TBF tissue blood flow, NADH (nicotinamide adenine dinucleotide) fluorescence, and $HbO_2$ blood hemoglobin. At least two vital signs are continuously measured, drawn from the group consisting of pulse rate, temperature, respiration rate, blood pressure, blood level of CO2, and blood pH. The numerical values of the metabolic properties and vital signs are continuously combined to compute a total body metabolic score. The total body metabolic score is reported to a clinician.

Specific embodiments of the invention may include any of following features, singly or in any combination. The organ of interest may be a point in the gastrointestinal tract. The organ of interest may be the urethra. The sensors may be mounted in the wall of a urethral catheter. The organ of interest may be an organ in transit to or recently transplanted into the patient. The sensors for the organ of interest may include at least three of four of sensors from the group consisting of nicotinamide adenine dinucleotide ($NADH_I$), tissue blood flow ($BF_I$), blood hemoglobin ($HbO_{2I}$), and tissue reflectance ($TR_I$). The sensors for the organ of interest may include four sensors, respectively for nicotinamide adenine dinucleotide ($NADH_I$), tissue blood flow ($BF_I$), blood hemoglobin ($HbO_{2I}$), and tissue reflectance ($TR_I$). At least two vital signs may be monitored, drawn from the group consisting of pulse rate, temperature, respiration rate, blood pressure, blood level of $CO_2$, and blood pH. A vital signs index may be computed based on the monitored vital signs. Monitoring may analyzed for a divergence in the temporal trend of the vitality index of the tissue of interest from the vital signs index. Based on the detection of the divergence, an alarm may be raised to a physician to warn the physician of a change in the patient's condition. The systemic parameters may be monitored at a highly-conserved tissue. The reference tissue may be the brain, heart, muscle, or skin. The computation of vitality index may be designed to center on a recognizable reference value, such as 1.0 or 100. The computation of vitality index may be normalized to a steady-state observation of normal function for the specific patient. The computation of vitality index may be normalized across data obtained from many patients' sensors and accumulated in a database. The computation of divergence of the organ of interest vitality index from the systemic vitality index may be calibrated across data obtained from many patients' sensors and accumulated in a database.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION OF THE DRAWINGS

FIGS. 3A, 3B, 3C, 3D, 3E, 4A, 4B, 4C, 4D, 4E, 5A, 5B, 6A, 6B, 7A, 7B, 8D, and 9E are plots of various monitoring parameters and the tissue metabolic score against time.

DESCRIPTION

Figure 2A:
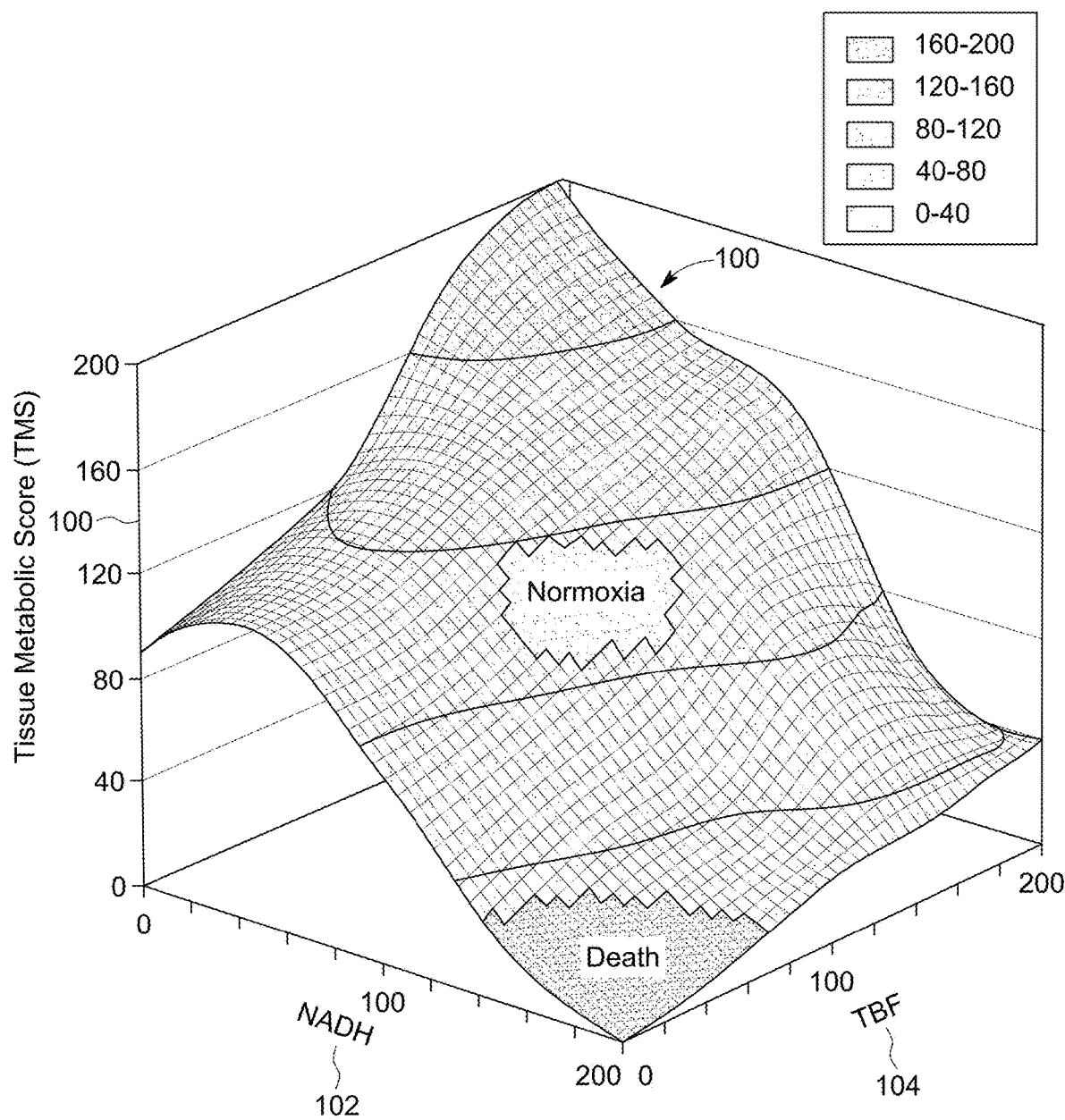
FIG. 2A is a three-dimensional plot of tissue metabolic score against NADH levels and tissue blood flow.
Figure 2B:
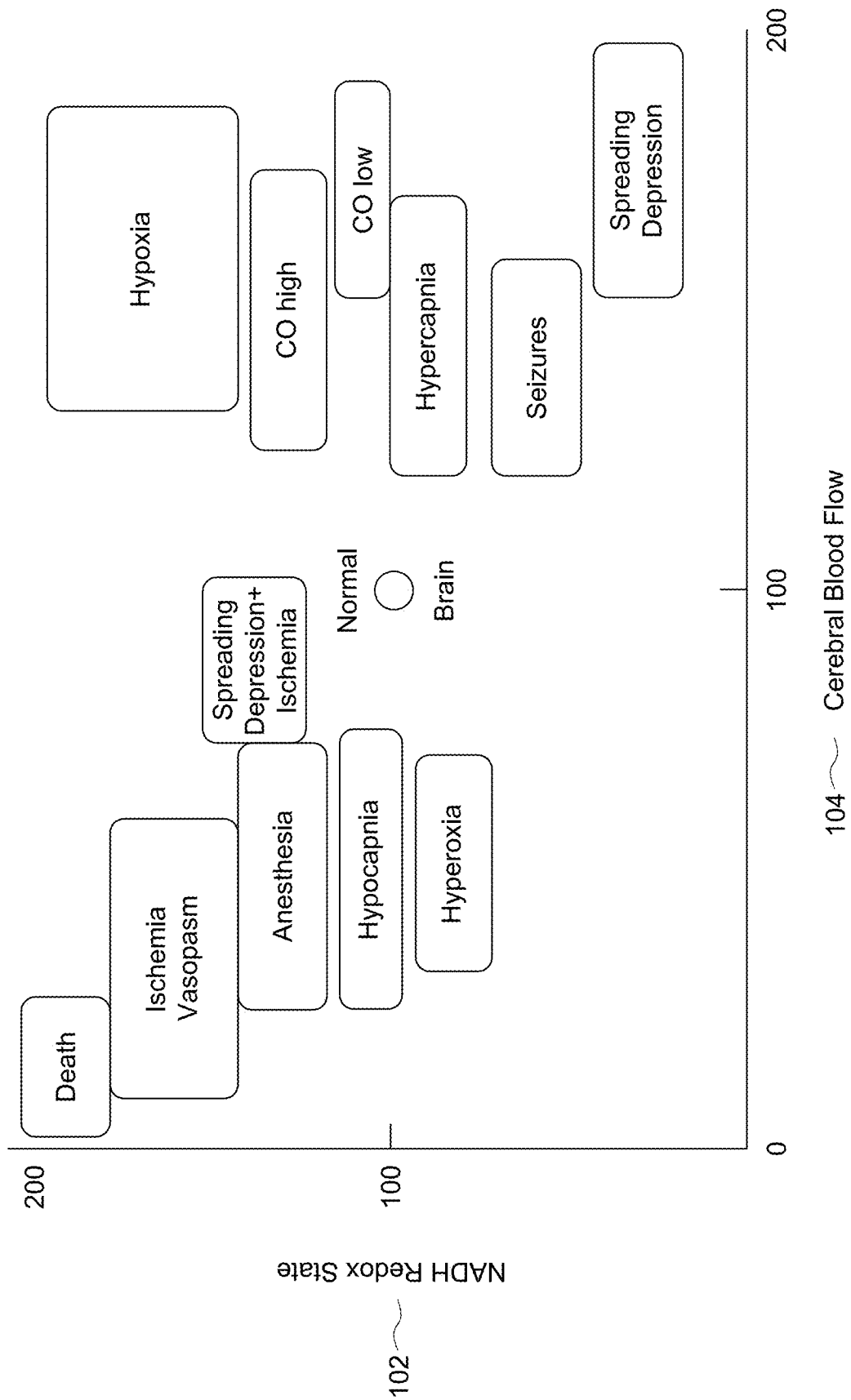
FIG. 2B is a plot of physiological condition against NADH redox state and cerebral blood flow.

The Description is organized as follows.
I. Overview
II. Use of the Tissue Metabolic Score
   II.A. Correlation of the tissue metabolic score to physiological state
   II.B. Example 1: blood loss in a patient
   II.C. Example 2: heart bypass operation
   II.D. Example 3: Tissue Oxygen Balance Analyzer
   II.E. Example 4: cortical spreading depression in a rat brain II.F. Example 5: cortical spreading depression in a human neurosurgical comatose patient
II.G. Example 6: a head injury patient
II.H. Example 7: Tissue metabolic score and monitoring the brain
II.I. Example 8: monitoring of two organs
II.J. Example 9: another example of monitoring two organs
II.K. Example 10: monitoring urethral and brain metabolic scores together with systemic parameters
II.L. Example 11: neurosurgical patients
II.M. Example 12: diagnosing brain death for an organ donor
II.N. Example 13: organ transplants in the recipient
II.O. Example 14: trauma patient with blood loss
II.P. Example 15: Regenerative medicine
II.Q. Example 16: monitor and probes
III. Urethral monitoring and total body metabolic score
III.A. A multiparameter catheter
III.B. A multi-parameter Total Body Metabolic Score
IV. Example 17: big data implementations
V. Computer implementation I. Overview Referring to FIG. 2A, normal supply of oxygen to the mitochondria is dependent upon the adequate microcirculatory blood flow and volume as well as the high saturation of the hemoglobin molecules in the red blood cells in the capillaries. A patient may be monitored for mitochondrial function and macrocirculation. This may be especially important in a setting where oxygen delivery to the body may fall to a level that may harm the patient. Mitochondrial function may be measured as NADH redox state 102. Tissue vitality may be measured by other parameters, for example, tissue blood flow (TBF) 104, tissue blood volume (TBV), and tissue oxyhemoglobin ($HbO_2$). Numerical values from this monitoring may be combined to compute a numerical score for a tissue metabolic score (TMS) 100. The tissue metabolic score may guide a clinician's treatment decisions. Analysis of various traces using an appropriate algorithm may provide an index that tells the clinician how to diagnose the tissue metabolic score 100 of the tissue and treat it accordingly.

The clinician may monitor the tissue metabolic score 100 over time. As the tissue metabolic score varies either higher or lower, the clinician may vary treatment to drive the tissue metabolic score back to its normative center.

The clinician may monitor two tissues and observe the relationship of the tissue metabolic score 100 for the two tissues to ascertain tissue health. For example, it may be desirable to monitor the tissue metabolic score of the urethra ($TMS_U$) simultaneously with the tissue metabolic score of a tissue under treatment, for example, the brain ($TMS_B$), or a transplanted organ. Monitoring two tissues simultaneously may assist the clinician in early identification of changes in oxygen delivery or consumption in the tissue under treatment or in the entire body. Because the urethra is one of the organs for which the body shuts down blood flow earliest, urethral monitoring of NADH redox state 102, blood flow 104, and oxygenation are especially sensitive measures of overall circulation, and thus is especially useful as one of two tissues to be monitored simultaneously. The mechanism of blood flow redistribution will cause a vasoconstriction in less vital organs, e.g., the urethra, to maximize blood flow and oxygen supply to the brain and heart. There are many cases that the $TMS_U$ may change before changes are visible in the vital signs of the entire body.

Figure 1A:
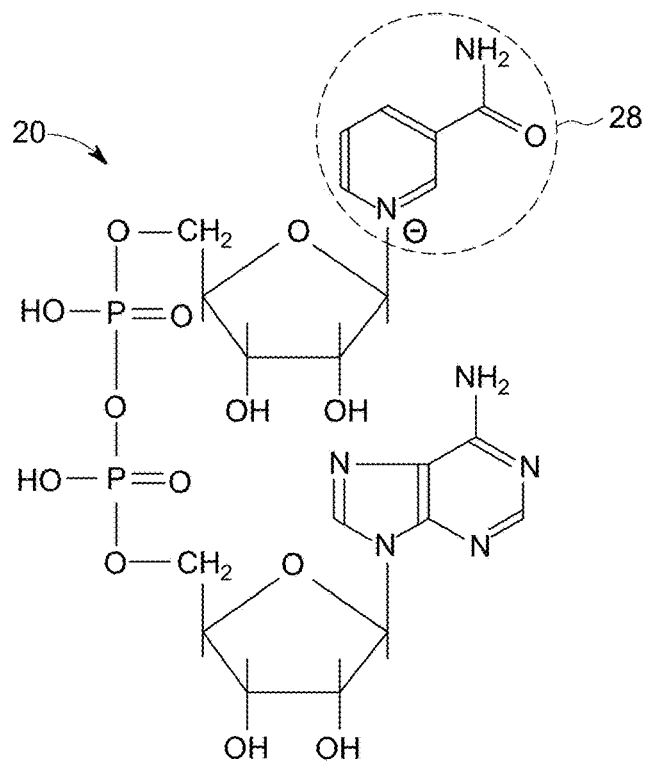
FIGS. 1A and 1B are chemical structure diagrams.
Figure 1B:
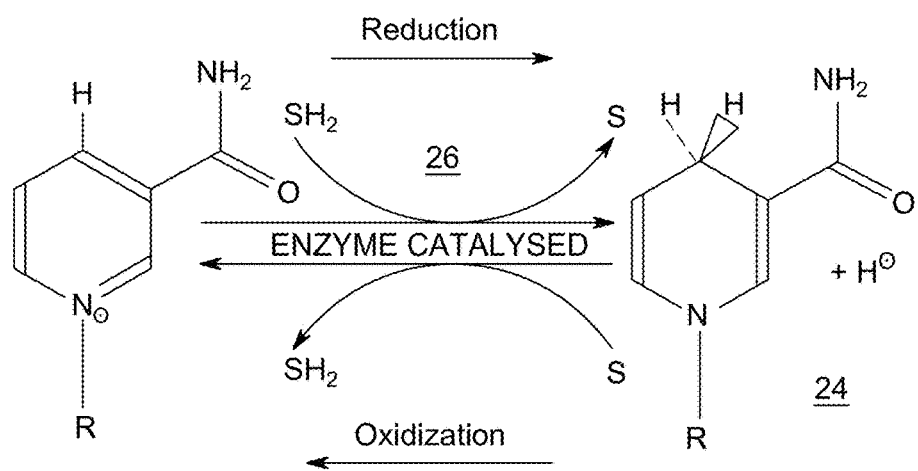
Figure 1C:
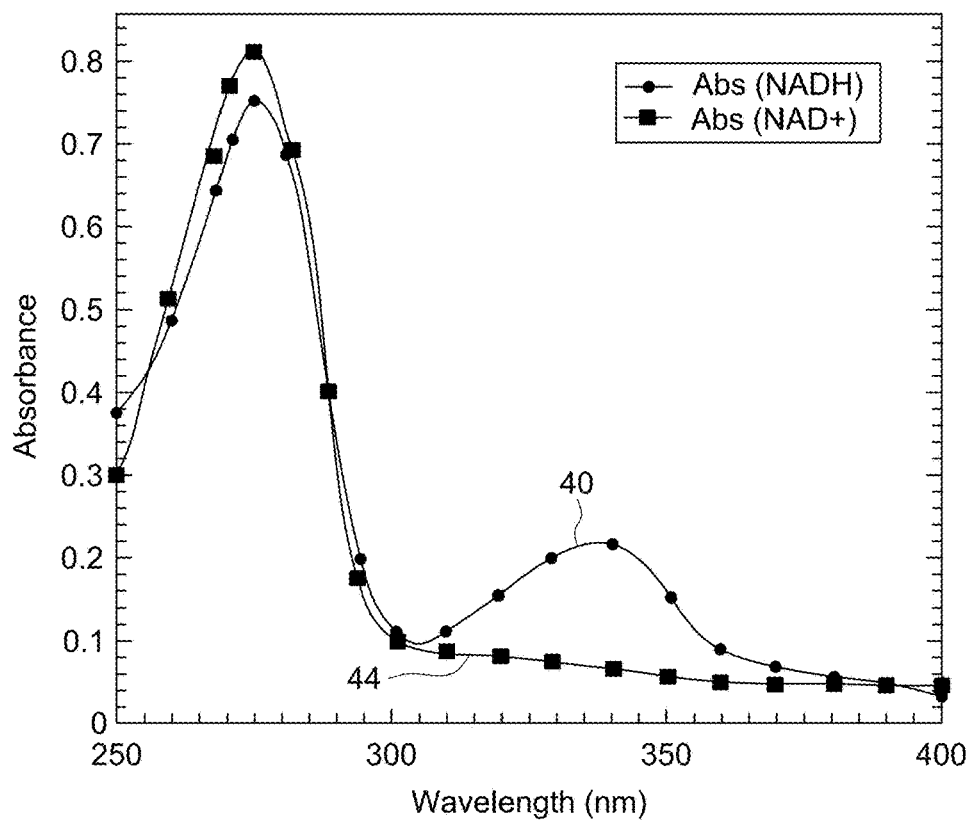
FIGS. 1C, 1D, 9B, and 9C are spectra.
Figure 1D:
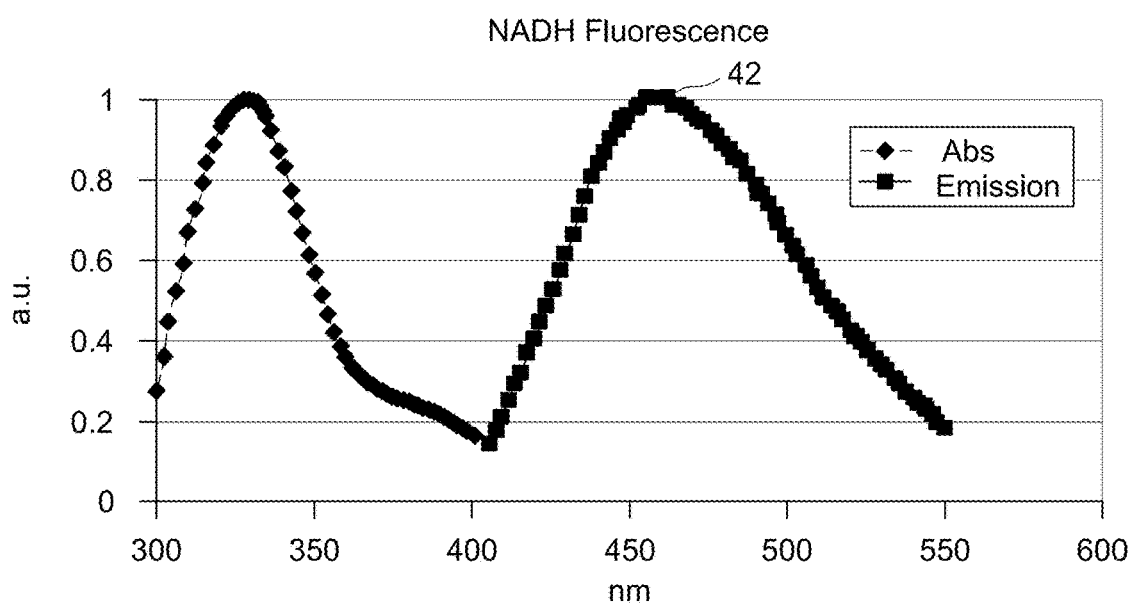
Figure 1E:
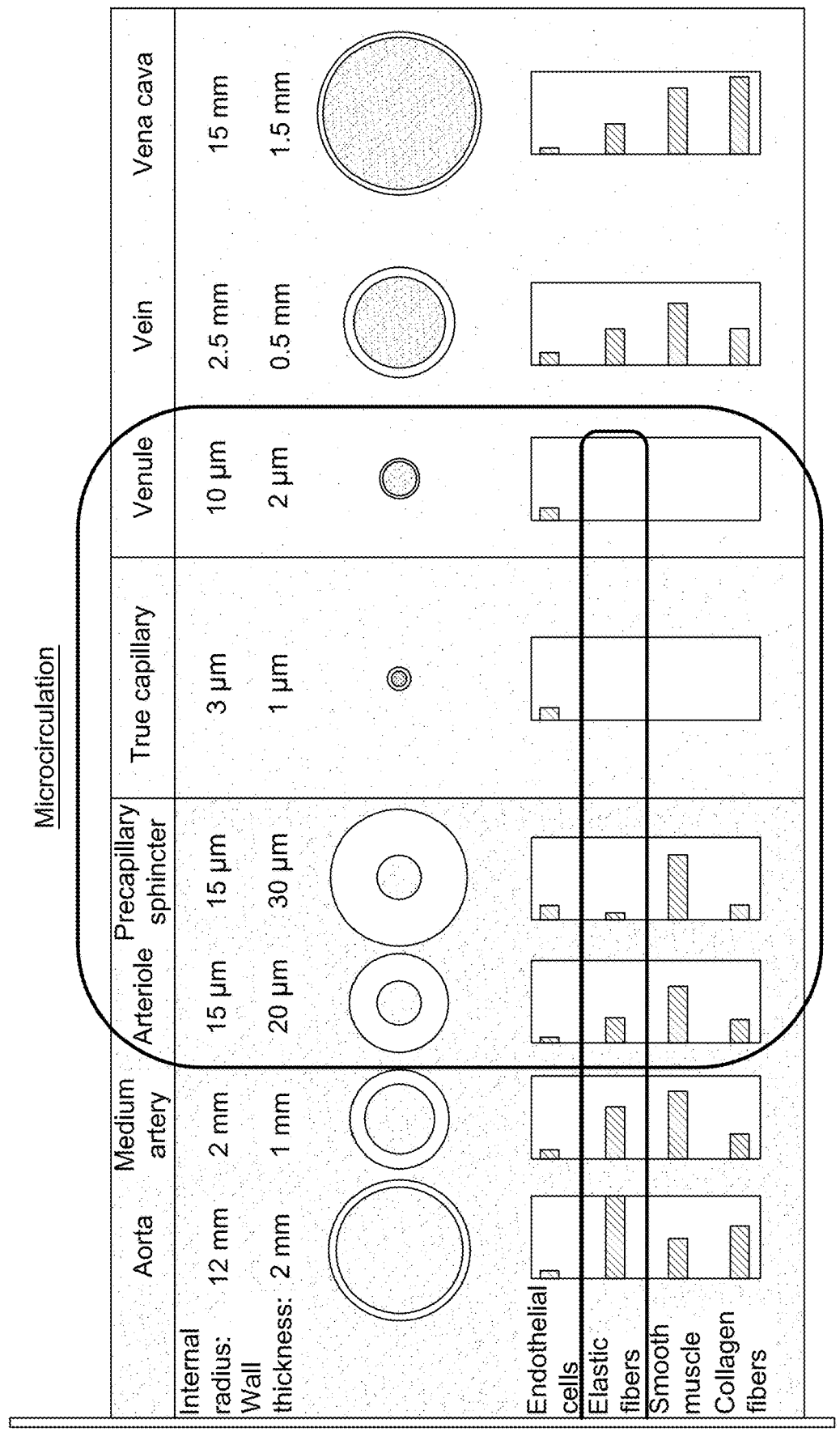
FIG. 1E is a block diagram showing portions of the circulatory system.

The four basic parameters representing the oxygen balance of a tissue in the body, tissue blood volume (TBV), tissue blood flow (TBF), oxyhemoglobin ($HbO_2$) and NADH redox state (102 from FIG. 2A), which in turn may be monitored as NADH and flavoprotein fluorescence (NADH/Fp, 42 from FIG. 1D) or NADH absorption (44 from FIG. 1C). NADH/Fp is a proxy for mitochondrial function (oxygen balance), and integrating the other three parameters monitored in the microcirculation compartment (oxygen supply) may improve diagnostic sensitivity. Tissue metabolic score 100 may provide information regarding a specific organ or about the entire body oxygen balance homeostasis depending on the monitored site. It may be desirable to integrate tissue oxygen balance measured in one or two typical organs and other systemic respiratory and hemodynamic cardiovascular parameters. In addition, other organ specific parameters will be introduced into the algorithm of organ oxygen balance homeostasis calculation.

Several characteristic forms in a trace of the tissue metabolic score are noteworthy:

An increase in tissue metabolic score is generally favorable—the current treatment of the patient is succeeding A slow decrease in tissue metabolic score is generally unfavorable—the physician should change treatment to address some change in patient condition. A down trend in a less-vital organ, such as the intestine or urethra, may give an early warning (minutes to tens of minutes) of a larger destabilization.

A single transient spike (up or down) in tissue metabolic score, in most cases, is not significant in itself. However, the general trend during the minutes following a transient is highly significant. For example, a single down-transient followed by a minute or two of decrease in tissue metabolic score, especially when observed in a vital organ such as the brain, calls for intervention.

A series of transient spikes is likewise indicative of a developing emergency. For example, a series of down-transients in the brain may indicate waves of cortical spreading depression that may indicate that the patient is at imminent risk.

Since some of the monitored parameters are not calibrated in absolute units, tissue metabolic score 100 may be computed based on relative numbers. Typically, the tissue metabolic score may have some value set (arbitrarily) around a reference value (for example, 100). The mathematical model may calculate the tissue oxygen balance homeostasis and may display the values along the time axis with a predetermined time resolution (e.g., 10 seconds).

NADH redox state 102 represents the balance between oxygen consumption and supply. FIG. 7 is a schematic presentation of the relationship of various pathological conditions and cerebral blood flow 104 and mitochondrial NADH redox state 102. A multiparametric approach, monitoring NADH redox state and blood flow, may provide better understanding of the pathophysiological processes developed. FIG. 7 illustrates improvement in differentiation between various pathophysiological states developed in the brain. By using two parameters, in FIG. 7, CBF (cerebral blood flow 104) and NADH redox state 102 (which may be measured by blue fluorescence), the clinician is able to diagnose the pathological state developed. As can be seen, NADH and blood flow are not always inversely correlated. For example, when the brain is exposed to hypoxia, NADH increases together with the increase in CBF due to the compensation process in the brain. Thus knowledge of two parameters 102, 104 may permit a more-precise diagnosis than either one alone.

The use of other physiological parameters in addition to NADH redox state 102 and tissue blood flow 104 may permit better understanding of mechanisms behind the development of pathophysiological states in various animal models and in human patients. This approach enables a clinician to better diagnose developing pathological states in patients.

One possible calculation of the tissue metabolic score 100 reflects that a clinician's subjective notion of tissue metabolic score$_1$ is about 80% correlated with NADH redox state 102, 10% with tissue blood flow (TBF) 104, and about 10% with tissue oxyhemoglobin (HbO$_2$). One possible equation is $$\text{Tissue metabolic score}_1 = 0.1 \times \text{TBF} + 0.8 \times (200 - \text{NADH}) + 0.1 \times \text{HbO}_2$$

or $$\text{Tissue metabolic score}_2 = 0.1 \times \text{TBF} + 0.75 \times (200 - \text{NADH}) + 0.1 \times \text{HbO}_2 + 0.05 \text{ Reflectance}$$

where the units of CBF and HbO$_2$ are normalized so that they vary from 0 to 100, and the units of NADH are normalized to run from 0 to 200, centered at 100 for normal. Another possible formula is $$\text{tissue metabolic score}_3 = (1.0 - 0.1 \times (1.0 - \text{TBF}_{lagging})^2) \times (1.0 - 0.1 \times (1.0 - \text{HbO}_{2\ lagging})_2) \times (1.0 - 0.8 \times (1.0 - \text{NADH})^2)$$

where the $_{lagging}$ subscript indicates that TBF or HbO$_2$ is measured over a recent time period (such as one minute), perhaps with recent measurements weighted more heavily than less recent measurements, and each of TBF, HbO2 and NADH are normalized on the interval (0.0 to 2.0) with normoxia normalized to 1.0. Tissue metabolic score$_2$ has a value of 1 when all systems are at normal, and decreases as each parameter deviates from normal.

Figure 2C:
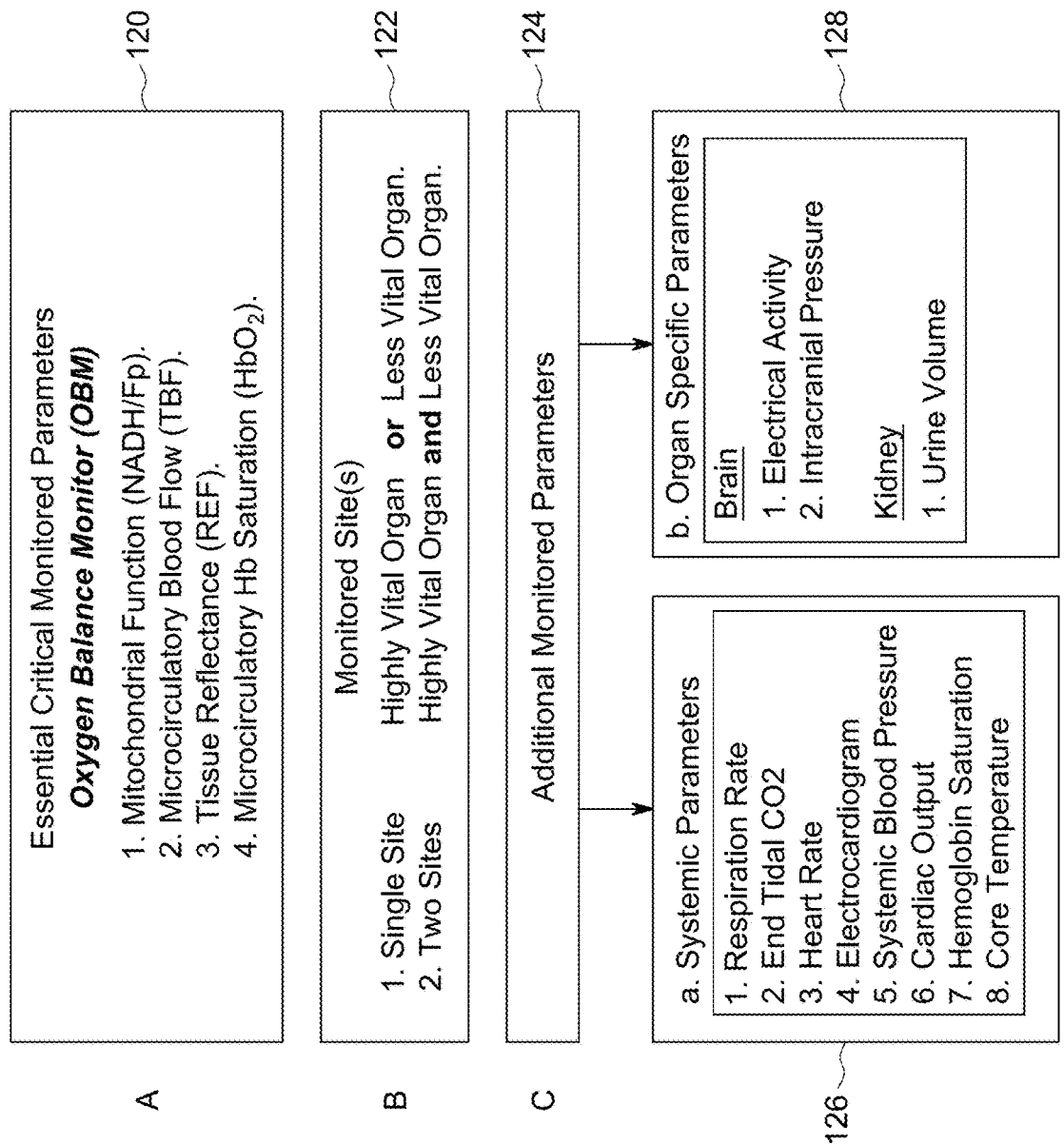
FIGS. 2C, 2D, and 2F show taxonomies of patient monitoring parameters.

FIG. 2C shows various options of monitoring systemic and organ specific parameters in animal models as well as in human patients. FIG. 2C box A 120 shows that four primary parameters could be measured in all patients in order to determine the oxygen balance at the tissue level, mitochondrial function (NADH/Fp), tissue/microcirculatory blood flow (TBF), tissue reflectance (REF), and microcirculatory hemoglobin saturation (HbO$_2$). The suggested monitoring system contains a mathematical model based on the changes in the monitored parameters that will calculate and display a computed tissue metabolic score 100 that represents the vitality of the tested organ at the tissue level.

It is possible to monitor one or two sites simultaneously as shown in FIG. 2C box B 122.

Figure 2D:
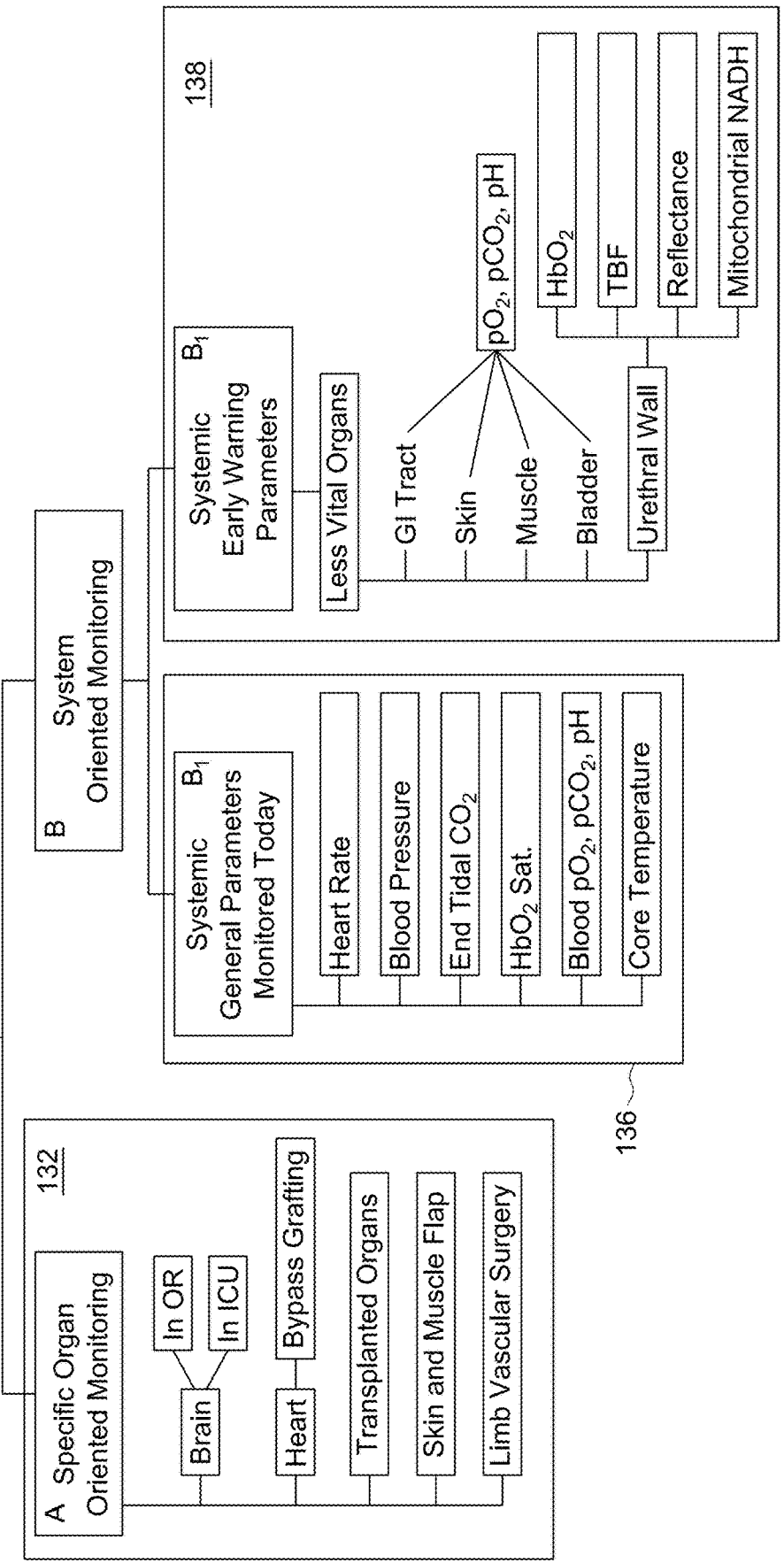

Referring to FIG. 2D, patient monitoring may take place in real time at two levels. The left branch 132 of FIG. 2D shows monitoring of the function of specific organs. The right branch 134 shows monitoring of systemic parameters. Branch 136 includes systemic general parameters that are monitored today (temperature, heart rate, blood pressure, end tidal CO$_2$, HbO$_2$ oxygen saturation, blood levels of O$_2$, CO$_2$, and blood pH). Branch 138 shows systemic early warning parameters that could be monitored at the tissue level, especially in less-vital organs (such as the gastrointestinal tract, skin, muscles, bladder, and urethral wall), including pH, levels of O$_2$, CO$_2$, HbO$_2$ oxyhemoglobin, tissue blood flow, tissue reflectance (which correlates with blood volume), and mitochondrial NADH redox state.

The tissue metabolic score may help the clinician evaluate and understand the functional state of various tissues of the body, for example the brain, in real time. A tissue metabolic score that integrates multiple parameters, such as microcirculatory blood flow, oxygenation of the hemoglobin, NADH redox state may be a practical and useful tool. In daily clinical practice, the time available for the clinician to evaluate the large number of monitored parameters is very limited. Therefore, calculating a score that integrates various parameters based on big data may provide a quickly-interpretable evaluation of clinical status of patients.

Figure 2E:
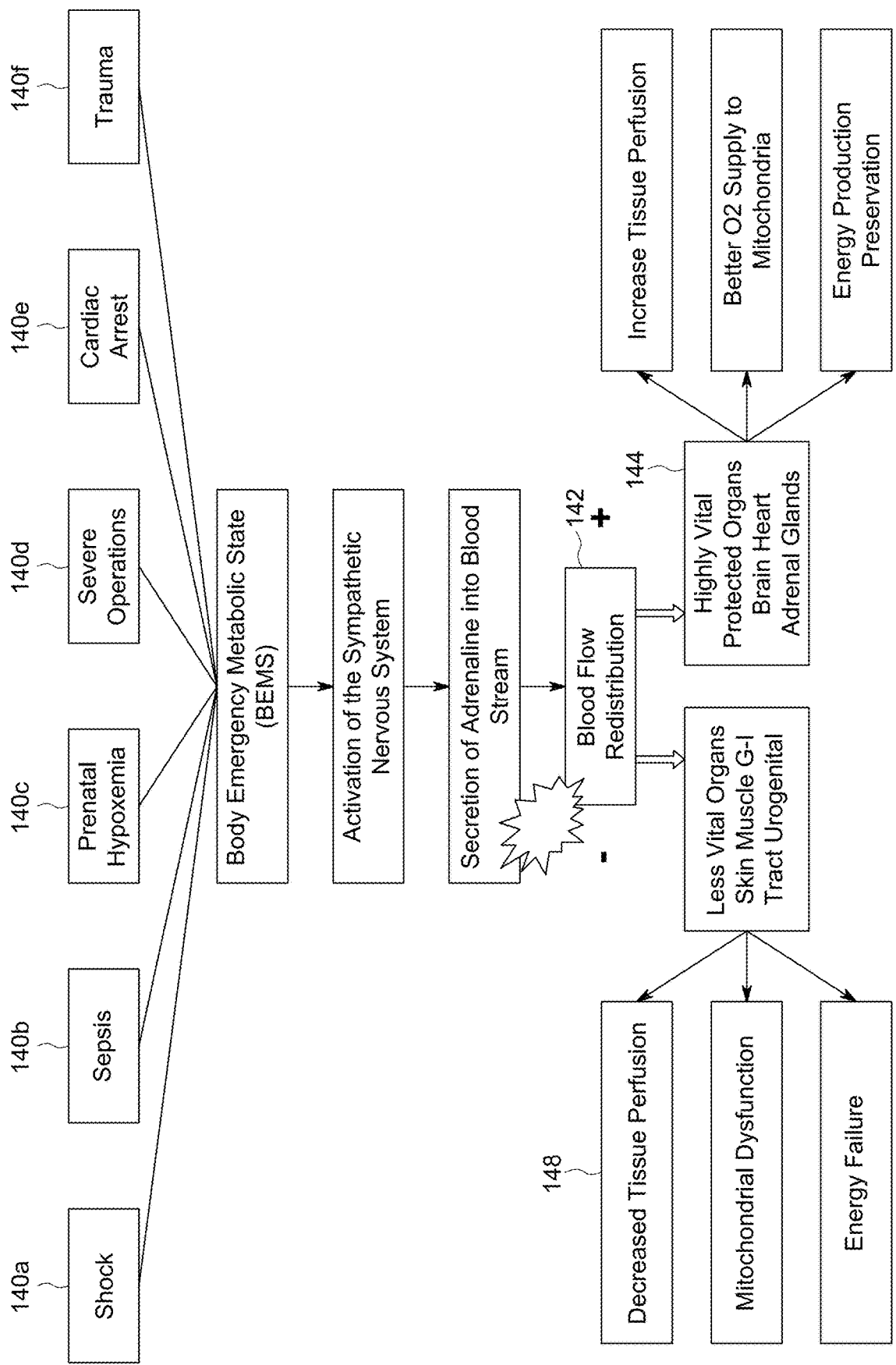
FIG. 2E shows pathological states developed under various clinical situations that lead to the development of body emergency metabolic state (BEMS).

FIG. 2E is a schematic presentation of various pathological states developed under various clinical situations, which lead to the development of body emergency metabolic state (BEMS) and physiological responses. As a result, blood flow redistribution will lead to an increase in blood flow to the most vital organs and a decrease in blood flow to the less vital organs. As presented in FIGS. 2D and 2E, negative oxygen balance will activate the mechanism of blood flow redistribution between organs in the body in order to protect the most vital organs in the body, the heart and the brain. The intestine could be used as a surrogate monitored organ to the two highly vital organs in the body (brain and heart). The conclusion from animal monitoring is that by monitoring of less vital organ an early warning signal of negative oxygen balance will be displayed and the treatment could be started before the heart and the brain will be damaged. The clinical implication is that in the operating rooms (OR) or intensive care unit (ICU) the supply of oxygen to the heart and the brain will be kept in the normal range and normal function is more likely maintained.

Figure 2F:
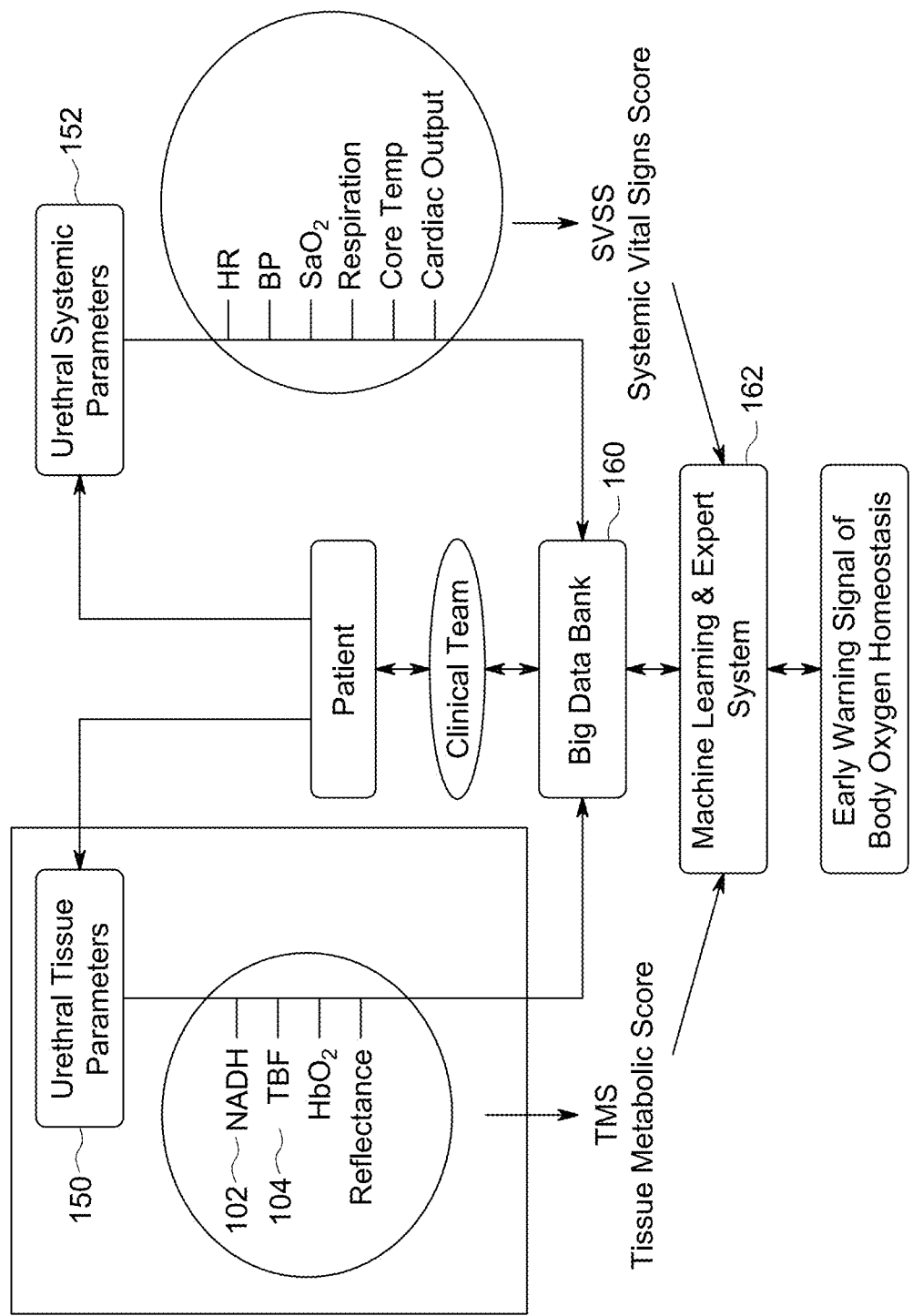

As shown in FIGS. 2C and 2F, two groups of parameters may be monitored simultaneously in the same patient. The tissue oxygen balance may be monitored by the four parameters shown in FIG. 2C box A 120 (mitochondrial function (NADH/Fp), tissue/microcirculatory blood flow (TBF), tissue reflectance (REF) and microcirculatory hemoglobin saturation (HbO$_2$)). In addition, the systemic parameters shown in FIG. 2C box 126 are measured in most patients in the OR (operating room) and ICU (intensive care unit). Also, the evaluation of kidney function by measuring urine volume is a standard of care in most patients.

In turn, the tissue oxygen balance parameters may be subdivided into mitochondrial function and microcirculation parameters. Mitochondrial function may be evaluated by monitoring the NADH redox state 102, which in turn may be monitored by fluorescence (420-480 nm blue). This information is collected from the intracellular compartment-from the mitochondria. Microcirculation may be measured, for example, by parameters such as tissue blood flow (TBF) 104, reflectance (REF), and oxyhemoglobin (HbO$_2$), measured in intravascular blood. Physiologically there is connection between these four parameters, but the relationship is not simple and therefore we have to measure all of them simultaneously.

Referring to FIG. 2F, patient diagnosis and treatment may be improved by supplementing traditional monitoring of patent systemic vital signs with monitoring of specific organs and computing a tissue vitality score. For example, FIG. 2F shows patient monitoring of systemic parameters (152, right side):

BP—blood pressure
HR—heart rate
Temp—body temperature
SaO$_2$—systemic blood oxygen saturation
ET CO$_2$—end tidal CO$_2$
Body temperature Cardiac output
Urine volume
and tissue metabolic parameters specific to one organ (in this case, the urethra) on the left side 150.
NADH 102—mitochondrial NADH redox state, as measured by NADH/Fp fluorescence
tissue blood volume 104
HbO$_2$ (hemoglobin oxygenation)
REF—tissue reflectance at 320-380 nm All parameters monitored for the patient may be stored in a data bank 160 for analysis using machine learning, expert system, and other big data analysis techniques 162.

Table 1 demonstrates the principles of translating the responses of the brain to the changes in oxygen supply by calculating the homeostasis level of oxygen in the brain using the tissue metabolic score.

TABLE 1

Calculation of the Tissue Oxygen Balance
Homeostasis level in the gerbil brain.

|  | NADH | Blood flow | HbO$_2$ | Reflectance | TMS |
| --- | --- | --- | --- | --- | --- |
| Base-line | 100% | 100% | 100% | 100% | 100 |
| Ischemia Partial 50% | 150% | 50% | 50% | 120 | 50% |
| Ischemia complete | 200% | 0-3% | 0-5% | 150% | 0-2% |
| Anoxia (0% oxygen) | 200% | 140% | 0-5% | 70% | 2-5% |

II. Use of the Tissue Metabolic Score

Referring again to FIG. 2A, the tissue metabolic score may present three types of trend records:
1. Stable tissue metabolic score as compared to the initial calibrated reference value (typically 100). Small random fluctuations (for example, five to ten percent) from the initial value are acceptable as a stable situation.
2. Continuous decrease of the tissue metabolic score of more than 5% is an indication that there is deterioration in the oxygen homeostasis. This trend could be used as an early warning signal, indicating the needs to change treatment of the patient.
3. Continuous increase of the tissue metabolic score from the initial calibrated score by 10% or more. This situation suggests that the patient was in negative oxygen balance at the beginning of the monitoring, and is now in improved condition, perhaps due to the treatment given.

II.A. Correlation of the Tissue Metabolic Score to Physiological State

Referring again to FIG. 2E, several pattern cascades of pathophysiological events may occur in many emergency clinical situations in adult patients that may lead to morbidity and mortality. Various pathological states may lead to metabolic disturbances and may end up in cellular energy derangement.

The six pathological states shown in FIG. 2E 140a-140f are the most common life-threatening events that may develop in clinical practice. Each may develop due to a specific event, such as a major operation, or during slow process of body deterioration, such as in sepsis or shock. The definition of each of those six states is not so well established, and some overlapping may exist. Under all those situations the metabolic state of the body will be deteriorated and energy failure will develop.

Situations 140a-140f shown in FIG. 2E could develop in patients hospitalized in various operating rooms or intensive care units (including the respiratory, neurosurgical, cardiac and neonatal ICU). Also, all patients undergoing major surgery such as cardiac bypass, neurosurgical or organ transplantation, and the like may develop the body emergency metabolic state (BEMS). Other patients that may develop the BEMS are newborns during delivery or elderly patients treated in the internal medicine departments.

As a central protection mechanism, the body will redistribute 142 blood flow in favor of the three protected organs 144 (brain, heart and adrenal gland), which will receive more blood and oxygen while the peripheral organs 146 or areas (skin and muscles), as well as others less vital visceral organs, will undergo vasoconstriction and a decrease in blood flow and oxygen supply. Monitoring of cellular function is a significant indicator of the metabolic state of patients in critical care medicine. The urethra is especially sensitive, since it is one of the earliest organs to lose blood supply, and is easily accessible to a surface probe.

The energy balance in the most vital organs will remain positive due to higher blood flow while the less vital organs will be hypoperfused and a negative energy balance will develop 148. As presented in FIG. 2E, the blood flow redistribution mechanism 142 will affect the energy production by the mitochondria in the most vital organs 144 and less vital organs 146 in the body differently. This change in mitochondrial function will affect the production of ATP. The different response of different tissues may provide diagnostic insight and treatment recommendations.

II.B. Example 1: Blood Loss in a Patient

In a patient is admitted after losing a lot of blood (e.g., after a car accident), a Foley catheter may be used to insert a probe for tissue metabolic monitoring of the urethra. Parameters underlying the patient's tissue metabolic score may be monitored, and a tissue metabolic score may be computed, and normalized to 100 as an arbitrary initial reference point. After giving infusion of blood, the clinician needs some information regarding the efficacy of the infusion. If the calculated tissue metabolic score increases to 110% and later on to 120%, the interpretation is that the added blood is beneficial to the patient. If the next infusion blood does not affect the score, then the clinician may stop the infusion of blood. Under this situation, the clinician may infuse more physiological Ringer's solution in order to increase to water balance in the body. This infusion may keep the tissue metabolic score at the same level or may lead to decrease in the tissue metabolic score. Another option may be to increase the level of oxygen in the breathing mixture, e.g., from 21% to 40-50%. If the tissue metabolic score is not affected by this treatment, then the clinician should avoid the elevation of oxygen supply and avoid the side effects of high oxygen in the mixture (oxygen toxicity).

II.C. Example 2: Heart Bypass Operation

Figure 3A:
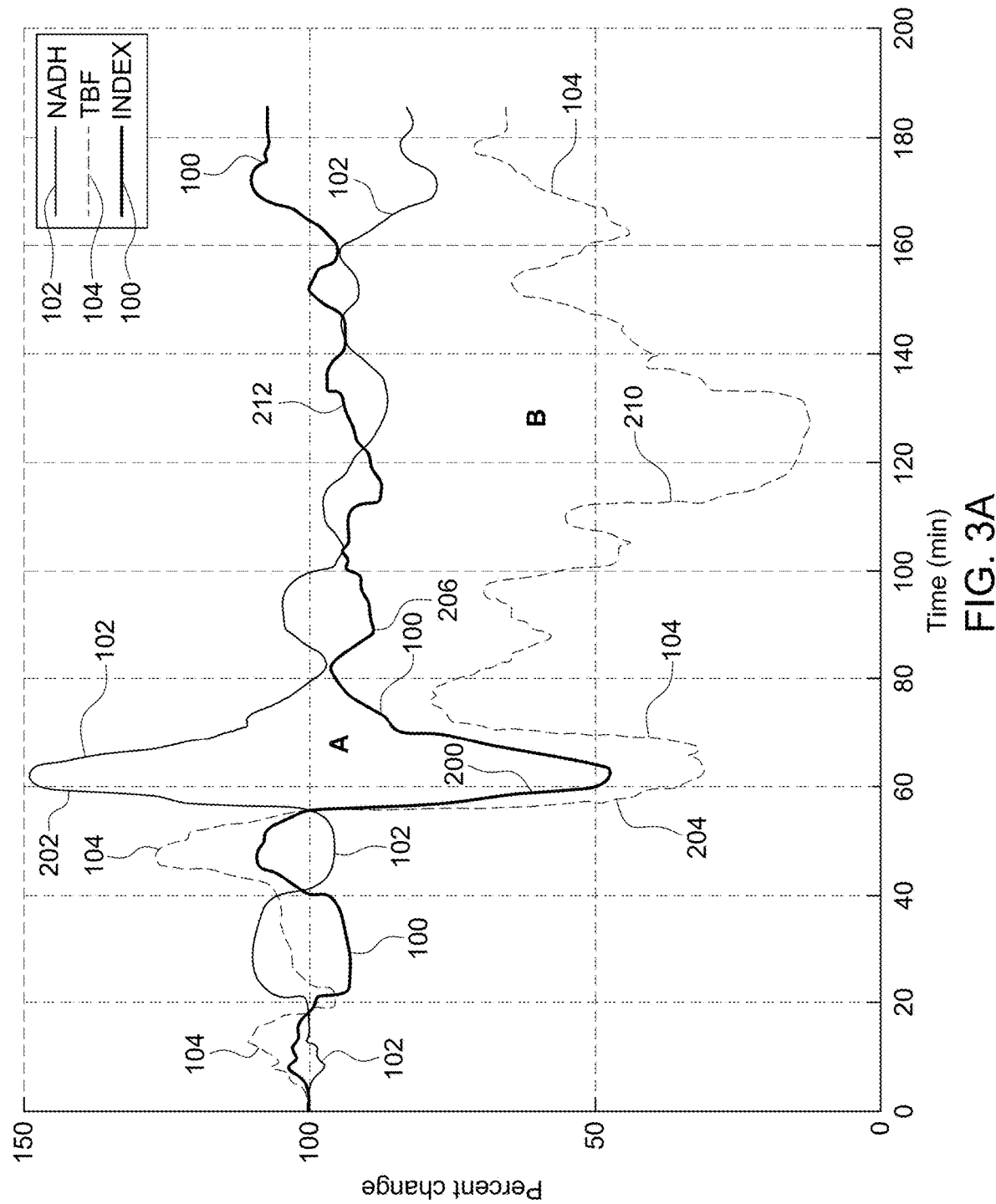

Referring to FIG. 3A, a patient was monitored using a urethral catheter during a heart bypass operation. At time 55 minutes, a large bleeding occurred due to the cut of a large artery during the incision of the chest. Blood flow decreased dramatically 204 and due to the decrease of oxygen, a large increase in NADH signal 202 was recorded. The calculated tissue metabolic score (100, the trace that is in the center from time 60 to 100) dropped immediately, and recovered to "baseline" 206 as soon that the bleeding was stopped and the patient was connected to a heart lung machine. At time 100 minutes, the patient's body temperature was decreased in order to protect the brain against lack of oxygen. Under those hypothermic conditions (17° C. at time 100) another event of decrease in blood flow 210 was recorded (trace 104 at time 110 minutes) but the NADH (trace 102) remained stable 212 at this very low body temperature. The tissue metabolic score value after time 110 was not affected probably due to the hypothermia. If only blood flow was monitored, the clinician will not obtain the real physiological status of the patient that is presented only by the stability of the mitochondrial NADH signal 102.

In FIG. 3A, the tissue metabolic score is represented by trace 100 (which is the center of the three traces between times 55-120, and the top trace from times 150-190). Hypothermia is a major tool or treatment used clinically in order to protect the brain from decrease in oxygen supply. The hypothermic brain lowers oxygen consumption and therefore oxygen balance in the brain will remain stable, even under decreased oxygen flow. This effect is seen in at time 110 when the blood flow showed a large decrease but the NADH 102 remained relatively stable. This difference between the responses of the tissue metabolic score 100 (center trace) between the bleeding event at time 55 and the decrease in blood flow due to induced hypothermia at time 110 demonstrates the efficacy of the hypothermia in protecting the brain against possible ischemia, and the efficacy of the tissue metabolic score in identifying stability of the patient.

FIG. 3A shows that a clinician using tissue metabolic scoring may observe mitochondrial function in patients in real time, and use that information in making clinical decisions. The bleeding event at time 55 was reflected in a decrease in the TMS 200 indicating that body oxygen balance is negative and therefore the brain may suffer from the lack of oxygen, and that the clinician must therefore take action to improve the oxygen balance in the brain (either to supply more oxygen or decrease oxygen consumption). In contrast, at time 110, though the blood flow to the lower part of the body dropped sharply 210, the TMS remains stable 212. This stability 212 in the TMS tells the clinician that even though there is a large decrease in blood flow 210, that blood flow decrease is not crucial, because the hypothermic condition is adequately protecting the brain. Even though the monitoring is at the urethra, because of the early response nature of urethral blood flow, urethral monitoring gives insight into the oxygen balance in a vital tissue such as the brain.

II.D. Example 3: Tissue Oxygen Balance Analyzer

FIG. 3B reflect monitoring of a gerbil brain for mitochondrial function and microcirculatory blood flow and oxygenation, and shows the effect of ischemia 222 (left side, events 1, 2, and 3) and anoxia 224 (right side, events 4 and 5). This system includes an OBM (oxygen balance monitor) of FIG. 2C box A 120 that provides real time information on the changes in the four parameters (NADH fluorescence (NADH/Fp), microcirculatory tissue blood flow (TBF), tissue reflectance (REF), and microcirculatory hemoglobin oxygen saturation ($HbO_2$)) monitored simultaneously from a tissue in the body. The monitoring traces may be stored digitally. Each one of the four signals is defined in terms of minimal and maximal values to provide the dynamic range. After placing the probe in contact with the brain tissue, the base line values of the four parameters are determined. In monitoring of an animal model or specific cases in patient monitoring, it is possible and recommended to identify the energy balance of the tissue at this monitoring stage. It is possible to perturb the tissue by lowering the oxygen supply in a standard way, e.g., a short ischemia or anoxia. FIG. 3B presents two types of responses, ischemia and anoxia, measured from the brain of the Mongolian gerbil using the OBM. The responses to ischemia 222 were induced by occlusion of the common right carotid artery (partial ischemia, event 1) followed by adding the occlusion of the left carotid artery (complete ischemia, event 2).

In FIG. 3B, the right side shows the responses to anoxia 224 (100% nitrogen exposure). As seen, the two events 222, 224 (1-3) and (4-5) induce a severe decrease in oxygen availability and therefore $HbO_2$ shows the same decreased hemoglobin oxygenation 226, 228. As a result, the availability of oxygen in the mitochondria goes very low and therefore NADH signal is elevated 230, 232 to the maximal level under the two perturbations. The responses of the TBF 234, 238 and the reflectance 236, 240 are opposites under the two events that led to the same degree of oxygen deficiency. The reason is that brain blood flow 234 and blood volume (reflectance) 236 is decreased during ischemia and increased 238, 240 during anoxia. These responses demonstrate the significance of the multiparametric monitoring approach as compared to single parameter monitoring. The sole parameter that shows the same response, under the two conditions of oxygen deprivation, is the NADH redox state 242, 244 representing mitochondrial function. The responses of the NADH 242, 244 are very symmetrical during the normoxia-ischemia and normoxia-anoxia transitions without undershoot or overshoot seen in the other parameters' responses.

In FIG. 3B, the bottom trace 100 shows the tissue metabolic score calculated from the traces above in FIG. 3B. As seen, the decrease in the tissue metabolic score is very similar in the two events 222, 224 (1-3 and 4-5) although the CBF responses 234, 238 were in opposite directions. In the ischemic event 222 the CBF decreased 234 due to the occlusion of the blood vessel to the brain. In the anoxic event 224, the blood vessel to the brain remained opened but the blood flowing to the brain was not carrying oxygen. Due to the lack of oxygen, the body compensated by elevating blood flow 238, but due to the induced anoxia, no additional oxygen arrived in the brain. However, in both events, the tissue metabolic score responded similarly 250, 252, in both cases indicating an oxygen imbalance. In this case, a single parameter, CBF, does not communicate enough information to guide physician action. In contrast, in both events 222, 224 (1-3 and 4-5), the similar TMS 250, 252, more reliably indicates to a clinician that the brain is experiencing a critical deprivation of oxygen. A depression of TMS may arise from any of several underlying causes: a reduction in blood flow, a reduction in oxygen carried in the blood, a toxin that prevents oxygen uptake (for example, carbon monoxide or some toxin that similarly interferes with oxygen uptake), and others. An advantage of the TMS score 100 is that it is sensitive to most of these disruptions of oxygen delivery, and can be measured at the tissue level. The TMS score may accurately alert a clinician to a critical situation that requires immediate attention.

FIG. 3B may be extrapolated from a gerbil to a human to guide treatment decisions. For example, in a patient admitted after a severe stroke event, the clinician may insert a multiparametric monitoring probe into the subdural brain area and measure the four parameters presented in FIG. 3B, perhaps supplemented by macro circulation parameters (such as blood pressure and/or $O_2$ sat), and also measure the four parameters in the urethra using sensors on a Foley catheter. From these parameters, a tissue metabolic score for the brain ($TMS_B$) and urethra ($TMS_U$) may be calculated. If brain TMS is moving up and blood pressure and urethral TMS are stable, the clinician may conclude that the oxygen balance of the entire body is stable and the brain oxygen balance is improving, and that in this case, present treatment may continue. If the brain TMS is decreasing together with a decrease in urethral TMS, the patient is likely in an urgent emergency condition, and the clinician should take emergency action to improve total body oxygen balance. For example, typically more oxygen should be added to the breathing mixture and blood pressure should be kept in the upper possible range.

Figure 3D:
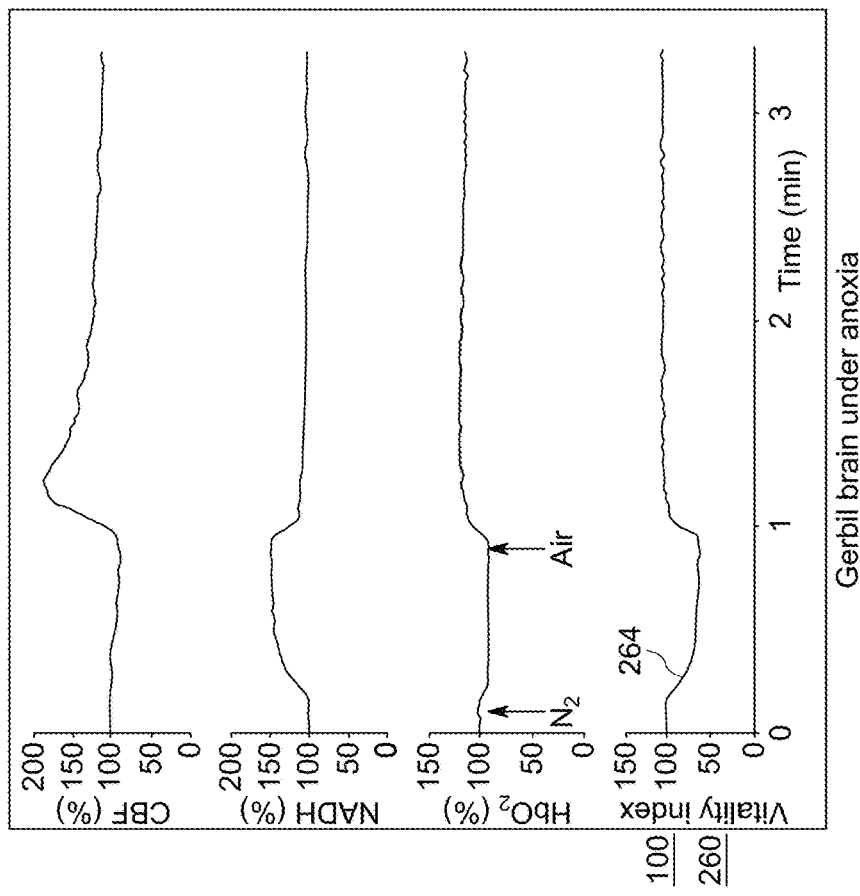
Figure 3C:
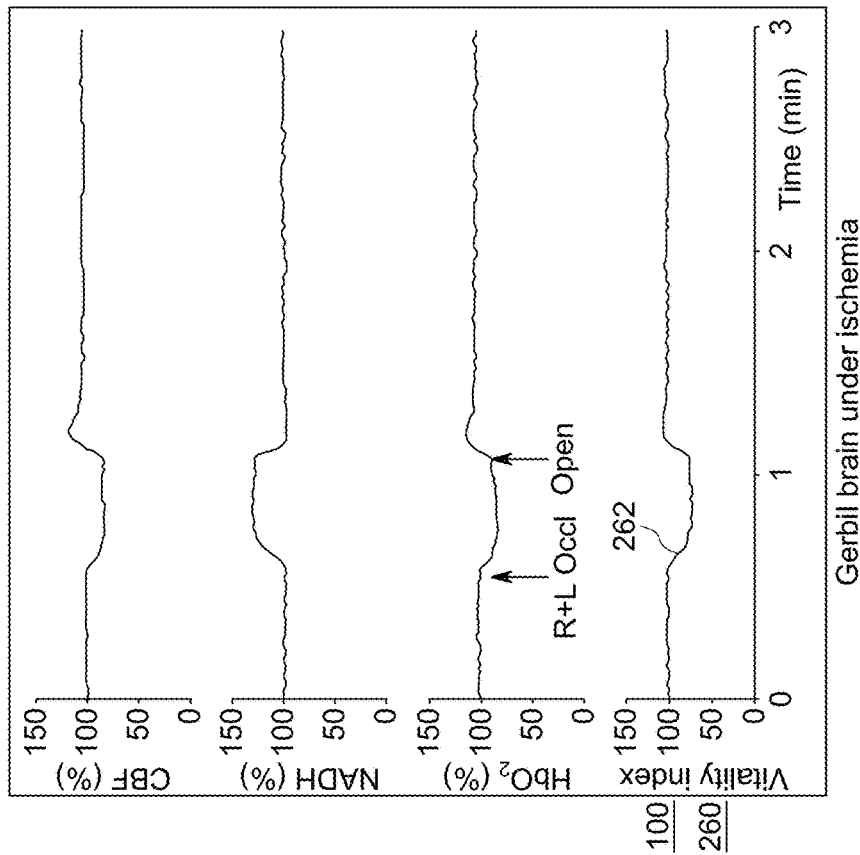

FIGS. 3C and 3D show, in a gerbil brain, the effects of complete ischemia (FIG. 3C) and anoxia (FIG. 3D) on the tissue metabolic score calculated from the three parameters (NADH CBF and $HbO_2$). In both FIG. 3C and FIG. 3D, the tissue metabolic score falls, alerting the clinician that the brain is suffering from the lack of oxygen and in order to save this brain from irreversible damage fast action is needed. In both situations, the drop 262, 264 in TMS identifies tissue distress that calls for prompt treatment of the patient, even if the underlying cause is not clear. Any drop in the monitored TMS alerts the clinician that something is amiss, and the clinician should promptly investigate and restore systemic, macro circulation, and microcirculation parameters to their normal ranges.

Figure 3E:
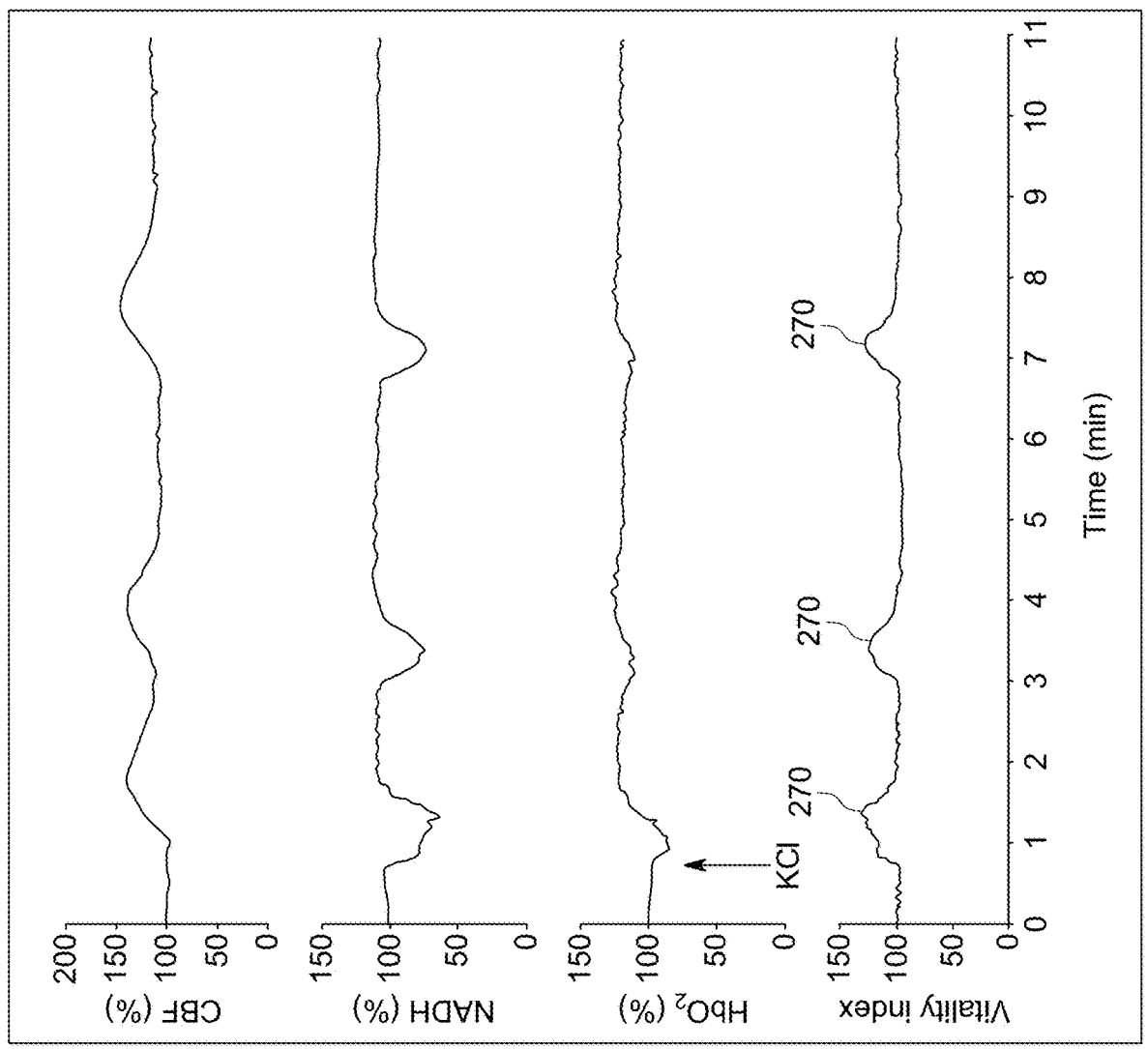

FIG. 3E is also a gerbil brain, with exposure to potassium chloride, which induces cortical spreading depression. The response is analogous to and typical of patients suffering from stroke or severe head injury. In such patients, the tissue metabolic score may diagnose and give an early warning of cortical spreading depression. The up-transients 270 in tissue metabolic score indicate an increase in oxygen consumption created by the shift in potassium ions between the intracellular and extra cellular space (see references [Mayevsky2013] and [Mayevsky1996]). The calculated increase in the tissue metabolic score is mainly due to the oxidation (decrease) of NADH created by the higher utilization of oxygen.

A head injury or stroke patient should be monitored by a probe on the brain below the dura mater (such subdural probes are discussed in Example 2F and FIGS. 8B and 8C). Because this patient may suffer from secondary events that may develop after hospitalization, continuous monitoring of the brain may be critical to diagnosis of the patient. After admission and monitoring begins, the TMS of the brain may behave in at least four patterns as a function of time—the TMS may be stable, increase, or decrease, or exhibit a series of transients. (The trend of the TMS and not the value by itself is important in cases where TMS is computed as a relative value.)

An uptrend or stable is generally good, and indicates that treatment should continue on present course.

A downtrend indicates that the patient is deteriorating, and treatment should change to restore oxygen metabolic balance (see further discussion in Example 5, discussing FIG. 4D).

A series of transient short changes (for example, the series of up-transients as shown in FIG. 3E) over a steady baseline indicates that the brain is exposed to event such as cortical spreading depression developed due to the pathological state of the patient's brain. Up-transients should alert the clinician to the possibility of spreading cortical depression, and the possibility of a downtrend emerging in the near future. The up-transient may be treated with some increase in oxygen supply, or to slightly increase $CO_2$ level in the breathing mixture. Also the clinician should keep the ICP (intracranial pressure) in the normal range if possible by adding a bolus of mannitol.

II.E. Example 4: Cortical Spreading Depression in a Rat Brain

FIGS. 4A and 4B show monitoring of a rat brain. In FIG. 4A, the rat is normoxic, and in FIG. 4B, the rat is hypoxic. In both FIGS. 4A and 4B, cortical spreading depression (CSD) is triggered by placing a high concentration potassium chloride solution (KCl) on the surface of the brain. The vertical lines in FIGS. 4A and 4B indicate the spontaneously developed neuropathological event named CSD (Cortical Spreading Depression) developed in a patient after severe head injury (see [Mayevsky1996]).

The reflectance (R) signal 302 is an indirect indicator of events developed in the microcirculation. In FIG. 4A, the CSD developed in a normal brain led to an initial short and small vasoconstriction 304 (increase in reflectance due to decrease in blood flow and volume) followed by a longer and deeper decrease in R 306 due to increase in blood flow and volume which absorbed more light (smaller reflectance). In FIG. 4B, the CSD was induced in brain that was exposed to mild hypoxia. Under those conditions the microcirculation had a limited capacity to increase blood flow to supply more oxygen needed for the recovery from the CSD event. Therefore, the shape of the R signal looks different. The initial vasoconstriction 308 (increase in R) was larger followed by a longer vasodilation 310 (decrease in R). This issue was discussed in our papers [Meilin1995] and [Sonn2012]. Due to the different response of the microcirculation to CSD, the mitochondrial response was opposite as seen in the CF (NADH) signal in FIGS. 4A and 4B. In FIG. 4A, oxygen was available and the NADH became more oxidized 312 and in FIG. 4B, the NADH became more reduced 314. The inversion in the shape of the NADH response to CSD was described in detail in [Mayevsky1978] and [Mayevsky1992]. Subsequent work showed that under conditions of imbalance of oxygen supply/demand the NADH response to cortical spreading depression was inverted depending on availability of oxygen.

The rat study of FIGS. 4A and 4B may be extrapolated to human neurosurgical patients. The transient pulses in TMS (either up-transients 316 or down-transients 318) as shown in FIGS. 4A and 4B indicate likely CSD, and that in turn, indicates the beginning of brain deterioration, requiring immediate intervention by the clinician. In a few cases, the CSD may develop after an event of epilepsy that often develops after severe head injury. If the duration of the epileptic or CSD events is relatively short (in the range of 10-30 minutes) the clinician may not have to intervene. If the transient pulses in the TMS and visible epilepsy symptoms continue for more than thirty minutes, the clinician should treat the patient with anti-epileptic drugs that may prevent the development of events that could damage the brain. If the TMS exhibits one or more up-transients (for example, 316 of FIG. 4A) followed by down-transients (for example, 318 of FIG. 4B), this is a high likelihood indicator that the brain of the patient is deteriorating. The clinician must immediately attend to all systemic parameters to bring them to normal range and also must improve the supply of oxygen to the brain.

The tissue metabolic score values shown in the lowest trace of FIGS. 4A and 4B are affected by the changes in the responses of the mitochondrial function to the CSD. In FIG.

4A, the transition in TMS started as a clear increase wave 316 during the activation of the energy metabolism in the brain tissue. In FIG. 4B, the decrease 318 in the TMS amplitude that became more pronounced suggests that an event such as mild hypoxia was the reason for it. The change in the shape of the tissue metabolic score indicates that the oxygen balance in the hypoxic brain is negative and show that the brain was damaged by the increased oxygen consumption during the CSD under hypoxia. Extrapolating from animal models, the inverted (increase) response of NADH or down-transient 318 of the TMS indicates a need to correct the brain's oxygen balance toward baseline, typically by improving the supply of oxygen to the brain. This information could be also applied to treat patients in cases that oxygen balance becomes negative.

Extrapolating from a rat model to a human patient, a physician may expect that in a patient admitted for severe head injury or exhibiting decrease in oxygen supply due to local brain ischemia, one would desirably monitor the four parameters shown in FIG. 2C box A 120 (mitochondrial function (NADH/Fp), microcirculatory blood flow (TBF), tissue reflectance, and microcirculatory hemoglobin saturation ($HbO_2$)) in the brain, and compute the tissue metabolic score trace. A dip in the tissue metabolic score trace likely indicates a negative oxygen balance in the brain, and the physician should take action to restore the oxygen balance to the normal range. This could be achieved by increasing oxygen level in the breathing mixture, or by a small elevation of the $CO_2$ in order to increase cerebral blood flow. Conversely, for the same patient, elevation in tissue metabolic score, paired with a decrease of ICP (intracranial pressure) or normal EEG record, indicates an improvement of the physiological state of the brain, and the physician should wait and follow the stabilization of the patient.

Results recorded in a rat model were paralleled by results observed in patients after traumatic brain injury, as discussed in Example 5.

II.F. Example 5: Cortical Spreading Depression in a Human Neurosurgical Comatose Patient Referring to FIGS. 4C and 4D, these traces reflect monitoring of the brain of a patient that entered the intensive care unit in a comatose state due to severe head injury, as described in [Mayevsky1996]. After admission to the neurosurgical unit the patient was connected to a multiparametric monitoring system. During the measuring period, this patient was bilaterally irresponsive to pain; his pupils were dilated and non-reactive to light. He was mechanically ventilated and his brain CT scan showed evidence of severe brain edema in the left hemisphere and right parietal hemorrhagic contusion. The measurements were taken from the right frontal lobe. At 4.5 hours after the beginning of monitoring, which was seven hours after admission to the hospital, the event seen in FIG. 4C was observed. Thirty minutes later, the event seen in FIG. 4D was recorded and was followed by similar events over the next few hours. The response of NADH fluorescence (and other parameters) in this human patient in FIGS. 4C and 4D is similar to that of the rat brain shown in FIGS. 4A and 4B.

As seen in FIG. 4C, the ECoG (electrocorticography, a type of monitoring that uses electrodes placed directly on the surface of the brain) became depressed for 10-15 minutes 332 and at the same time a cycle of NADH oxidation 334 while blood flow and volume increased 336. The transient up-peak 338 in the TMS trace reflects increased blood flow, and warns the clinician of CSD (cortical spreading depression). This patient exhibited repetitive CSD (cortical spreading depression) cycle every 20-30 minutes.

FIG. 4D shows changes about 4.5 hours later, about seven hours after admission to the hospital, taken from the right frontal lobe. During the measuring period, this patient was bilaterally irresponsive to pain; his pupils were dilated and non-reactive to light. He was mechanically ventilated and his brain CT scan showed evidence of severe brain edema in the left hemisphere and right parietal hemorrhagic contusion as shown in FIG. 4D, the following spreading-depression-like cycles that were recorded from this patient (after the first ones) showed different hemodynamic and metabolic responses. NADH oxidation cycles were replaced by a biphasic cycle comprised mainly of a phase of increased NADH 342 followed by a small oxidation phase 342. The compensation of blood flow and volume 344 was also reversed at this time. The monophasic increase in CBF and CBV was replaced by an initial decrease followed by a smaller increase 346. Significant correlations were seen between CBF, CBV, NADH (CF) and ECoG. The intracranial pressure (ICP) levels were significantly higher (around 25 mmHg) in the 2nd cycle (FIG. 4D) as compared to that monitored during the 1st cycle (11-12 mmHg) (FIG. 4C). The down-transient 348 of tissue metabolic score reflects another round of cortical spreading depression. Note the poor recovery of brain activity 350 after this event in the ECoG trace. The slow decline 352 in TMS indicates urgent intervention is needed.

A clinician may diagnose vitality of the tissue such as the brain in a patients hospitalized in the neurosurgical ICU. The results presented in FIGS. 4C and 4D were collected from a patient in coma after severe head injury. The two circled events in FIGS. 4C and 4D show opposite responses in the CBF and NADH measured from the patient that shows a deterioration of the brain after the injury. The tissue metabolic score calculated in the two events is moving in opposite directions, namely, an increase 338 in tissue metabolic score in FIG. 4C and a decrease 348 in the tissue metabolic score in FIG. 4D, suggesting to the clinician that the patient needs specific intervention in order to achieve stabilization and improvement of the blood and or oxygen supply to the brain.

The event shown in FIG. 4C was developed spontaneously due to the damage developed in the injured brain. The change in the response of the tissue metabolic score to CSD shown in FIG. 4D suggested that the brain was in a deteriorating process in terms of the ability to compensate for the extra oxygen needed to return the ionic homeostasis to normal. A transient shift in the tissue metabolic score such as 338 in FIG. 4C that recovers to baseline within few minutes may diagnose a change in oxygen consumption by the brain, but there is no significant damage to the brain. Even if this event may be repeated, but with the same record seen in FIG. 4C, the physician can keep the same treatment to the patient. But if the TMS score is as seen in FIG. 4D (especially the slow decline 352) the physician must be aware that the brain of the patient is deteriorating and he must change the treatment to the patient. This patient deteriorated further and more cycles of CSD were developed spontaneously and were recorded for many hours. The changes in the monitored parameters were similar to the response shown in FIG. 4D.

The results presented in FIGS. 4C and 4D were part of a clinical study approved by the Helsinki committee of the hospital (IRB-Institutional Review Board) Therefore the clinician was not permitted to use the results as a basis for changes in the treatment given to the monitored patient.

However, in future monitored patients, a TMS trace similar to FIGS. 4C and 4D will indicate to the neurosurgeon the need to change the treatment to the patient in order to stabilize the deteriorating brain.

If the TMS is calculated in real time, the aim of the treatment will be to reestablish a normal and positive tissue oxygen balance. Based on animal studies and patient monitoring, it is possible to assume that addition of oxygen supply in similar patients may improve the ability of the brain to use more oxygen for the recovery from the cortical spreading depression-like event. Among the options that might achieve this goal are the following:

1. Keeping the intracranial pressure (ICP) levels in the normal range.
2. Elevation of Oxygen or $CO_2$ in the breathing mixture.
3. Normalizing the systemic hemodynamic parameters, e.g., blood pressure.

II.G. Example 6: A Head Injury Patient

Figure 4E:
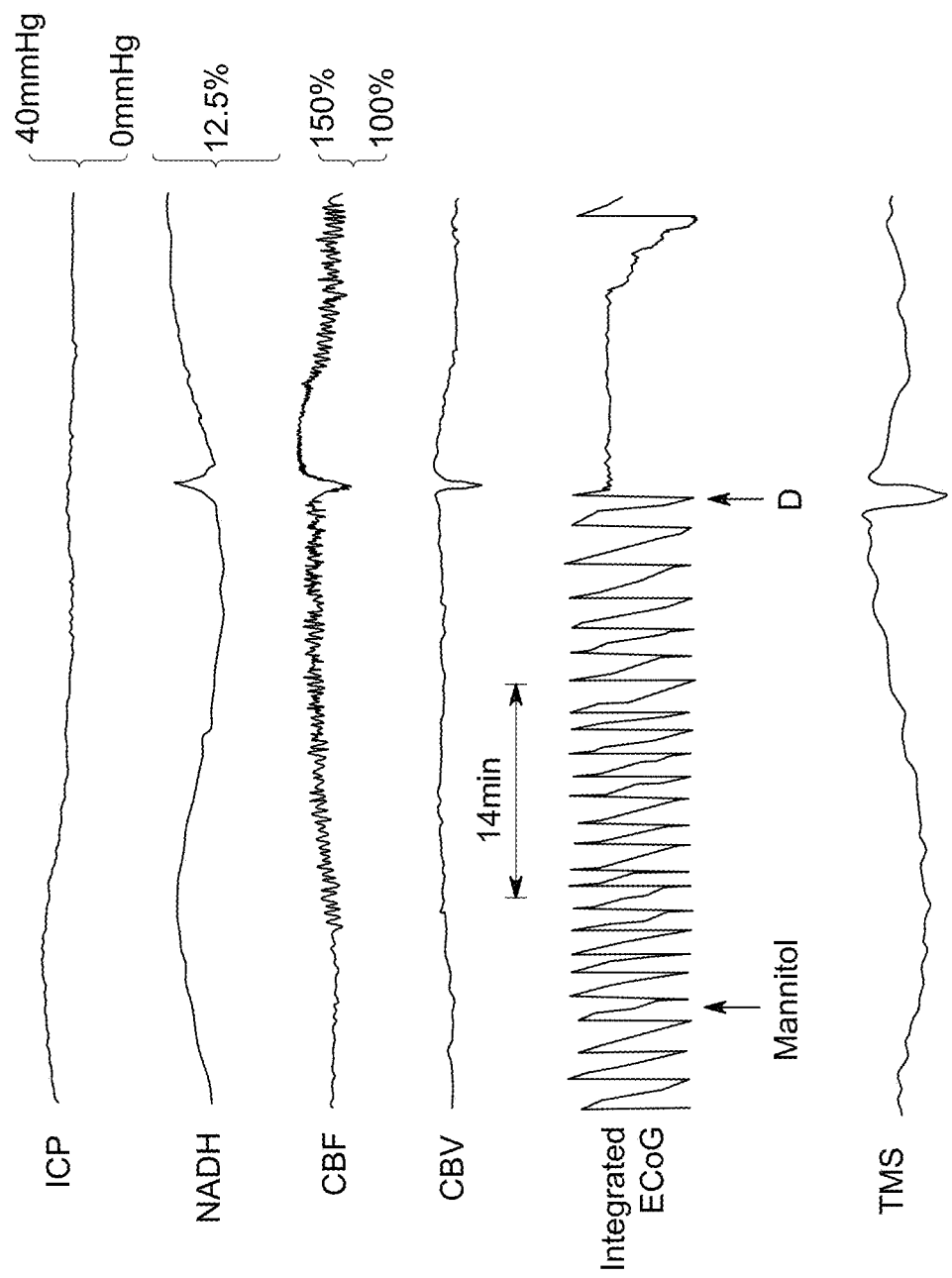

FIG. 4E shows monitoring traces for a head-injury patient, showing effects of IV infusion of mannitol to the patient, on brain hemodynamic, metabolic and ionic activities. In this patient, the intracranial pressure, integrated ECoG, and the parameters underlying the brain tissue metabolic score were monitored. The TMS trace shows that the TMS was initially stable. After 1-2 minutes, the tissue metabolic score began a gentle decline, along with elevation of intracranial pressure. The declining TMS and very high and increasing level of intracranial pressure (30-40 mmHg) indicated the need for intervention. The physician reacted by administering a bolus of mannitol. Promptly the mannitol treatment led to a decrease in intracranial pressure, and shortly after that, an improvement in blood flow, and after that, an improvement to tissue metabolic score. This illustrates the power of TMS as a tool for early alert of a condition, diagnosing the condition (including a differential diagnosis), and recommending treatment options, to save the life of a patient.

About a half hour later (at event D), the TMS showed a large down-transient followed by a slow decrease. While a short down-transient is generally not indicative of patient state, a transient indicates that the following minute or two of any trend in tissue metabolic score is highly likely to be important, and any change in other parameter traces is likewise more likely to be of greater significance. In the point D shown in FIG. 4E, the physician saw that the fast transient change of the TMS was correlated to changes in the other parameters monitored. In this case, the rather rapid fall in TMS following the down-transient, and the disappearance of the ECoG (flat line) and the changes in NADH, CBF and TBV indicate urgent patient distress that could lead to severe deterioration that may lead to brain death later on. In this case, the single most likely interpretation of the single down-transient could be a wave of spontaneous cortical spreading depression, and the slow down-slope following the down-transient strengthens that inference. If the tissue metabolic score and other parameters return to baseline fairly promptly (in the range of 10-30 minutes) the clinician may not have to intervene. Note that the $TMS_B$ begins to recover in about four minutes, and the ECoG begins to show activity a few minutes later. Multiple transient spikes in the TMS continuing for more than thirty minutes may indicate epileptic seizures that could damage the brain, and the clinician may consider treating with anti-epileptic drugs.

II.H. Example 7: Tissue Metabolic Score and Monitoring the Brain

As shown in the previous example, the tissue metabolic score contributed significant information during the treatment given to a neurosurgical patient. The brain as one of the most vital organ in the body should be kept in optimal physiological condition even after development of patho-physiological conditions. The monitoring of the tissue metabolic score provides the most important data regarding the oxygen balance at the microcirculatory and cellular functions. Nevertheless, there are few more parameters that could be monitored in the brain of patients in order to diagnose more accurately the physiological state of the brain. The intracranial pressure (ICP) and the electrical activity (e.g., EEG) are used in many patients in intensive care units (ICUs) and operation rooms (OR). Therefore, in this patent we are suggesting to use a specific scoring system for the brain ($TMS_B$). Using more parameters for the calculation of the score may improve diagnosis of oxygen balance in the brain, and may improve the adequacy of the treatment given to the patient.

TABLE 2

Brain tissue metabolic score (TMSB) under various perturbations or pathological events.

| | NADH | CBF | $HbO_2$ | Reflectance | EEG | ICP | $TMS_B$ |
|---|---|---|---|---|---|---|---|
| 1. Base-line | 100% | 100% | 100% | 100% | 100% | 100% | 100 |
| 2. Anoxia (0% oxygen) | 200% | 140% | 0-5% | 50-60% | 0-5% | 110% | 0-5 |
| 3. Ischemia 50% | 150% | 50% | 50% | 120 | 50% | 90% | 40-50 |
| 4. Ischemia 100% | 200% | 0-3% | 0-5% | 150% | 0-5% | 80% | 0 |
| 5. Spreading Depression | 60-70% | 200% | 110-120% | 80-90% | 5-10% | 100% | 130 |
| 6. Spreading Depression under partial ischemia | 120% | 70% | 90% | 110% | 0-5% | 100% | 80 |
| 7. Hyperoxia 100% $O_2$ | 90% | 90% | 110% | 110% | 100% | 100% | 110 |

Table 2 presents a few calculations of the brain tissue metabolic score ($TMS_B$) in response to perturbations. The advantage of the multiparametric monitoring approach is demonstrated in this table. When comparing perturbation 2 and 4 (anoxia and 100% ischemia), although in both of then oxygen supply is practically around zero, there are large differences in the responses of the various parameters. Nevertheless the $TMS_B$ is about the same. The NADH, $HbO_2$, EEG are the same but CBF, reflectance and ICP are very different due to the perturbations. The calculated tissue metabolic score $TMS_B$ is about the same under the two situations. The $TMS_B$ is a combination of the tissue metabolic score of the brain tissue and other brain specific parameters (EEG, ICP) that increase the evaluation of the functional level of the brain.

Another comparison is between situations 5 and 6 (spreading depression and spreading depression under ischemia) that are very similar to the results recorded from a patient and presented in FIGS. 4C and 4D. Under Cortical Spreading Depression (CSD), oxygen consumption is elevated in the brain (see [Mayevsky2001]) and the $TMS_B$ is elevated from 100 to 130 when oxygen supply is unlimited. The extra oxygen is needed for the maintenance of ionic homeostasis that is disrupted by the depolarization of the neuronal tissue in the brain and the accumulation of potassium in the extracellular space. When CSD is developed under partial ischemic conditions the extra oxygen needed for the recovery phase is not available and therefore the $TMS_B$ is below the normal response.

Table 2 aims to illustrate the possibility to calculate the functional state of the brain based on the tissue metabolic score (four tissue parameters) together with other two parameters (EEG and ICP) that add more information on brain physiology. For example, if we compare state 4 in the table (Ischemia 100%) and state 5 (Spreading Depression), it can be seen that EEG is very low in the two states. But the energy state is completely different If the EEG was the only parameter to be monitored, the clinician will think that the 2 states are the same but as seen the $TMS_B$ is completely different, 0 in state 4 and 130 in state 5.

II.I. Example 8: Monitoring of Two Organs

Figure 5A:
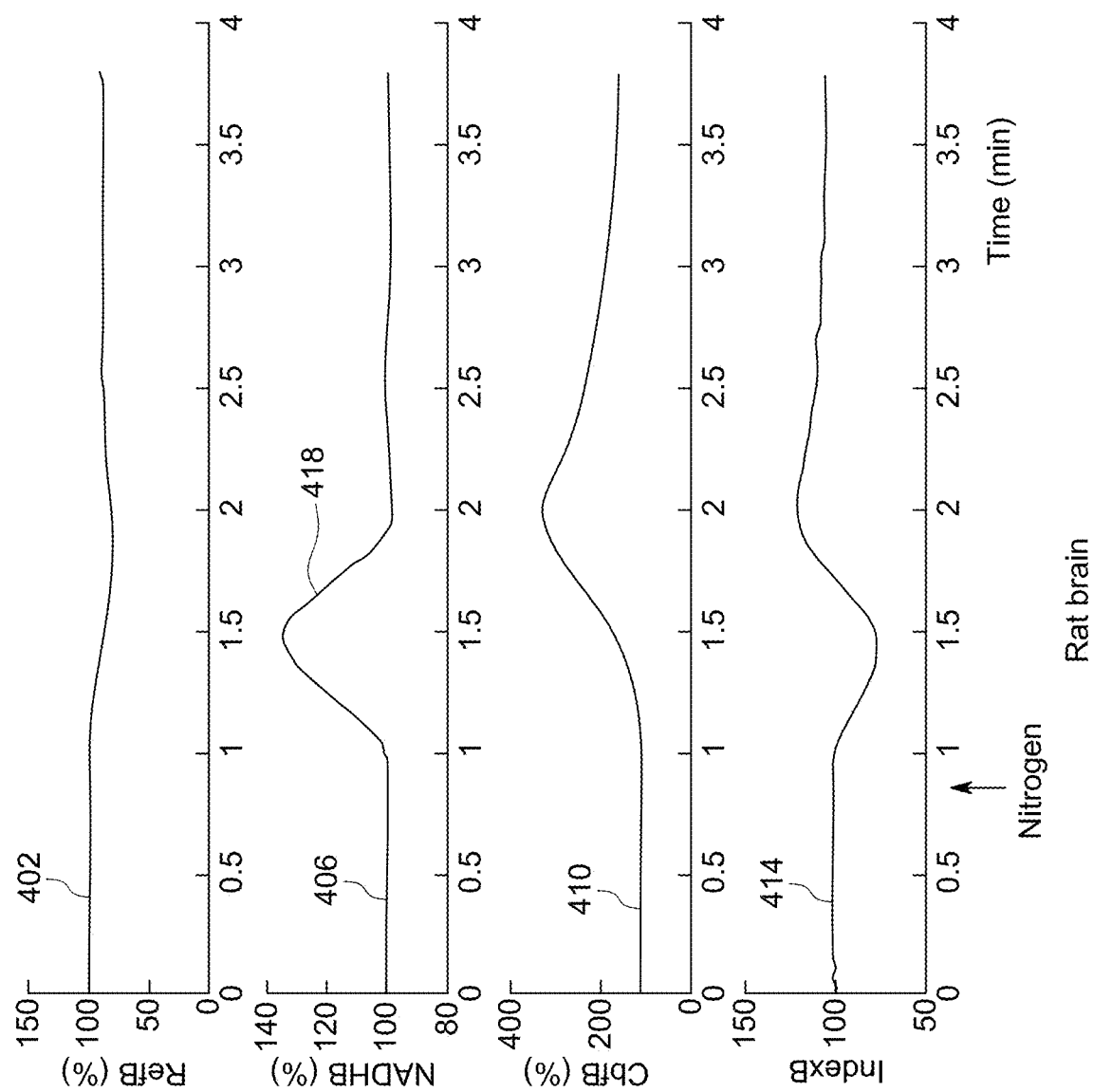
Figure 5B:
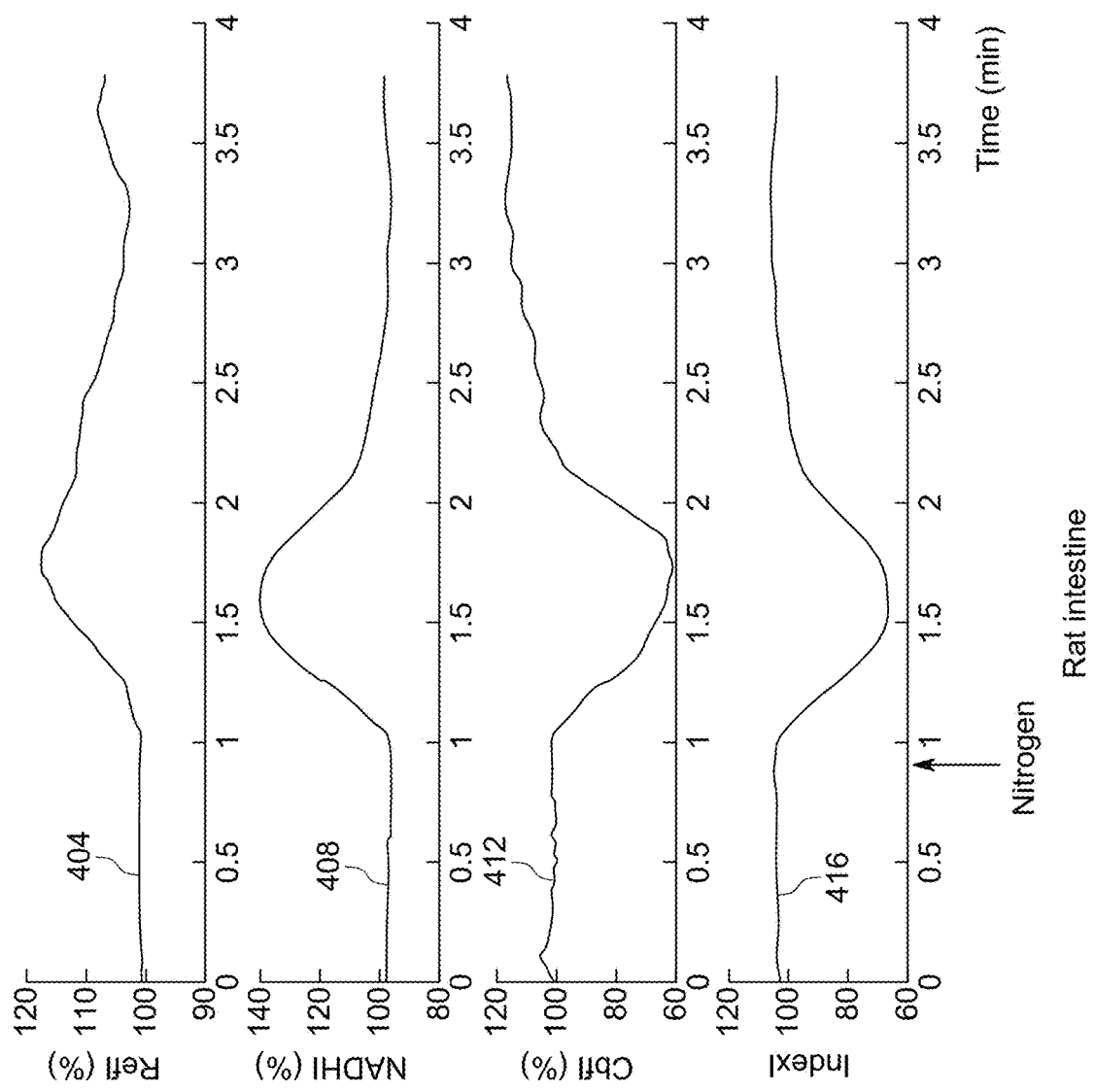

Referring to FIGS. 5A, 5B, 6A, and 6B, the relationship between the responses of various organs in the body to the development of a pathological state may help to establish a powerful tool for diagnosing condition and recommending treatment given to patients. In an animal model, it's easy to monitor one most vital organ (for example, the brain) and one less vital organ (for example, the small intestine). FIGS. 5A and 5B present the monitoring of two organs (the brain and small intestine) in the same experimental animal. In contrast, in human patients, physicians prefer to maintain minimal invasion of the patient's body, and that often leads to monitoring only one organ. Monitoring the urethral wall using a Foley catheter may serve as a surrogate organ to monitoring the brain. On the other hand, it may be desirable to monitor two organs simultaneously as suggested in FIG. 2C box (B) 122. For example, a patient hospitalized in an intensive care unit (for example, the neurosurgical ICU). In this case one probe is located on the surface of the brain (as shown in FIGS. 8B and 8C) and also to monitor the urethral TMS using a Foley catheter.

FIGS. 5A and 5B show responses of brain (FIG. 5A) and small intestine (FIG. 5B) monitored simultaneously in the same rat, under anoxia. The first three traces show reflectance 402, 404 (which correlates to tissue blood volume), NADH fluorescence 406, 408 (which correlates to mitochondrial activity and oxygen balance), and tissue blood flow 410, 412. The fourth trace shows the tissue metabolic score 414, 416. Two types of experiments were performed while monitoring a highly vital organ (brain) and a less vital organ (small intestine), in the same rat. Two types of perturbations were used. In the first protocol, the rat was exposed to maximal depletion of oxygen (breathing pure nitrogen) and the responses of the two organs were very similar indicating that the brain could not protected against the lack of oxygen. In the second protocol, norepinephrine (noradrenaline) was injected intravenously (FIGS. 6A and 6B) in order to induce the blood flow redistribution that protect the brain under conditions of negative oxygen balance.

The data obtained was analyzed in the same computerized system collected the data from the two monitoring device simultaneously. As seen in the record, the changes in the NADH redox state were very similar in the brain 406 and intestine 408 suggesting that the brain was not protected under the complete deprivation of oxygen from the entire body. The blood flow redistribution mechanism was activated as seen in traces 410 and 412 although the blood flow to the brain dramatically increased; oxygen supply was almost zero due to the anoxic conditions maximal increase 418 in NADH. The calculated TMS was very similar in the two organs indicating that the brain was not spared.

Extrapolating FIGS. 5A, 5B, 6A, and 6B from the rat model to a human patient, if a patient in an intensive care unit presented similar monitoring data, the physician can use the TMS traces to diagnose oxygen balance, and made treatment decisions. For example, if the brain and intestine (or urethral) TMS traces both decrease at the same time, the physician should check for a systemic event leading to a body-wide oxygen deficit. For example, simultaneous decrease might indicate a respiratory problem, and appropriate treatment may include artificial respiration. Simultaneous decrease in the brain and urethral TMS scores may indicate fast internal bleeding that results in lack of oxygen throughout the body; in such a case, the physician should locate and stop the bleeding, and provide fresh blood until the TMS traces recover to baseline.

Figure 6A:
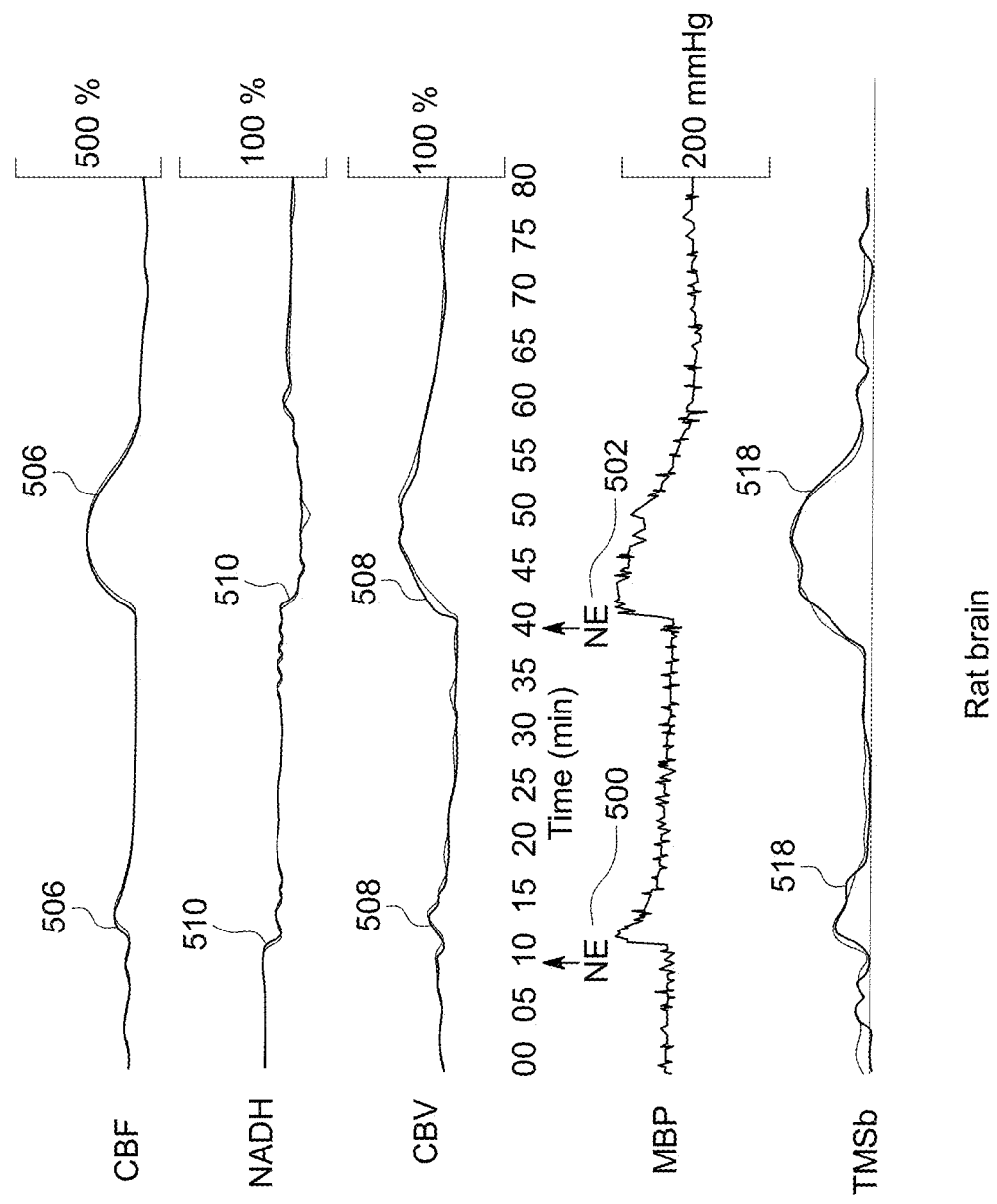
Figure 6B:
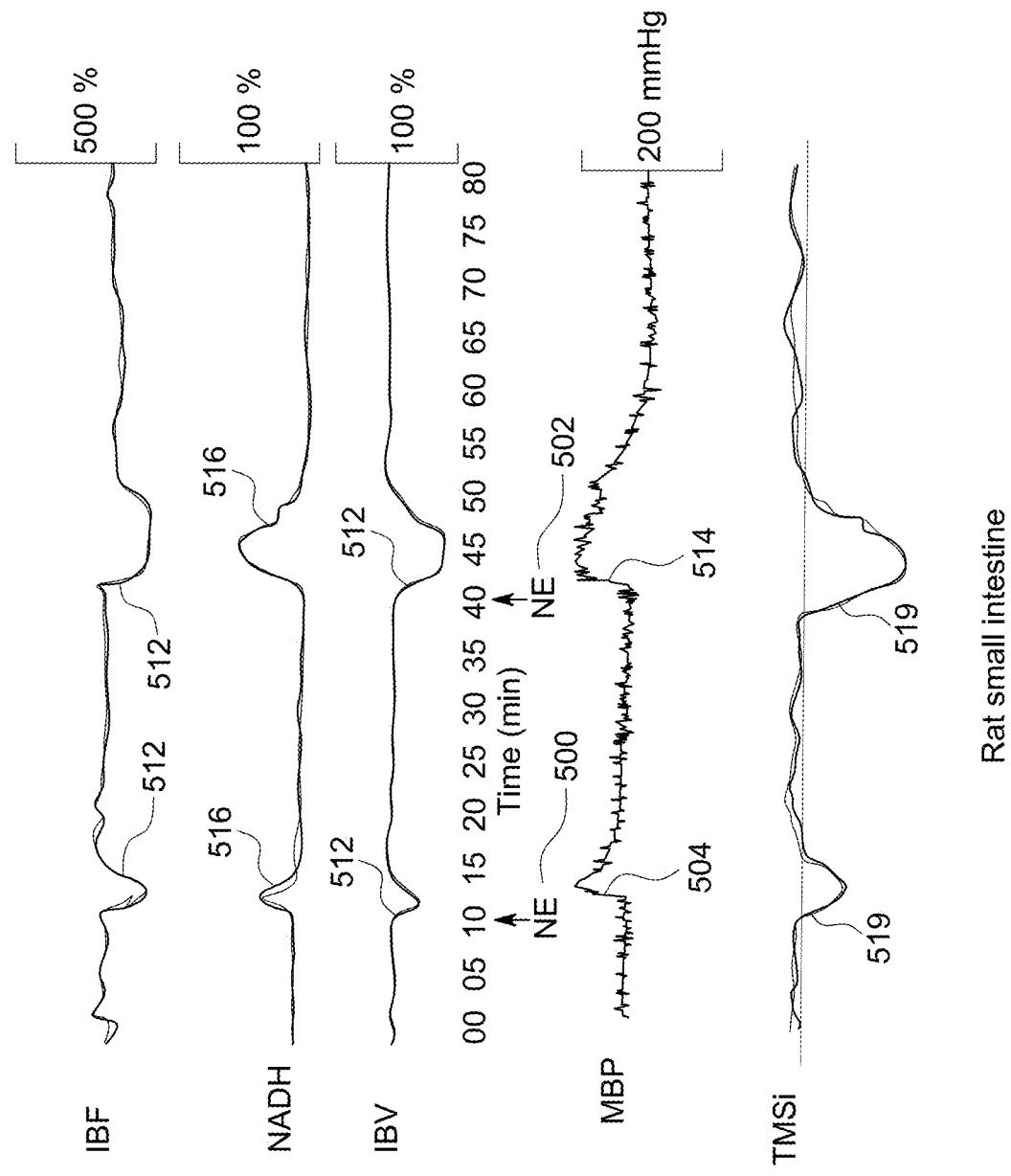

FIGS. 6A and 6B are likewise a simultaneous pair, taken from experiments on a rat model to show the effect of norepinephrine (NE) injected intravenously while monitoring the brain (FIG. 6A) and the small intestine (FIG. 6B) simultaneously. The low dose 500 of norepinephrine that was injected initially (5 micrograms), followed by a higher dose 502 (10 microgram) resulted in significant elevation 504 in blood pressure. The norepinephrine injecting point is the same for the two organs and the blood pressure trace is the same record in FIGS. 6A and 6B. As seen in FIG. 6A, the norepinephrine led to increase in cerebral blood flow (CBF) 506 and volume (CBV) 508 due to the vasodilatation of the small blood vessels in the brain. A clear decrease in NADH redox state (oxidation) 510 was recorded due to the increase in oxygen availability to the mitochondria. In order to protect the brain, the norepinephrine led to the opposite changes in the small intestine namely, a transient ischemic event 512 was recorded, and the blood pressure 514 was elevated. The typical decrease in blood flow during ischemia was recorded together with the inhibition of mitochondrial function (increase in NADH) 516. The TMS show clearly the difference between the brain and the small intestine during the development of the mechanism of blood flow redistribution after norepinephrine injection (stimulation of the sympathetic nervous system).

The example from FIGS. 6A and 6B can be extrapolated to a human patient, for example a patient admitted to an ICU (intensive care unit). For reasons of accessibility, it will generally be easier to monitor a patient's urethra rather than intestine. In such a scenario, the physician may diagnose the total body oxygen balance by observing the TMS measured from the two sites.

In a stable patient, the two TMS signals are stable, indicating that all systemic hemodynamic and respiratory parameters are in the normal range and stable.

A scenario analogous to that shown in FIGS. 6A and 6B, that is, that the brain TMS is increased 518 while the urethral TMS decreased 519, suggests that while the brain currently remains in positive oxygen balance, the decrease in the TMS of the urethra 519 is an early warning signal about total body negative oxygen balance. In this scenario, the physician must act to restore the body oxygen balance to the normal range. Potential interventions include checking the systemic macro circulation status, correcting blood pressure, or increasing the level of oxygen in the breathing mixture.

If both of the two TMS traces show a continuous decrease, this suggests that all internal organs in the body are exposed to severe and probably dangerous negative oxygen balance. The physician should act very fast to check systemic parameters and change the oxygen balance in the body in order to avoid irreversible damage to the patient's brain. Likely interventions include increasing the oxygen supply while checking the systemic oxygenation measured by a pulse oximeter, to make sure that the brain TMS will start a recovery trend toward the baseline value recorded before the emergency situation.

II.J. Example 9: Another Example of Monitoring Two Organs

Figure 7A:
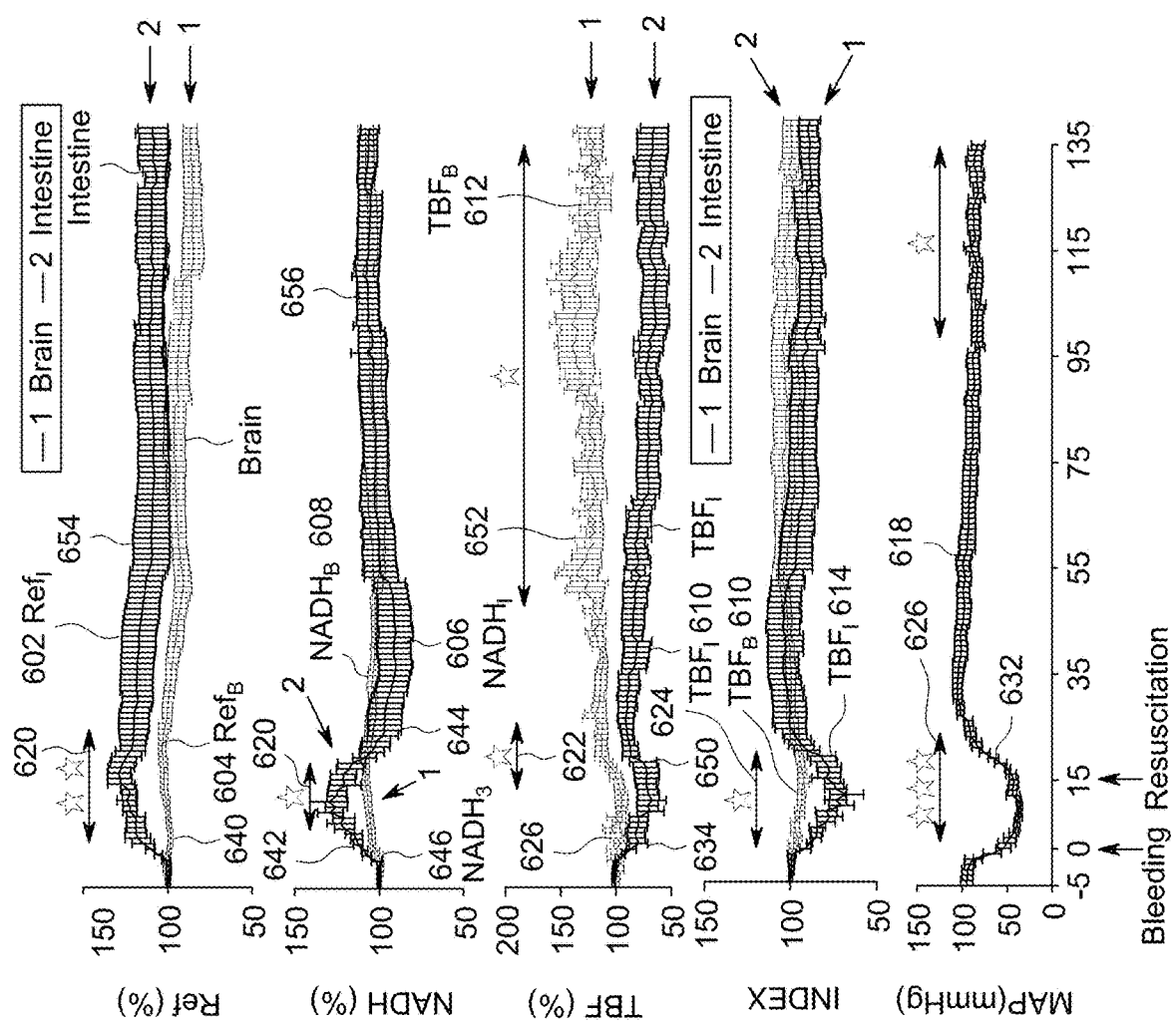
Figure 7B:
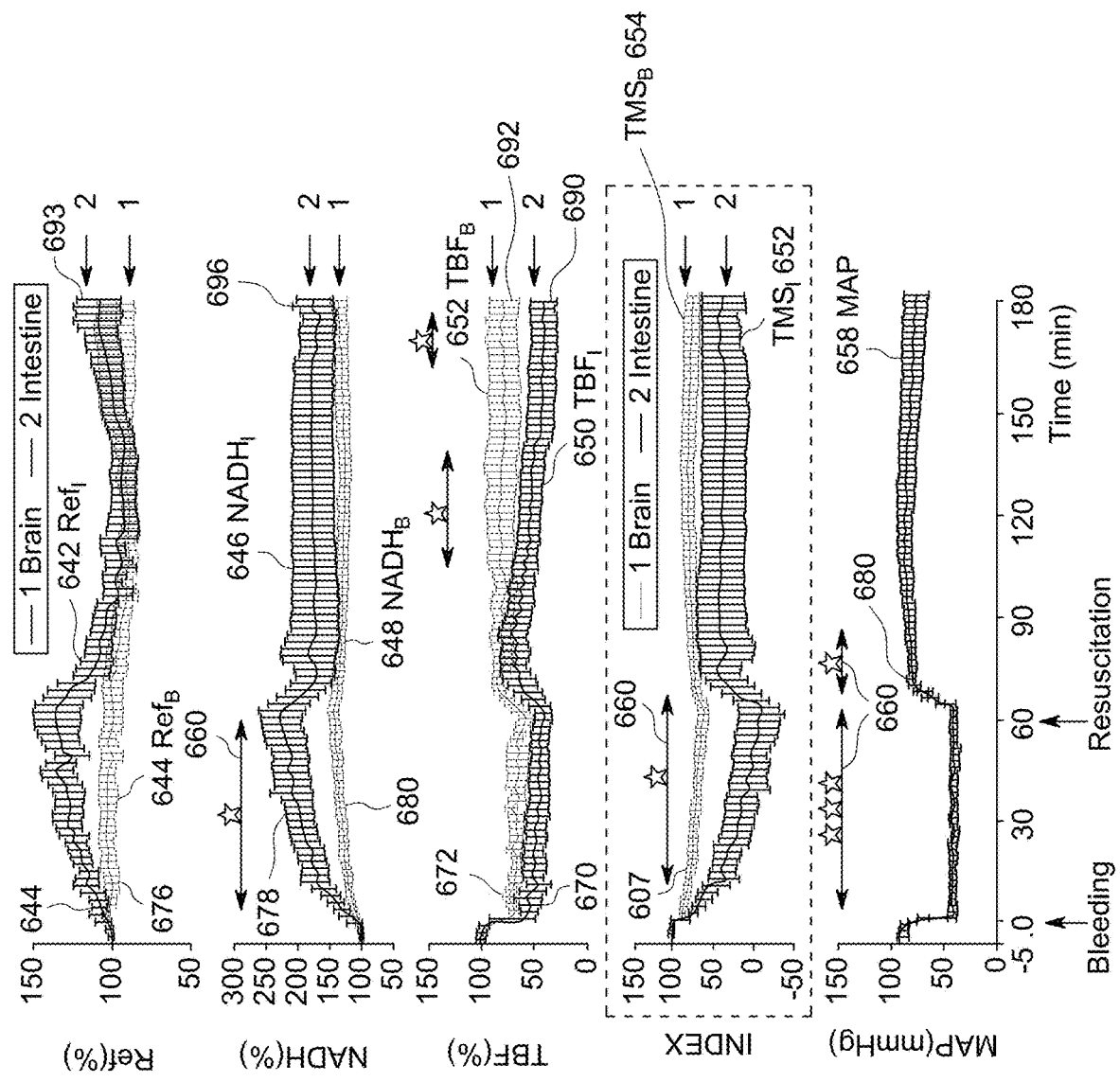

FIGS. 7A and 7B show simultaneous monitoring of a rat's brain and small intestine after a hemorrhage was induced, to show the effect of monitoring two organs simultaneously. The figures show collective responses of nine rats to controlled hypotension, which was maintained for 15 minutes. MAP of 40 mmHg was achieved by an average withdrawal one third of the rats' total blood volume. (n=9, mean±S.E)

FIG. 7A shows nine traces:
Ref$_I$—reflectance, intestine 602
Ref$_B$—reflectance, brain 604
NADH$_I$—mitochondrial NADH redox state, intestine 606
NADH$_B$—mitochondrial NADH redox state, brain 608
TBF$_I$—tissue blood flow, intestine 610
TBF$_B$—tissue blood flow, brain 612
TMS$_I$—tissue metabolic score, intestine 614
TMS$_B$—tissue metabolic score, brain 616
MAP—mean arterial pressure to controlled hypotension for fifteen minutes 618

The arrows 620 represent the period in which significant differences were found between the two organs (in each minute) and the asterisks indicate levels of significance: *$p<0.05$, $p<0.01$ and *$p<0.001$, MAP—mean arterial pressure.

During the hypotension phase, MAP (mean arterial pressure) significantly decreased 632. The intestine and the brain responded differently. Intestinal TBF (tissue blood flow) significantly decreased 634 while the brain TBF remained relatively stable 636, with no significant changes. Intestinal reflectance significantly increased 638 while brain reflectance remained stable 640. Intestinal NADH had two phases: an increase 642 followed by a slight decrease 644 ten minutes after bleeding began. Cerebral NADH increased significantly 646 and was the only parameter in the brain which showed a significant response.

Following resuscitation, TBF in the intestine partially recovered, though about fifty minutes later its levels were again significantly low following a decrease 650, while TBF in the brain increased 652. After resuscitation, intestinal reflectance decreased and gradually returned to its basal level (without significant changes) 654. Cerebral reflectance also decreased gradually with no significant change. Intestinal NADH showed a trend of decrease below the basal level, but then it increased toward the basal value and remained steady for the rest of the experiment 656. Cerebral NADH decreased gradually but with no significant change, except for the resuscitation itself and several minutes afterwards when changes were significant.

The tissue metabolic score of the two organs is presented in FIG. 7A (4th trace from top-Index). A significant difference found between the brain TMS 616 and small intestine TMS during the bleeding interval. The small intestine TMS decreased to a low level 614 while the brain did not suffer from the bleeding and its TMS remained relatively stable 616. In this type of patient, if the brain was the only monitored organ, the physician will not be able to diagnose the real physiological state of the patient since it was stable even though blood pressure was decreased and the patient was bleeding internally. The monitoring of the urethral TMS (in addition to the brain TMS) provide real time information that will be translated into a procedure that will save the patient.

In a patient admitted to the neurosurgical ICU for severe brain surgery, monitoring TMS$_B$ (for the brain) and TMS$_U$ (for the urethra) will allow the physician to identify compromised oxygen flow before it affects the brain, because the compromise will be visible in the TMS$_U$ before it appears in the TMS$_B$. If the monitoring shows TMS$_U$ falling while TMS$_B$ remains steady, the physician should be aware that something in the patient's oxygen delivery or microcirculation system is beginning to fail in less-vital organs, and that compromise to more-vital organs may be imminent. The physician should begin proactive treatment, for example, with transfusion or blood or increasing the oxygen level in the respirator.

FIG. 7B shows the averaged responses to hypotension that was induced by bleeding out about 45% of the rats' total blood volume for 60 minutes (n=7, mean±S.E). FIG. 7B shows nine traces:
Ref$_I$—reflectance, intestine 642
Ref$_B$—reflectance, brain 644
NADH$_I$—mitochondrial NADH redox state, intestine 646
NADH$_B$—mitochondrial NADH redox state, brain 648
TBF$_I$—tissue blood flow, intestine 650
TBF$_B$—tissue blood flow, brain 652
TMS$_I$—tissue metabolic score, intestine 654
TMS$_B$—tissue metabolic score, brain 656
MAP—mean arterial pressure to controlled hypotension for fifteen minutes 658

The arrows 660 represent the period in which significant differences were found between the two organs and the asterisks represent significance levels: *$p<0.05$, $p<0.01$ and *$p<0.001$.

During bleeding, the TBF of the brain and intestine decreased rapidly and stabilized at low levels. However, while intestinal blood flow significantly decreased 670 by 61%, cerebral blood flow significantly decreased 672 only by 45%. Intestinal reflectance showed a trend of increase 674, while the cerebral reflectance 676 increased by 5% and decreased back to its basal level. In comparison to the intestinal NADH, which slowly increased 678 up to 228%, cerebral NADH increased 680 only to a level of 142%. The maximum levels of NADH in both organs were monitored at the end of the hemorrhagic period and were also associated with the maximum changes in TBF.

Following resuscitation, MAP increased up to basal level 690. The intestine and the brain responded differently to resuscitation. Intestinal blood flow significantly increased by 30% reaching a level of 69% followed by a secondary decrease down to 37% 691. Blood flow in the brain increased by 7A. 0.5% and stabilized at a level of 82% 682. The intestinal reflectance decreased sharply below its basal level, followed by an increase back to the basal levels 693.

Cerebral reflectance showed nearly no changes except for a decrease of 12% during a short period about an hour after resuscitation. Following resuscitation, NADH in both organs only partially recovered and remained elevated 691 compared to the basal level.

When the two organs are compared during bleeding, a significant difference is observed only with respect to NADH levels 646, 648. Following resuscitation, there were only two episodes of significant differences in the TBF between the organs.

The tissue metabolic score of the two organs was calculated and is presented in FIG. 7B 652, 654. A significant difference found between the brain and small intestine during the bleeding interval. The brain kept its vitality close to normal 692 while the vitality of the intestine decreased significantly 693 relatives to the control and recovery periods. These results demonstrate the ability of the organism to protect the oxygen balance homeostasis of the most vital organ, the brain.

The difference between the changes in the tissue metabolic score between the brain (most vital organ) and the intestine (less vital organ) may be applied in clinical situations. For example, in a patient undergoing major abdominal surgery (e.g., removal of a major part of the large intestine), a urethral sensor in a Foley catheter (see section II.Q) may be used to monitor the vitality of the urethral wall (less vital organ, similar to the small intestine shown in FIG. 7B). At the end of the operation the patient is normally transferred to the ICU for twelve to twenty-four hours for recovery. Suppose that, during the postoperative period, a small bleeding starts in the operated region of the intestine. This slow but gradual bleeding will not be initially detected by the current hemodynamic parameters (vital signs) due to the mechanism of blood flow redistribution (described in section I in connection with FIG. 2E), and therefore, the systemic blood pressure and blood flow to the heart and the brain will be kept in the normal range. At the same time the less vital organs such as the urethral wall will be hypoperfused and a decrease in the tissue metabolic score will be detected by the urethral sensor. The conclusion from this type of study is that real time monitoring of a less vital organ could provide an early warning signal regarding the development of a negative oxygen balance in a patient and may enable the clinician to take measures that will keep the patient in physiological normal range. The presentation of the TMS in real time to the clinician is significantly better than observing the four signals on the screen of the monitoring device.

This early warning sign will raise an alert well before the brain begins to suffer from decreased blood supply as long as the bleeding continues. This type of monitoring will save many lives as well as decrease the damage developed in the brain. Therefore, even one monitoring site in the urethral wall, and computing tissue metabolic score, may be very significant in the patient's care.

Figure 8A:
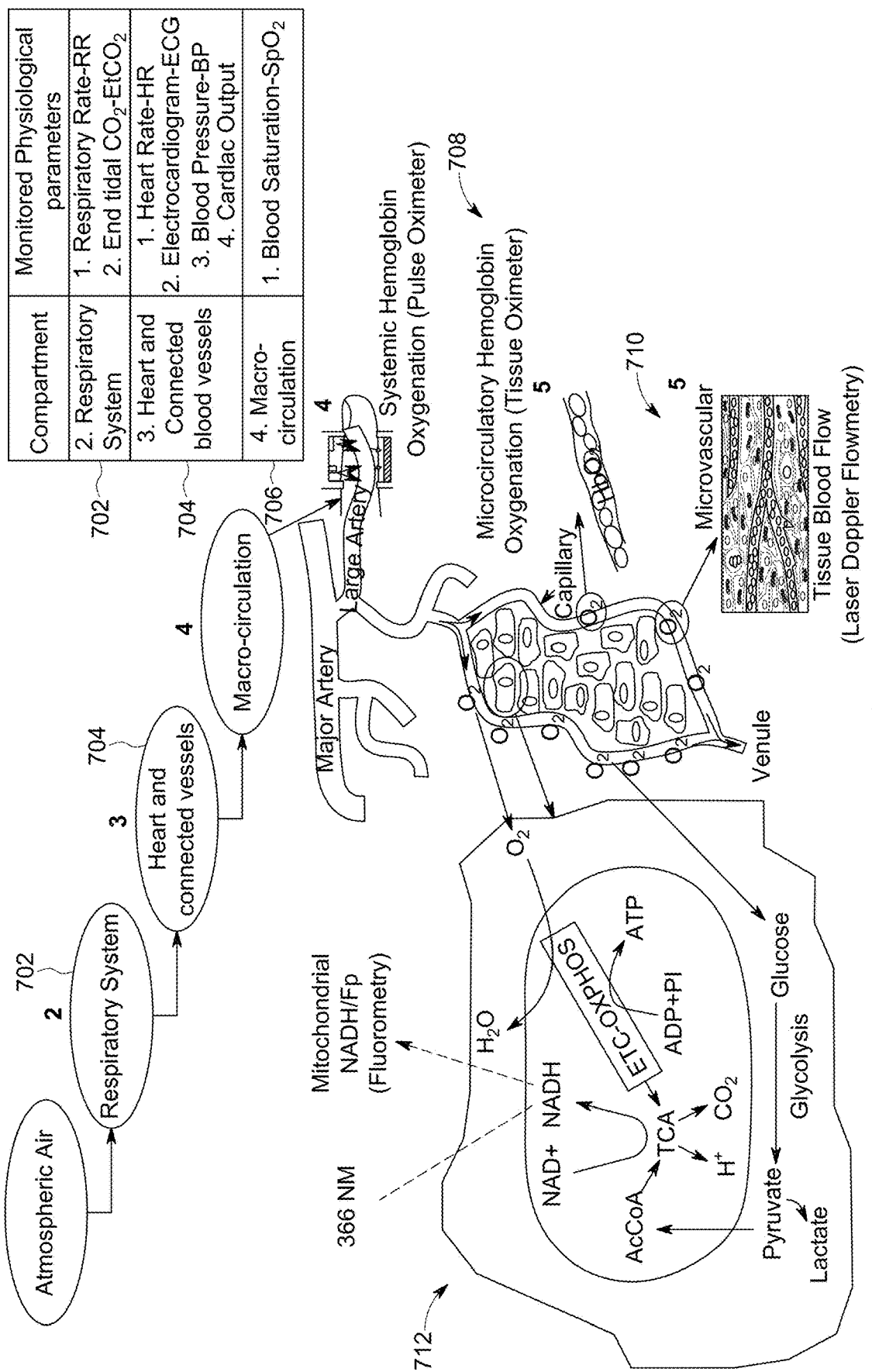
FIGS. 8A, 8E, 9D, and 10B are schematic diagrams showing relationships between oxygen flow and level, tissue function, light absorbance, and light reflectance.

II.K. Example 10: Monitoring Urethral and Brain Metabolic Scores Together with Systemic Parameters Referring again to FIG. 2C, patient care may be improved if a patient is monitored for traditional vital signs (temperature, pulse rate, respiratory rate, and blood pressure) and physiological systemic parameters, in combination with organ-specific parameters, such as those measured in an operating room or intensive care unit during a procedure for a specific organ, and the parameters used to calculate the TMS of a specific organ of interest (for example, the brain), and the parameters used to calculate the TMS for a less vital organ (the kidney and/or urethra). FIG. 8A presents this type of combined monitoring between the macro circulation (in the respiratory system 702, the heart and connected vessels 704, and macro-circulation 706) and the microcirculation 708, 710, and the cellular compartment (including the mitochondria 712). The table of FIG. 8A lists the physiological parameters that may be monitored at points 702, 704 and 706. In less severe pathological state of patients, it may be adequate to monitor only the urethra TMS and systemic parameters, all of which can be monitored non-invasively (with at most a Foley catheter), and from these the flowing indices or scores may be calculated in real time:

1. Brain tissue metabolic score ($TMS_B$)
2. Urethra tissue metabolic score ($TMS_U$)
3. Systemic Vital Signs Score (SVSS)

The combination of these three scores may be useful to a physician to diagnose the physiological state of the patient (and a specific tissue that is being monitored especially closely) and determine a treatment approach.

In patients with brain indications (for example, a transient mini stroke), it may be useful to monitor both the brain tissue metabolic score ($TMS_B$) and urethral tissue metabolic score ($TMS_U$) together with indicators of the macro circulation and the respiratory function (body temperature, pulse rate, respiration rate, blood pressure, etc.—the systemic vital signs score). If the ischemic event was very small and transient, it's expected that the systemic vital signs will stay in the normal range. If the $TMS_U$ remains stable while the $TMS_B$ either improves (indicating that oxygen balance in the brain is improving) or $TMS_B$ declines (typically a local ischemia), the physician should concentrate his effort to check a possible reason developed in the brain tissue. In this case the problem is likely not a systemic problem in body oxygen balance but rather local event in the brain. If the $TMS_U$ declines while the $TMS_B$ remains stable, the physician should analyze and correct systemic vital signs parameters, as directed by the systemic vital signs score, in order to recover body oxygen balance. This may call for an increase in the level of oxygen in the respiration system, or an infusion of blood in order to increase the hematocrit level and reach a better systemic oxygenation.

II.L. Example 11: Neurosurgical Patients

Figure 8C:
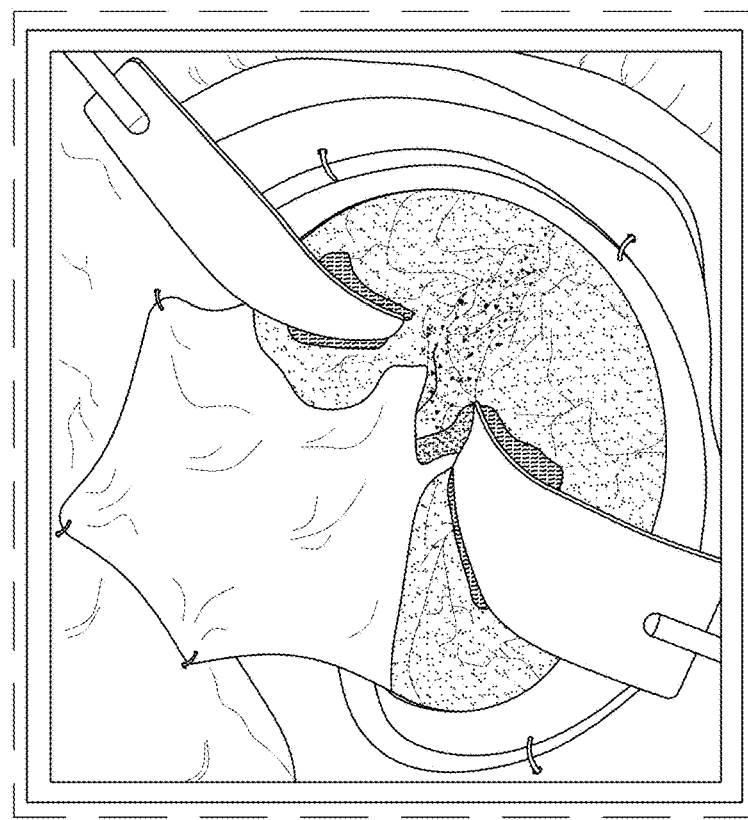
FIGS. 8B, 8C, 10C, and 10D are drawings of monitoring probes.
Figure 8B:
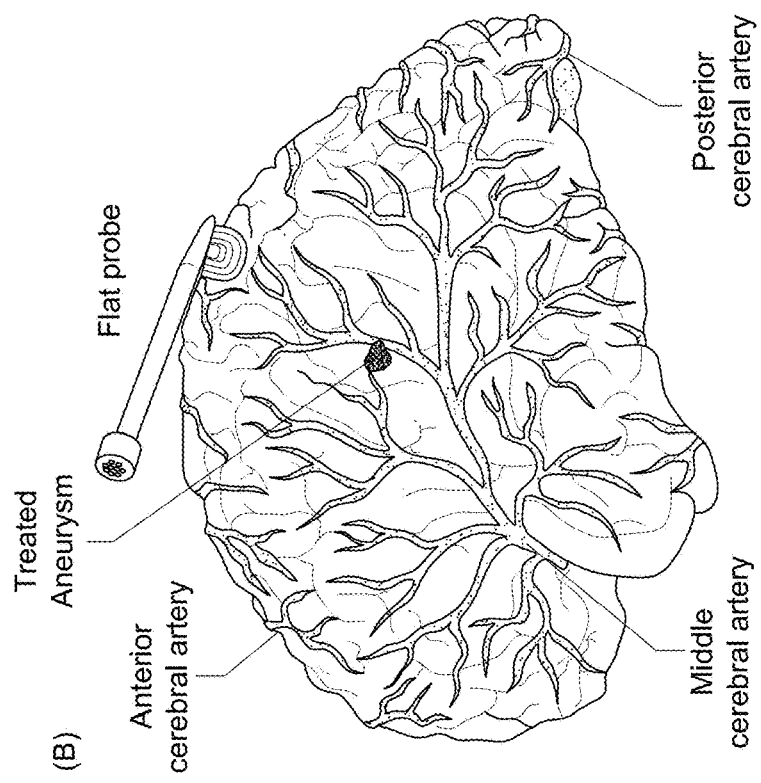

Referring to FIGS. 8B and 8C, in neurosurgical patients, it is important to determine the oxygen balance during surgery in order to avoid the development of ischemia under the retractor or during treatment of an aneurysm. The results of this monitoring originate from and reflect the very local part of the brain.

FIG. 8B shows an operation for an aneurysm or other need for by-pass surgery of the brain. Here again, the use of the tissue metabolic score during the operation could provide a fast indication showing the efficacy of the surgical procedure after the manipulation of the blood vessel but before closing the operated area and ending the procedure. By monitoring the tissue metabolic score in the area distal to the treated aneurysm, the clinician will be able to avoid an ischemic event due to the surgical procedure. If a decrease in the tissue metabolic score is noted in tissue distal to the aneurism, the physician should change the position of the clip placed on the artery to avoid ischemia.

FIG. 8C shows conventional use of a conventional retractor during brain surgery. The retractor creates pressure on the tissue and as a result, blood flow and oxygen supply will decrease and the brain will suffer from ischemia. The level of retraction as well as the duration will determine level of ischemia and its reversibility. Calculation of the tissue metabolic score may provide a real time indicator of the level of ischemia developed by the retractor. A four-parameter tissue metabolic score based on NADH fluorescence, reflectance, tissue blood flow, and tissue hemoglobin oxygenation may be especially advantageous. If the tissue metabolic score reaches a critical ischemic level, the surgeon should release the retraction, and wait a few minutes for recovery before again using the retractor. The maximum permissible ischemic level created by a retractor may be established after monitoring of a large group of patients and correlating the results to the tissue metabolic score values.

II.M. Example 12: Diagnosing Brain Death for an Organ Donor

Before organs can be harvested from a donor, the donor patient must reach a state of "brain death" determined by various criteria. Determining whether a critically ill patient (for example, a patient admitted after head trauma) will live or die, early enough to prevent deterioration of transplantable organs, may be improved using the tissue metabolic score. The determination of brain death should be performed as early as possible in order to start the process of organ donation and get an organ in better physiological situation that will increase the successful rate of the transplantation procedure.

A critical patient is typically monitored for standard systemic parameters listed in FIG. 8A and FIG. 2C, and in the case of head trauma, for EEG and ICP (intracranial pressure) from the brain as described in Example 6 (discussing FIG. 4E). In addition, a critical patient may be monitored for microcirculation and mitochondrial function in the brain as well as in the urethral wall using a Foley catheter, and all parameters together may give a more detailed view of the physiological state of the brain. The monitoring of this type of patient could provide direct information on the tissue metabolic score in the brain ($TMS_B$) as well as in the urethral wall ($TMS_U$).

In such a patient, three sets of data may be collected in real time namely, $TMS_B$, $TMS_U$ and systemic vital parameters. Since this type of patient is intubated and connected to a respirator, there is a good chance the systemic physiology will not be the first system to deteriorate. Also, the urethral TMS may be in the normal range as long as the systemic oxygenation remains in the normal range. It's expected that the tissue metabolic score of the urethra $TMS_U$ may often be the first indicator of patient deterioration.

In this case, the body as a system is in the normal physiological range as indicated by the $TMS_U$ and systemic parameters. The event in the brain developed earlier in this case since we are monitoring the cortex of the brain that may respond before the brain stem area. The systemic parameters will respond later since they represent the brain stem that is controlling the cardiovascular and respiratory regulatory centers of the body. Under those conditions, it will be critical to follow the state of the brain and when the $TMS_B$ reaches a low level (according to "big data" analysis) it will be important to closely follow the urethral $TMS_U$ and the vital signs behavior.

In current practice, "death" and availability of organs for harvesting is determined in different ways in different jurisdictions. One test is to disconnect the patient from all artificial respiration assistance, and observe whether the patient continues breathing autonomously, which indicates whether the respiratory centers of the brain are still alive. Another test is to inject a drug (such as dopamine) that stimulates the cardiac centers of the brain, and observe the effect on heart rate. Because the cardiac and respiratory centers of the brain are among the most conserved parts of the body, when they have shut down, there is no possibility whatsoever of the patient recovering. However, it may be possible to monitor the brain using $TMS_B$ techniques, thereby permitting death to be determined at some earlier point. This may permit organ harvesting earlier, which allows the organs to be obtained in better condition, and may provide critical minutes if the recipient patient is in an emergency state.

II.N. Example 13: Organ Transplants in the Recipient

Another example is the monitoring of oxygen balance in the kidney during organ transplantation procedure. After donation, a donated kidney is inactive and kept at low temperature before the transplantation and therefore must be tested for its integrity. In current practice, recovery of the transplanted kidney is evaluated based on the detection of urine formation, which takes time.

The tissue metabolic score may provide earlier information—tens of seconds, rather than hours (often after the operated area in the patient is closed). After implantation of a transplanted kidney and the reflow of blood into the organ in the recipient patient, integrity of the kidney may be evaluated via the tissue metabolic score, based on microcirculation and the mitochondrial function. A probe similar to the one shown in FIG. 8B may be placed on the exposed surface of the kidney before the reperfusion of the kidney after the surgery. Alternatively, the tissue metabolic score of the transplanted kidney may be evaluated based on a small needle probe inserted for a period of 24-48 hours postoperatively. Once the surgeon opens the renal artery, the tissue metabolic score of the kidney should detect blood in the microcirculation and the mitochondria using oxygen. A low value of the tissue metabolic score may indicate either a lack of microcirculation blood flow or lack of mitochondrial activity. This low value may prompt the surgeon to act, for example, by placing a vasodilator drug (such as papaverine) on the renal artery, to reestablish kidney blood flow, which in turn reestablishes oxidation of the mitochondrial NADH.

Figure 8D:
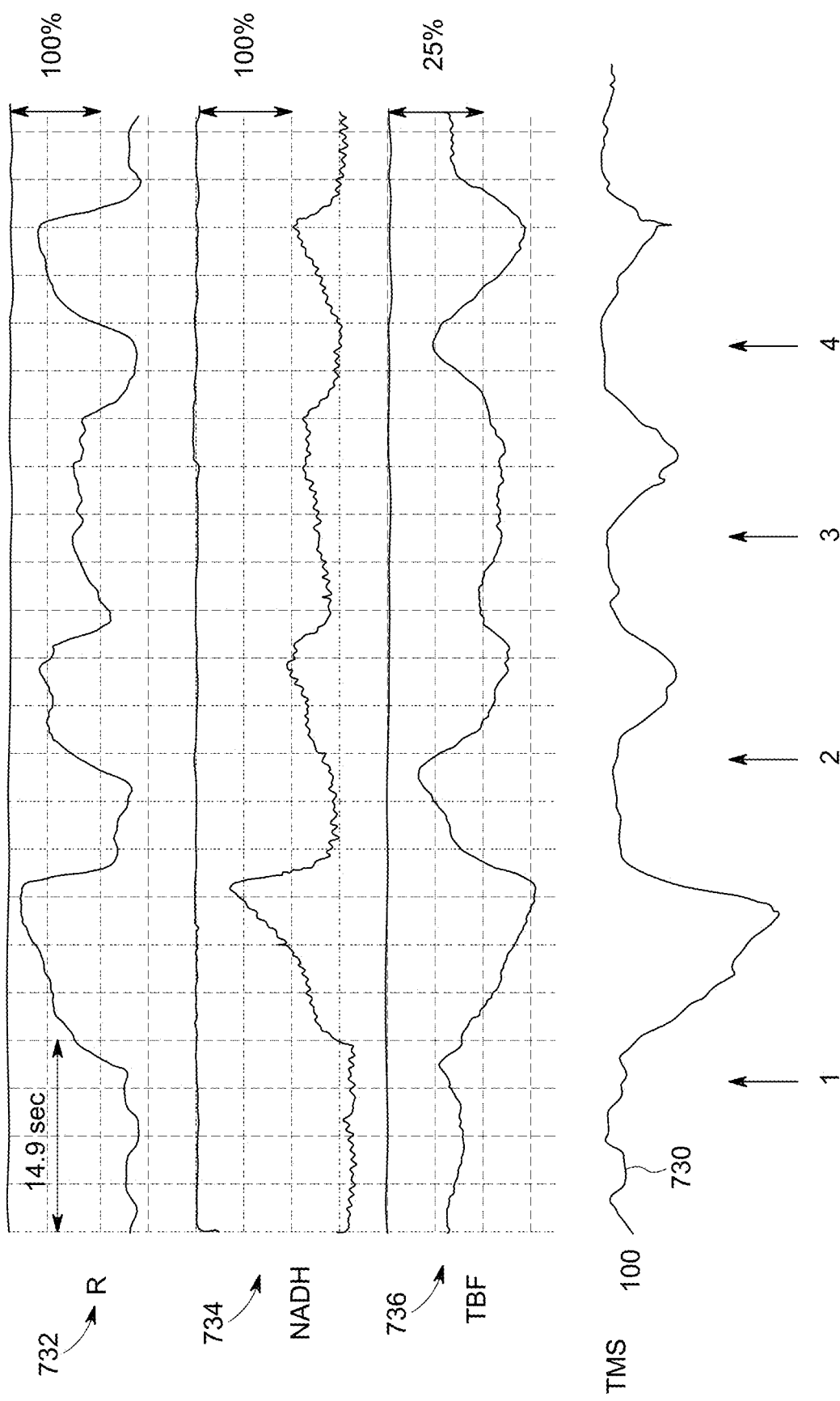

FIG. 8D presents the recording of kidney during the reperfusion stage after the surgical procedure. The fourth trace 730 is the tissue metabolic score computed from the R 732, NADH fluorescence 734, and TBF 736 traces. The four events 1-4 shown in FIG. 8D represent responses of the kidney to mechanical pressure imposed on the kidney by the surgeon during the last stage of the surgical procedure. For example, event 1 was occlusion of renal blood flow, for example, by finger pressure to block the renal artery. FIG. 8D shows that the tissue metabolic score decreased due to disturbance in the blood flow to the tissue and the decrease in oxygen supply. That response in tissue metabolic score indicates that the kidney has good viability after the transplantation procedure. If the tissue metabolic score doe not respond to mechanical pressure or a short occlusion of the renal artery, the physician should investigate whether the viability of the kidney is very low and therefore blood flow is not providing enough oxygen to keep the mitochondria in an active state, and whether further intervention is warranted before closing.

The real time evaluation of the tissue metabolic score of the kidney, during the procedure, should increase the successfulness of the transplantation procedure and to decrease the rejection rate of organs in the recipient patients.

In the same type of patients described in the previous paragraph, it may be advantageous to measure, in addition to the kidney, the tissue metabolic score of the urethral wall (FIG. 2C box (B) 122 (2) by monitoring the four parameters using a three-way Foley catheter, and computing the tissue metabolic score in real time. This additional monitoring may provide an early warning signal to a possible deterioration of the patient during the post-operative period after the transplantation. This may happen even when the kidney was well functioning in the patient but other pathologies were developed in the body.

II.O. Example 14: Trauma Patient with Blood Loss

A patient was admitted to an intensive care unit after severe car accident during which the patient lost a major part of his blood volume. In order to save the life of this patient, it is necessary to diagnose his body oxygen balance in real time. Monitoring of the urethra wall oxygen balance, using the tissue metabolic score, will provide an early warning signal of the entire body metabolic state and its response to the treatment given, e.g., blood or saline transfusion. Any additional information provided by the other monitoring devices (FIG. 2C box (C)(a) 126 and/or (C)(b) 128) may increase diagnostic specificity and efficacy of the treatment given to the patient. Thus, based on initial monitoring of the patient on admission to the ICU, the tissue metabolic score may be computed from the measured parameters, and set to an initial relative value (e.g., 100). In order to provide more oxygen to the patient, infusion of blood (for example, an initial infusion of 400 ml) may be started and it is expected that the tissue metabolic score will gradually increase, for example, to a level of 120. If this amount of blood is enough then additional blood infusion will not improve the tissue metabolic score any more so a steady level was reached. Under those steady state conditions, the clinician may replace the addition of blood by regular physiological saline infusion and continue to monitor the tissue metabolic score.

II.P. Example 15: Regenerative Medicine

Regenerative medicine may provide regeneration of tissues or organs for functional repair of human tissue damaged by disease or injury. Transplanted cells may be integrated into damaged tissue, damaged structures may be replaced with new tissues and organs generated ex vivo, or damaged structures may be regenerated by recruiting endogenous repair mechanisms in vivo. The tissue metabolic score may be useful to advance regenerative medicine therapeutic approaches and tissue engineering.

Tissue engineering may encompass a variety of tools and approaches, ranging from developing synthetic or bioengineered scaffolds that recruit or enhance the body's natural repair processes, to optimizing transplantation with products that direct the migration and integration of cells into damaged tissue, to creating three-dimensional tissues seeded with cells and built in vitro.

Tissue engineered products may be tested for safety and efficacy before they are advanced to the clinic. This may include methods for real-time, non-destructive, high-content assessment of the health and stability of an engineered tissue either in vitro or in vivo. The tissue metabolic score may provide analytical techniques to monitor successful engraftment and function of engineered tissues, and to evaluate host responses to the implant including inflammation, apoptosis, cell trafficking and gene expression. Parameters measured for incorporation into a tissue metabolic score might include data from intelligent nano sensors, which can non-invasively sense particular chemical signals indicative of their respective cellular events, into engineered tissues to monitor tissue behavior.

The function of the human body is dependent on a continuous supply of oxygen from the atmospheric air, through the respiratory system, through the macrocirculatory system (the blood vessels) with a gradient of saturation from the lungs to the extremities, through the microcirculation (the capillaries and diffusion across the walls of capillaries and cell membranes) into the intracellular mitochondria.

Tissue engineering depends on providing enough oxygen in tissues thicker than 150-200 microns. Viability of constructed tissues or organs may be improved by monitoring of vascularization using NADH fluorescence techniques and the tissue metabolic score, to ensure proper oxygen metabolism in engineered tissues or organs.

Figure 8E:
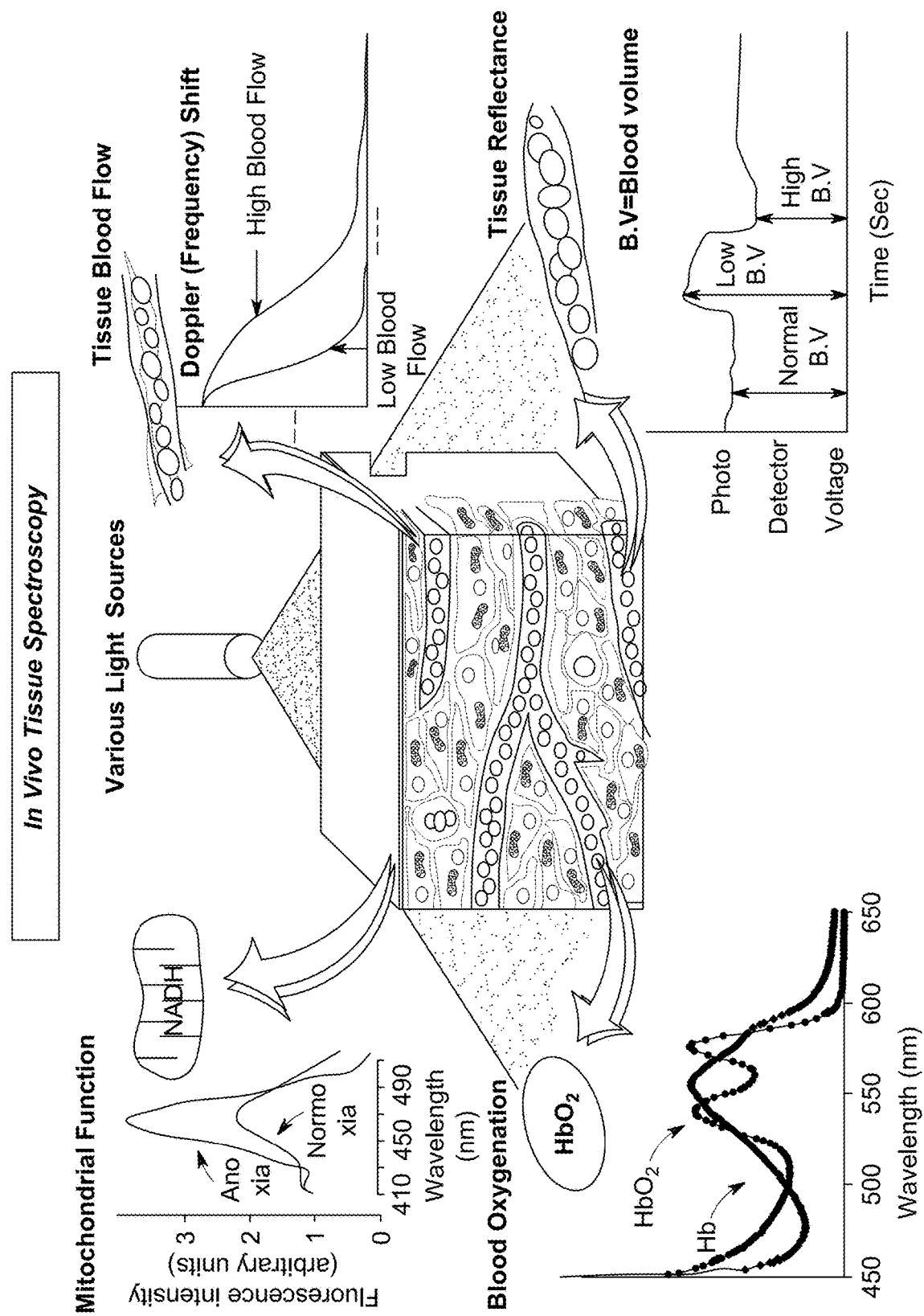

Referring to FIG. 8E, for in vivo monitoring of microcirculation, probes may monitor tissue blood flow, blood volume and hemoglobin oxygenation, and NADH/Fp autofluorescence, and potentially other parameters. Reflectance may also be measured in order to eliminate possible artifacts that may distort the emitted fluorescence signals. Mitochondrial redox state may be computed from these parameters. The tissue metabolic score may be used for quality assurance of tissue engineering in production of tissues and organs to be used in patients.

Figure 9A:
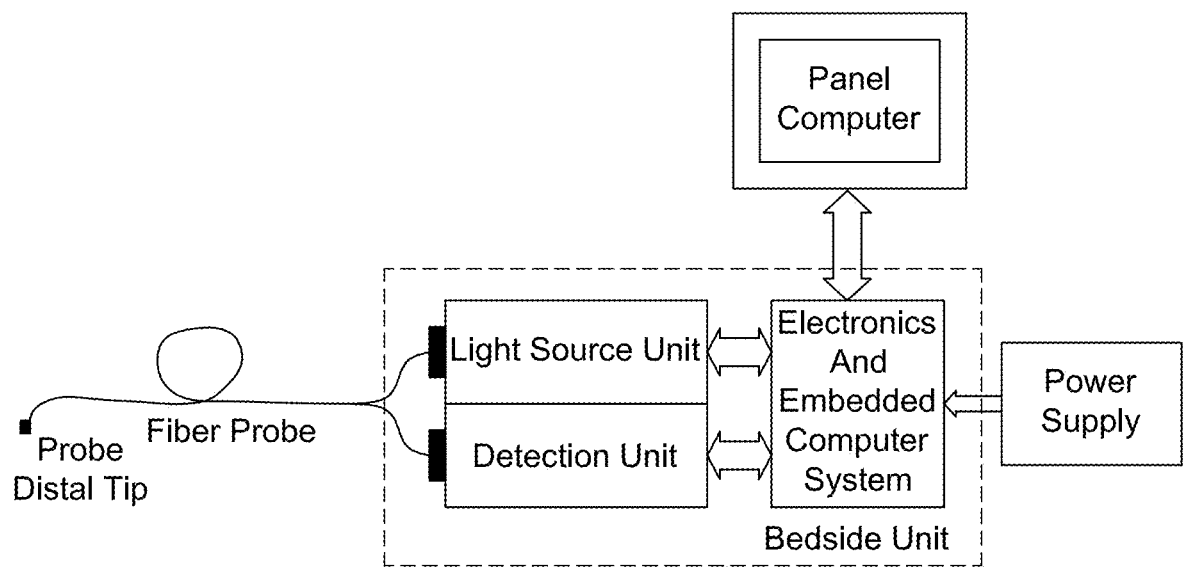
FIGS. 9A, 10A and 10G are schematic diagrams of devices for tissue monitoring and computation of metabolic score.
Figure 9B:
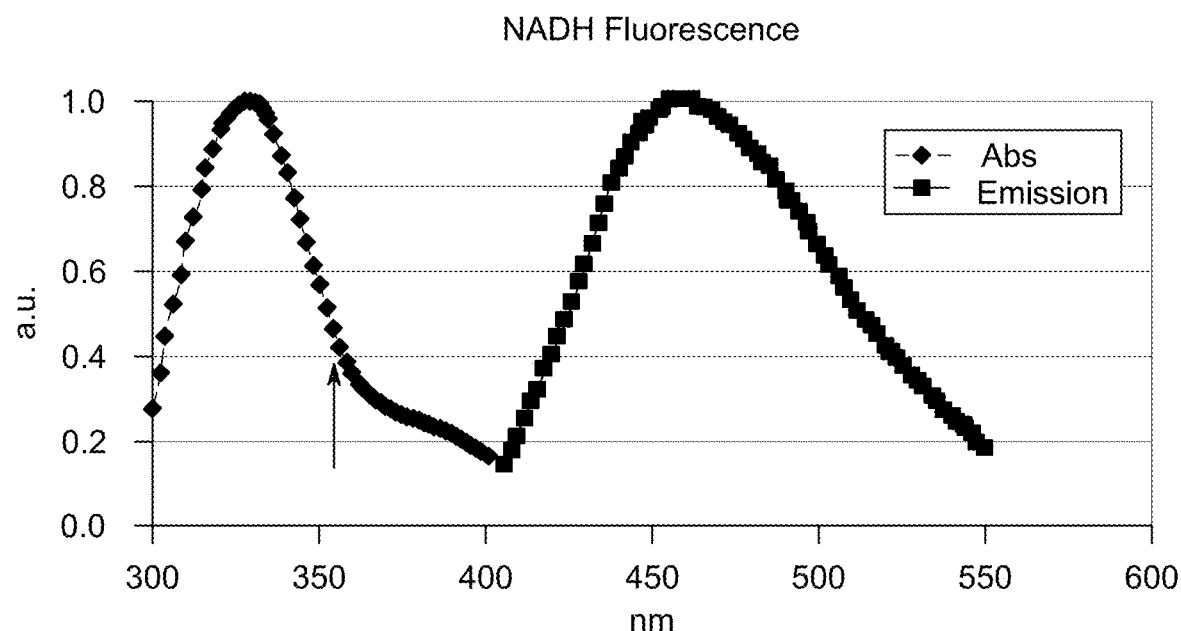
Figure 9C:
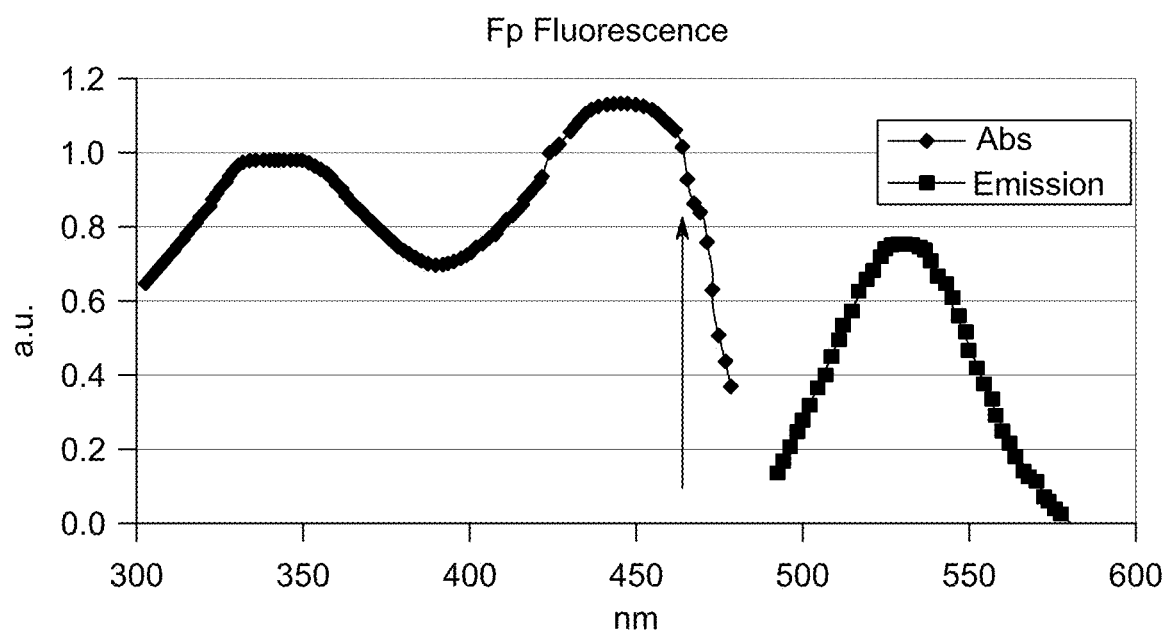

Referring to FIGS. 8E, 9B, and 9C, a first model of probe/monitor may monitor mitochondrial function by measuring the redox state of NADH alone and afterward together with the fluorescence of the Flavo-proteins (Fp) located in the inner membrane of the mitochondria. Tissue reflectance may be measured together with the two fluorescence signals in order to obtain the net fluorescence change. This first model may provide real time information on mitochondrial function evaluated by the redox state of two components that are part of the respiratory chain. The device may measure the fluorescence of nicotine amide di nucleotides (NADH) and Flavo-proteins (Fp) located in the inner membrane of the mitochondria.

Figure 9D:
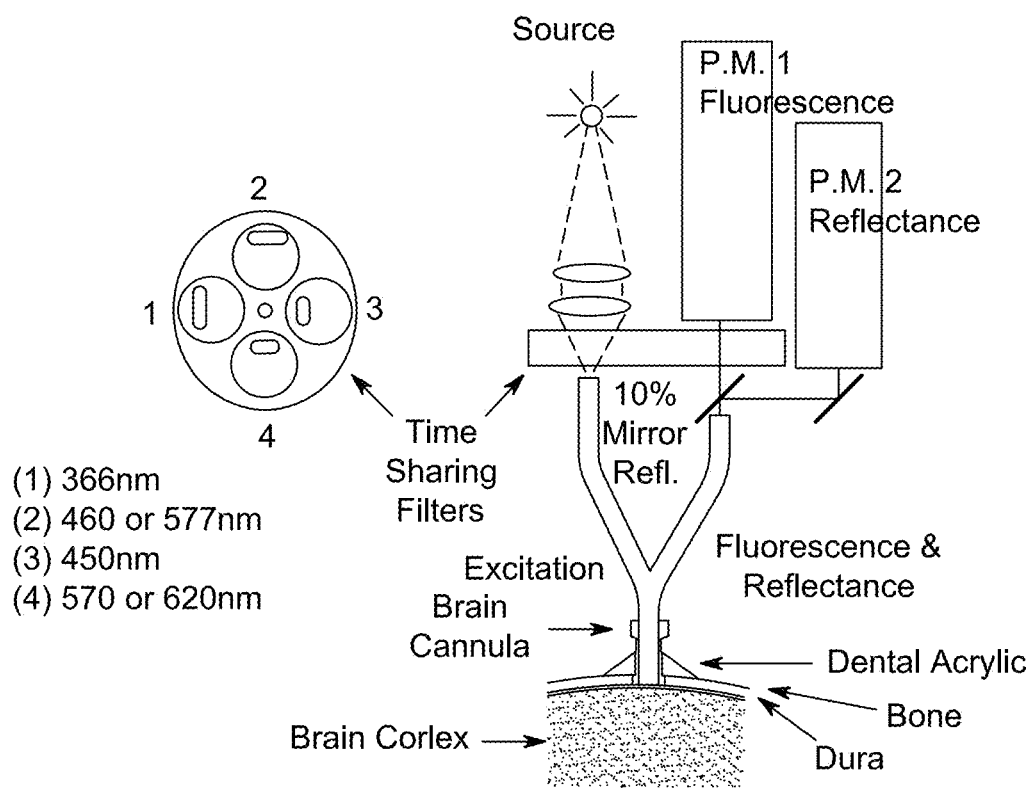
Figure 9E:
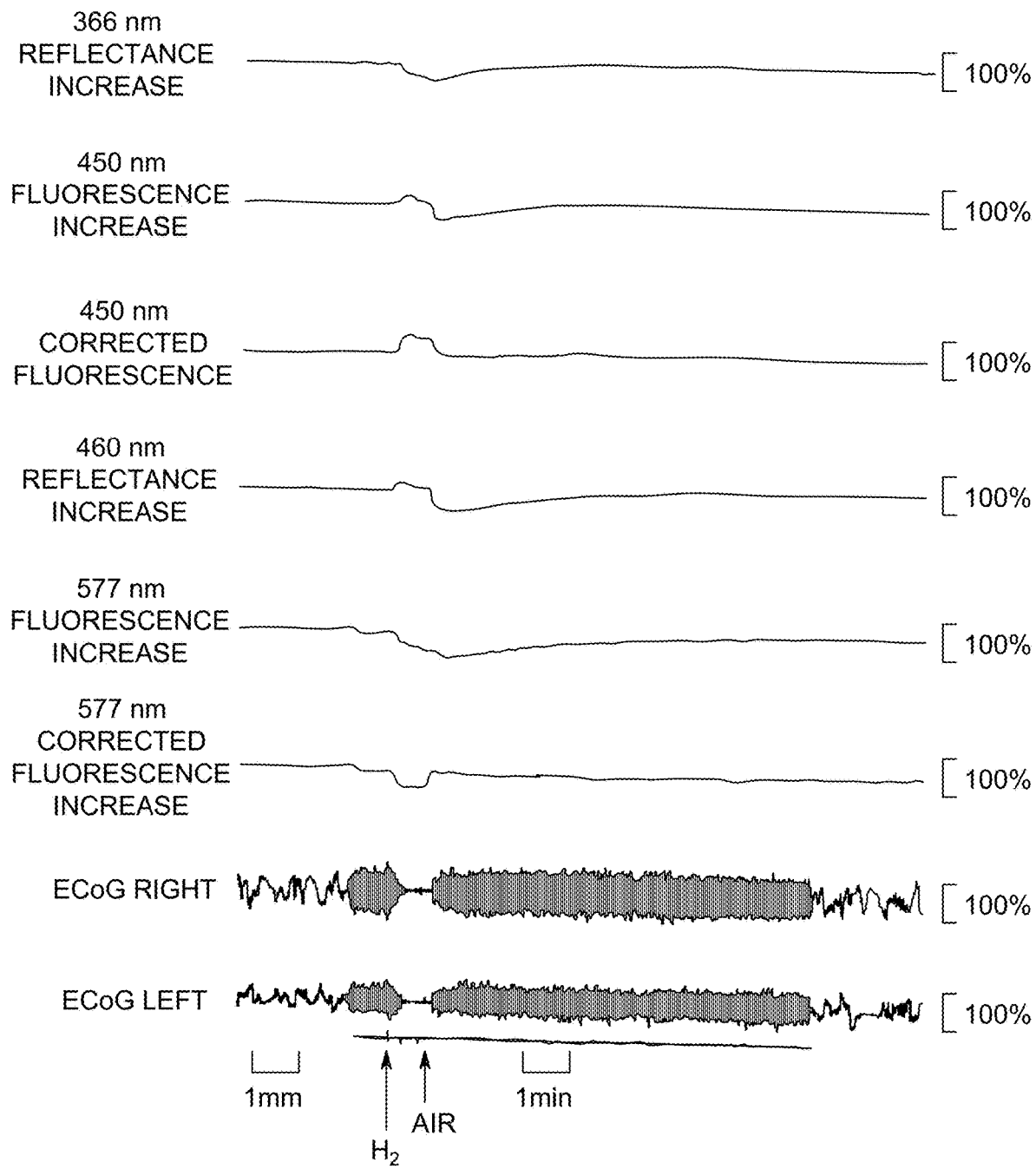

Referring to FIGS. 8E, 9D, and 9E, a second model may enable the measurement of the mitochondrial NADH and Flavo proteins in two dimensional configurations. This device will provide a map of the redox state of the tissue. Those two devices will be used only in monitoring tissues that are perfused with perfusion solutions and are tested under in vitro conditions. In order to measure the two fluorescence signals, newly developed LED light sources will be incorporated. A time-sharing device, shown in 9D, may be used to measure NADH and Fp from the surface of the brain exposed to the lack of oxygen. This device may enable the two-dimensional mapping of the NADH/Fp fluorescence in various samples grown in the in vitro tissue engineering process and in vivo.

Figure 8F:
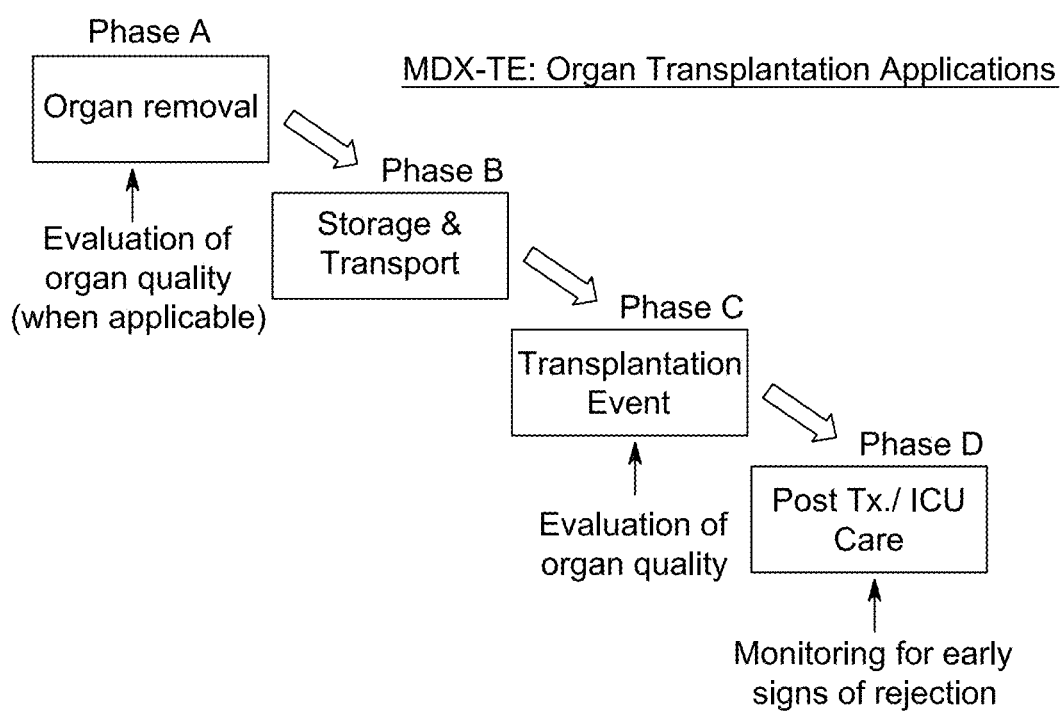
FIG. 8F is a time sequence of an organ transplantation.
Figure 10B:
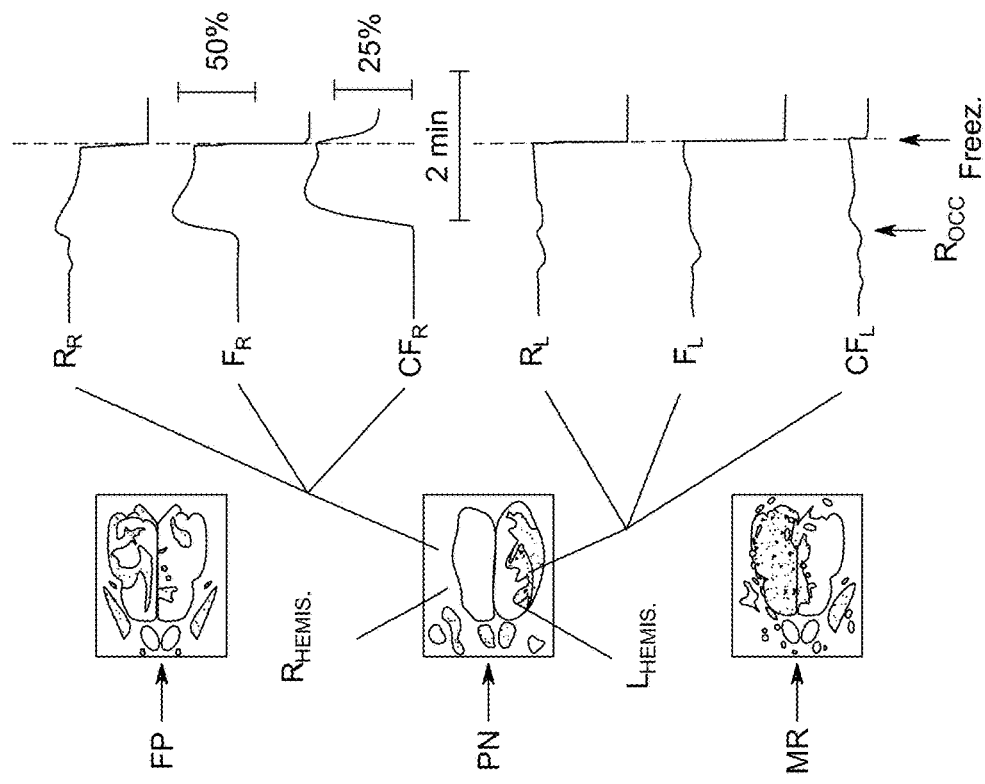
Figure 10A:
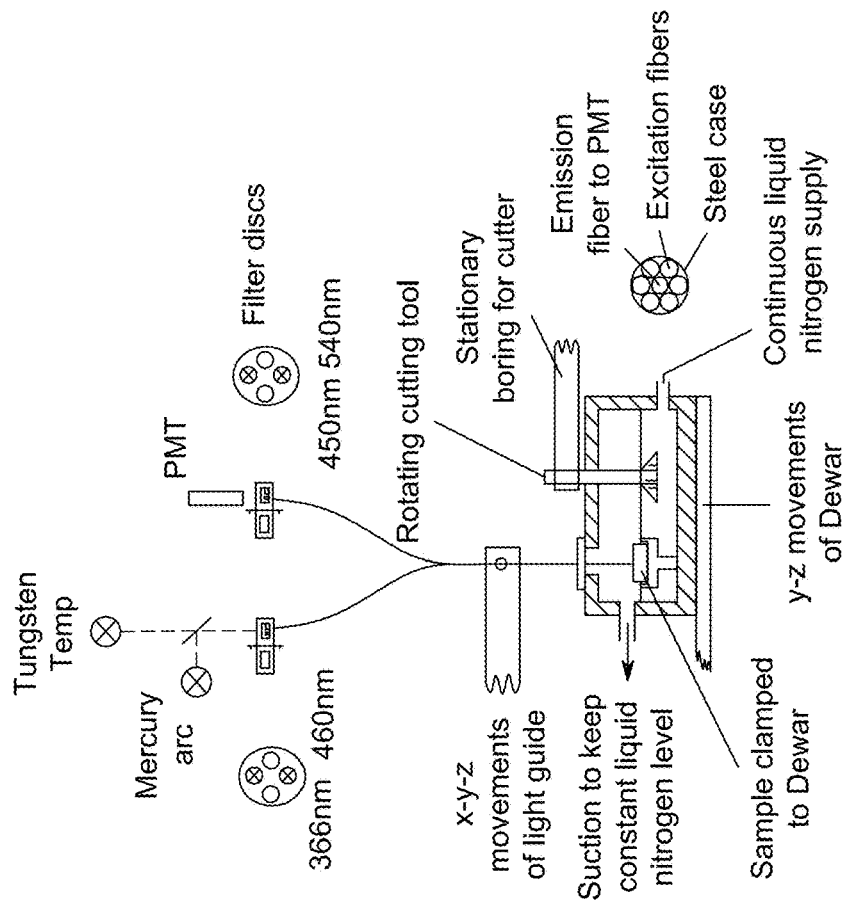

Referring to FIGS. 8F, 10A and 10B, a third model for in vivo studies of tissues and organs containing blood may include the monitoring of microcirculatory blood flow as well as hemoglobin oxygenation in addition to the monitoring of mitochondrial redox state described in the first model (NADH/Fp). This model may be used in testing the quality of an organ in the donor (phase A in FIG. 8F) and the transplanted organ in the patient during the post-operative period as seen in phase D in FIG. 8F. In this third model, all four of the tissue parameters (tissue blood flow, blood volume, hemoglobin oxygenation, and NADH/Fp fluorescence) may be measured from the same tissue volume by merging the excitation and emitted light to and from the tissue to the same fiber optic bundle. This may allow a more significant correlation between the four physiological parameters in analysis of the tissue metabolic score to be developed in this device. This third model may use multiparametric monitoring to ascertain mitochondrial function by monitoring microcirculatory blood flow and volume, and saturation level of the hemoglobin in the microcirculation. Each one of the parameters is measured by a different optical technique using different light sources but all the parameters may be measured from the same tissue volume.

Referring to FIG. 9A, the devices may have basic system subunits:
- a Light Source Unit that emits multiple wavelength light into a fiber optic probe that delivers the light to the tissue and collects returning light.
- The Detection Unit converts light signals into electrical signals.
- The Electronics and embedded compute system that controls the Light Source Unit and Detection Unit functions and performs data analysis.

These monitoring devices may be complimentary to multiparametric monitors typically used in operating rooms, intensive care units, and the like. Real time monitoring of mitochondrial function, metabolic state, and/or tissue metabolic score may provide a powerful tool in patient monitoring hospitalized in the operating rooms, intensive care units, and during post-operative care. The monitoring of a high-risk patient (due to it medical state or the complexity of the procedure) may started before the operation, during the surgical procedure and end up in the post-operative ICU stay. Since many patients in ICU care have a Foley catheter for urine collection, that catheter may be used for metabolic monitoring.

II.Q. Example 16: Monitor and Probes

Figures 10C, 10D:
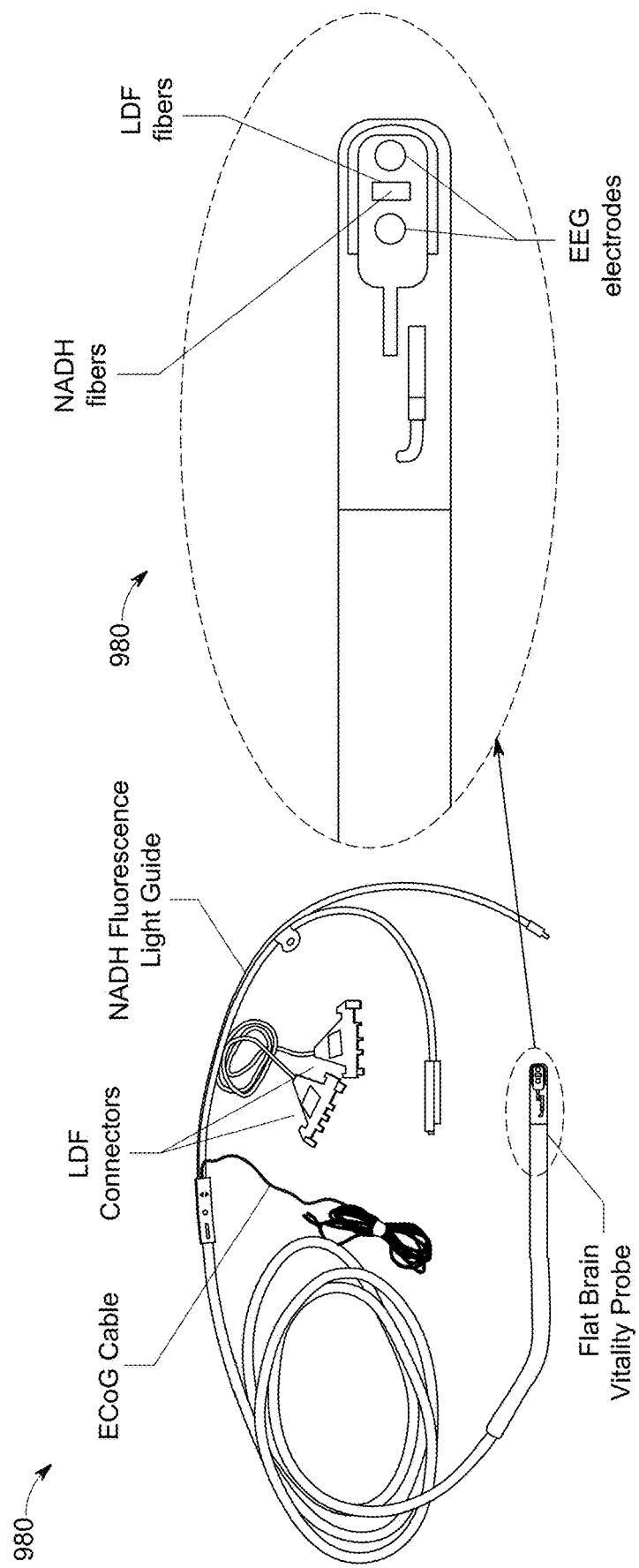

Referring to FIG. 10C shows a prototype of a flat probe 980 that may enable the monitoring of various parameters from the surface of the brain. This probe is located below the dura mater and is in good contact with the surface of the brain. In specific patients such as in the neurosurgical intensive care unit (ICU) it is recommended to monitor other brain functions in addition to the four parameters measured by the tissue metabolic score of section II.O. The idea is to combine a flat multi-probe sensor that will accommodate intracranial pressure sensor and two EEG electrodes as shown in FIG. 2C box A 120 and FIG. 2C box C 124, 126, 128. This multi probe is placed subdurally without creating any pressure on the brain tissue. The ICP (intracranial pressure) probe could be added to the same multi probe assembly.

III. Urethral Monitoring and Total Body Metabolic Score

III.A. A Multiparameter Catheter

Referring to FIGS. 10E, 10F, 10G, and FIG. 2F, in other cases, multiple tissue parameters may be measured via sensors in a urethral catheter. The vascularization around the urethra presents a mixture of capillaries, small and larger arterioles and arteries (over 0.5 mm or 1 mm in diameter), so that a given sensor will face vessels of varying size, so a given location or nearby locations can be used to measure both microcirculation parameters and macrocirculation parameters, without special care taken to "aim" the sensor. The sensors may be roughly collocated, or spread among two, three, or more clusters along the urethra. Four parameters that are especially desirable for calculating tissue metabolic score are NADH (either as UV absorbance or blue fluorescence), TBF (tissue blood flow), HbO2 (tissue oxyhemoglobin), and reflectance. Systemic hemodynamic parameters may be measured and calculated from data obtained nearby in the urethra using sensors, and photoplethysmography principles and technology, and conventional sensor technology, also integrated into the catheter. Some sensors may be implemented as a pair of fiber optic fibers, one fiber for illumination and one fiber to carry reflected or fluoresced light back to a detector. Each illumination fiber may carry an illumination wavelength appropriate to a physiological parameter to be measured. For example, the fiber to measure NADH may carry illumination light at 320-380 nm (ultraviolet), and the sensor at the device end of the sensor fiber may analyze for fluorescence at 420-480 nm. Other wavelengths and sensor technologies may be used to measure temperature, blood pressure, heart rate, cardiac cycle, blood oxygenation, and the like, and a paired sensor fiber may be used to collect reflected or fluoresced light to allow a detector to analyze the relevant parameter. An individual fiber may be time-division multiplexed, for example carrying one wavelength at one second and a different wavelength for the following five seconds. Other sensors may be electronic. Having systemic and microcirculation parameters co-located may allow various measurements to allow better comparisons and contrasts (correlations and isolations) between systemic and microcirculation parameters. Multiple sensors (either illumination/sensor fiber pairs or electronic) may be distributed over a section of the catheter to allow measurement of multiple parameters simultaneously. If a patient requires a urethral catheter anyway, it may be desirable to reduce the number of other wires to the patient by incorporating more of the sensors into the catheter.

Figures 10E, 10F:
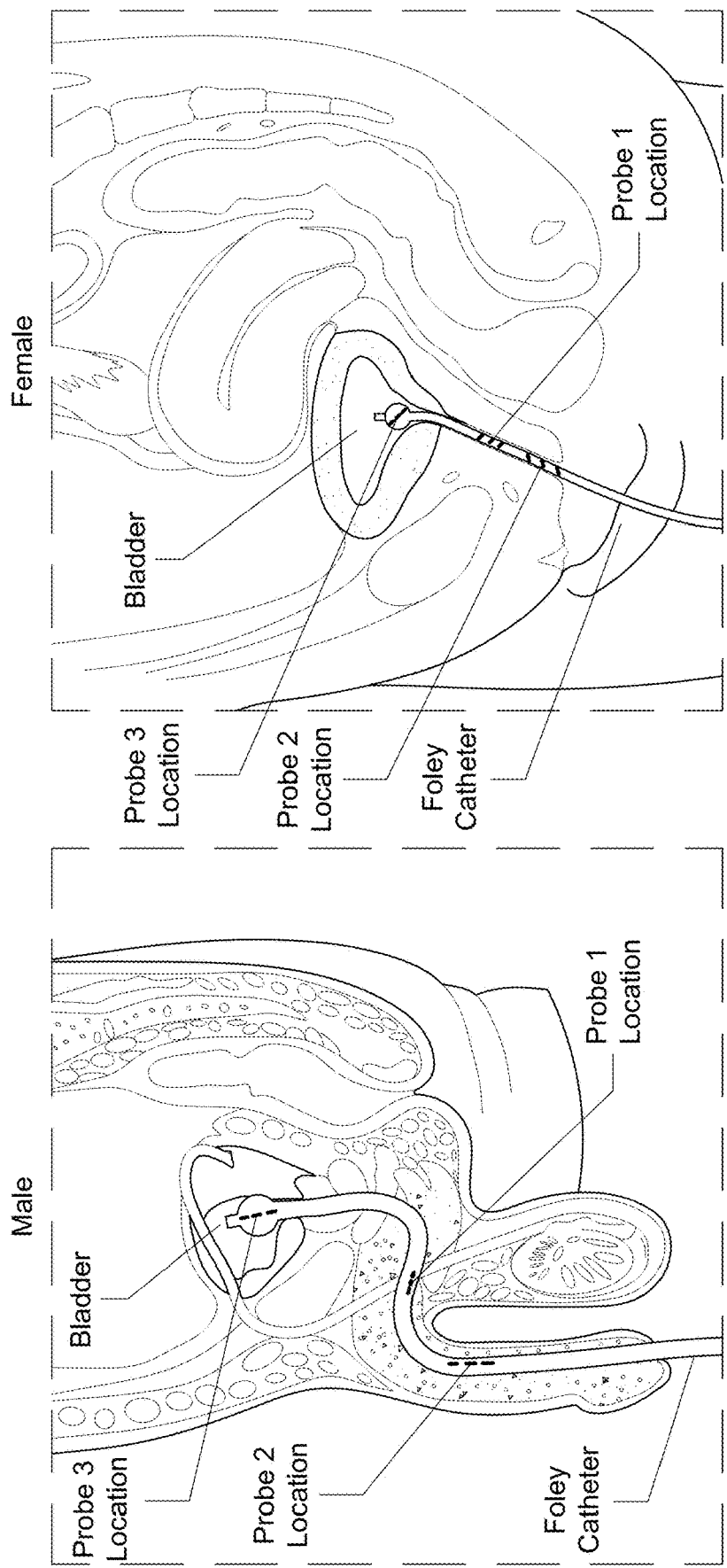
FIGS. 10E and 10F are views of a body partially cut away to show placement of monitoring probes.
Figure 10G:
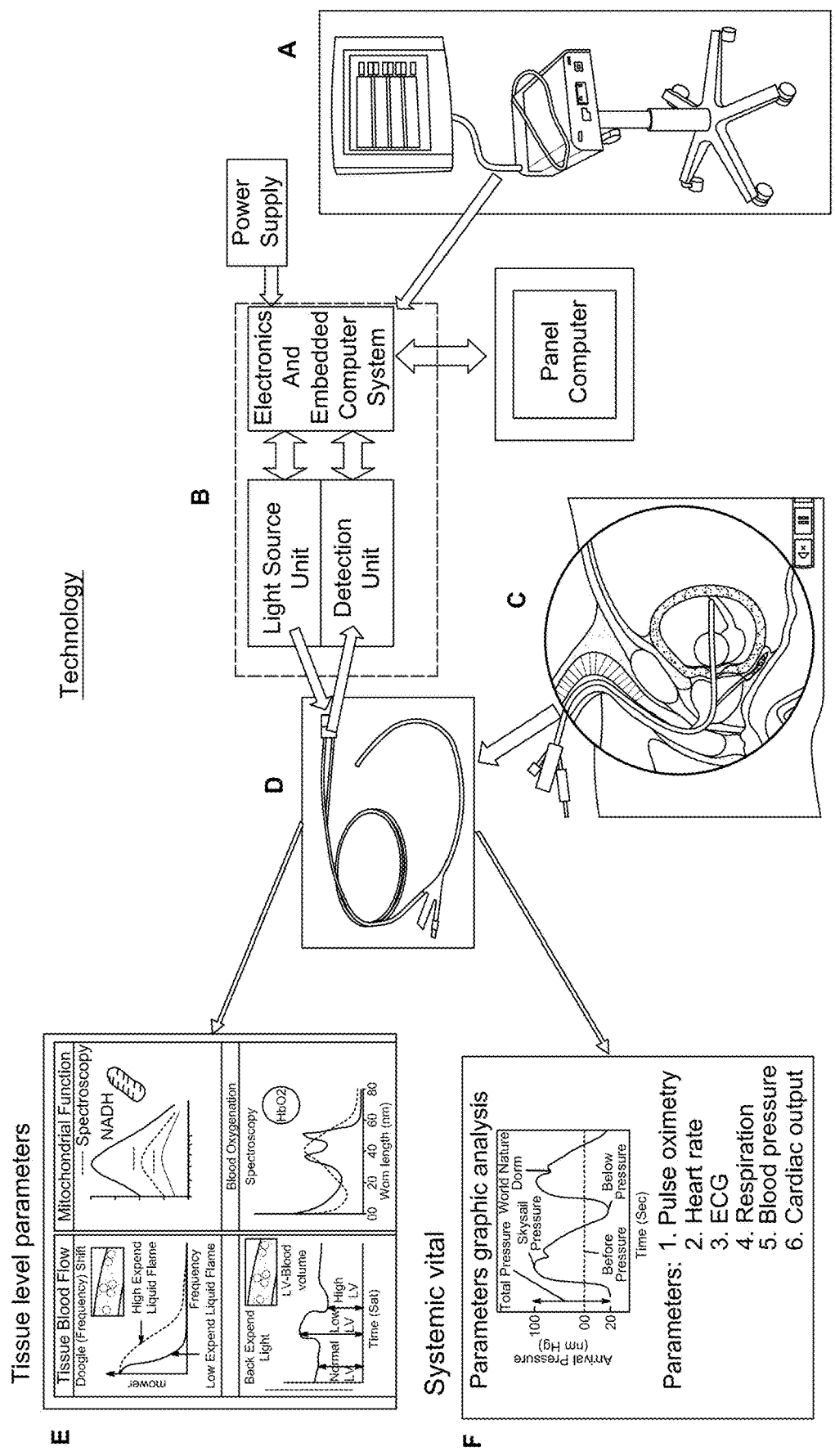

Referring to FIGS. 10E and 10F, the sensors may be distributed in three areas. One sensing area may measure the four parameters for mitochondria and microcirculation, a second sensing area may have sensors for systemic parameters (these may use photoplethysmography techniques or other conventional sensing technologies), and a third sensing area may have sensors for measuring properties of urine in the bladder (such as body core temperature).

Other probes suitable for multiparameter monitoring, including monitoring of NADH fluorescence, are described in U.S. Pat. No. 7,313,424, incorporated by reference.

III.B. A Multi-Parameter Total Body Metabolic Score

Referring again to FIG. 2F, the four parameters of the tissue metabolic score (from the left side parameters 150) may be combined with an evaluation of classic vital signs score (from the right side parameters 152) to form a total body metabolic score that helps in evaluation of the state of a patient. The tissue metabolic score may be measured at the urethra, to compute a $TMS_u$. Vital signs for a Systemic Vital Signs Score (SVSS) may be measured at the urethra (for example using photoplethysmography sensors), or via the patient's multiparametric monitoring system. Because of the circulatory properties of the tissues surrounding the urethra, a tissue metabolic score at the urethra may be interpreted to provide oxygen balance in the entire body, as discussed at several points above. If the patient is attached to multiple monitoring systems, a computation device may allow a user to select the source of information for the TMS score and SVSS score.

Two possible computations for a Total Body Metabolic Score, differing in where the vital signs are measured, are:

$$\text{Total Body Metabolic Score}_u = 0.8 \times TMS_u + 0.2 \times SVSS_u.$$

$$\text{Total Body Metabolic Score}_b = 0.8 \times TMS_u + 0.2 \times SVSS_b.$$

where $TMS_u$ (Tissue Metabolic Score at the urethra)=$0.1 \times TBF + 0.75 \times (200-NADH) + 0.1 \times HbO_2 + 0.05 \times (200-\text{Reflectance})$ $SVSS_u = 0.6 \times POHbO2 + 0.3 \times HR + 0.1 \times (200-\text{Core Temp})$ $SVSS_b = 0.6 \times POHbO_2 + 0.1 \times HR + 0.1 \times BP + 0.1 \times CO + 0.1 \times (200-\text{Core Temp})$ where
- $SVSS_u$=Systemic Vital Signs Score measured at the urethra
- $SVSS_b$=Systemic Vital Signs Score measured elsewhere in the body
- PO=Pulse Oximetry
- HR=Heart Rate
- BP=Blood Pressure
- CO=Cardiac Output All parameters are normalized to 100%.

For another example:

$$\text{Total Body Metabolic Score}_3 = 0.7 \times (0.1 \times TBF + 0.8 \times (200-NADH) + 0.1 \times HbO_2) + 0.3 \times (0.25 \times \text{temperature} + 0.25 \times \text{heart rate} + 0.25 \times \text{blood pressure} + 0.25 \times \text{cardiac cycle})$$

Another possible formula is:

$$\text{Total Body Metabolic Score}_4 = 0.8 \times (0.1 \times TBF + 0.75 \times (200-NADH) + 0.1 \times HbO_2 + 0.05 \times \text{Reflectance}) + 0.2 \times (0.2 \times \text{temperature} + 0.4 \times \text{heart rate} + 0.4 \times \text{blood pressure})$$

where the units of CBF and $HbO_2$ are normalized so that they vary from 0 to 100, and the units of NADH are normalized to run from 0 to 200, centered at 100 for normal. Another possible formula is $$\text{Total Body Metabolic Score}_5 = (1.0 - 0.1 \times (1.0 - TBF_{lagging})^2) \times (1.0 - 0.1 \times (1.0 - HbO_{2\ lagging})^2) \times (1.0 - 0.8 \times (1.0 - NADH)^2) \times (1.0 - 0.15 \times (\text{body temperature} - 37)^2) \times (1.0 - 0.4 \times (\text{heart rate} - 70)^2) \times (1.0 - 0.4 \times (\text{systolic blood pressure} - 112)^2)$$

where the $_{lagging}$ subscript indicates that parameter is measured over a recent time period (such as one minute), perhaps with recent measurements weighted more heavily than less recent measurements, and each of TBF, $HbO_2$ and NADH are normalized on the interval (0.0 to 2.0) with normoxia normalized to 1.0. Total Body Metabolic Score$_3$ has a value of 1 when all systems are at normal, and decreases as each parameter deviates from normal. The coefficients may be rebalanced as data and experience accumulates.

In each case, the Total Body Metabolic Score is calculated to provide an index of oxygen balance of the entire body, so that a decrease indicates deterioration in the oxygen supply to oxygen demand ratio, and increase indicates means improvement. The Total Body Metabolic Score may start to show changes before changes to the vital signs are apparent. A change in Total Body Metabolic Score over some period of time, for example, more than one minute, may be used to signal to a clinician that some change to treatment is indicated. For example, for an emergency room patient with high blood loss, the Total Body Metabolic Score may help the clinician to decide when to stop infusion of blood.

For example, in a patient undergoing a bypass operation, the TMS (tissue metabolic score for some tissue in the body) may start to decrease very early in the operation procedure, for example, at the beginning of the opening of the chest. The level of the TMS will stay very low during the entire operation and will start to recover to the pre-operation level at the end of the operation and the closure of the chest. During the period of the operation the patient is connected to the heart lung machine and therefore there is no real monitoring of the vital signs. The meaning of this situation is that the TMS will be the sole parameter that the clinician will be see and use. Once this patient is returned to the ICU for post-operative recovery, monitoring of the vital signs will be restarted and the systemic parameters will start to be calculated and contribute to the values of the Total Body Metabolic Score. Metabolic scores are generally relative, not absolute—the changes are more meaningful than the absolute number. For example, coefficients of the computation equation may be normalized before a procedure starts, so that the baseline TMS for the relevant organ is 100 and the Total Body Metabolic Score is also 100, before the procedure starts. During the procedure, the TMS may decline to 50. During initial recovery, the TMS may recover to 70. In the ICU, the vital signs score may be 100 as before the operation, but the calculated Total Body Metabolic Score may be somewhat higher, for example, 80, reflecting that better systemic vital signs relative to TMS. This may communicate to the clinician that the macrocirculation has recovered to normal and the microcirculation is still not healthy.

IV. Example 17: Big Data Implementations

As large numbers of patients are monitored, machine learning techniques may be used to analyze multiple data sets and to improve the diagnostic capacity of the tissue metabolic score. With monitoring of many patients, and recording of monitoring data, it may be possible to use machine learning, expert system, and other "big data" techniques to find correlations among various parameters that are particularly helpful in guiding diagnosis and treatment decisions.

For example, correlations between various parameters and outcomes may be discerned, in either designing a formula to incorporate parameters, or in setting coefficients for various possible formulae. Correlations among parameters monitored at the same organ, at different organs, correlations among parameters and systemic vital signs, etc. may reveal themselves to be predictive of patient outcomes. Curve-fitting techniques may be used, for example the features provided by Mathworks in MATLAB or NLINFIT, or the curve-fitting techniques provided in KaleidaGraph from Synergy Software, or the GNU Scientific Library.

V. Computer Implementation

Various processes described herein may be implemented by appropriately programmed general purpose computers, special purpose computers, and computing devices. Typically, a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in one or more computer programs, one or more scripts, or in other forms. The processing may be performed on one or more microprocessors, central processing units (CPUs), computing devices, microcontrollers, digital signal processors, or like devices or any combination thereof. Programs that implement the processing, and the data operated on, may be stored and transmitted using a variety of media. In some cases, hard-wired circuitry or custom hardware may be used in place of, or in combination with, some or all of the software instructions that can implement the processes. Algorithms other than those described may be used.

Programs and data may be stored in various media appropriate to the purpose, or a combination of heterogenous media that may be read and/or written by a computer, a processor or a like device. The media may include non-volatile media, volatile media, optical or magnetic media, dynamic random access memory (DRAM), static ram, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge or other memory technologies. Transmission media include coaxial cables, copper wire and fiber optics, including the wires that comprise a system bus coupled to the processor.

Databases may be implemented using database management systems or ad hoc memory organization schemes. Alternative database structures to those described may be readily employed. Databases may be stored locally or remotely from a device which accesses data in such a database.

In some cases, the processing may be performed in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices, such as those based on the Intel® Pentium® or Centrino™ processor, that are adapted to communicate with the computer. Any number and type of devices may be in communication with the computer.

A server computer or centralized authority may or may not be necessary or desirable. In various cases, the network may or may not include a central authority device. Various processing functions may be performed on a central authority server, one of several distributed servers, or other distributed devices.

For the convenience of the reader, the above description has focused on a representative sample of all possible embodiments, a sample that teaches the principles of the invention and conveys the best mode contemplated for carrying it out. Throughout this application and its associated file history, when the term "invention" is used, it refers to the entire collection of ideas and principles described; in contrast, the formal definition of the exclusive protected property right is set forth in the claims, which exclusively control. The description has not attempted to exhaustively enumerate all possible variations. Other undescribed variations or modifications may be possible. Where multiple alternative embodiments are described, in many cases it will be possible to combine elements of different embodiments, or to combine elements of the embodiments described here with other modifications or variations that are not expressly described. A list of items does not imply that any or all of the items are mutually exclusive, nor that any or all of the items are comprehensive of any category, unless expressly specified otherwise. In many cases, one feature or group of features may be used separately from the entire apparatus or methods described. Many of those undescribed variations, modifications and variations are within the literal scope of the following claims, and others are equivalent.

The invention claimed is:

1. A method comprising the steps of:
emplacing in an organ of interest in a patient, a set of sensors designed to monitor parameters of the organ of interest, including at least nicotinamide adenine dinucleotide ($NADH_I$) level and at least one parameter from among the group consisting of tissue blood flow ($BF_I$), blood hemoglobin ($HbO_{2I}$), and tissue reflectance ($TR_I$), and substantially continuously, computing a vitality index of the organ of interest based at least in part on the parameters monitored by the sensors at the organ of interest;
monitoring parameters at another tissue of the patient continuously for a systemic reference, including at least NADH ($NADH_S$) level and at least two parameters from among the group consisting of blood flow ($BF_S$), blood hemoglobin ($HbO_{2S}$), and tissue reflectance ($TR_S$), and substantially continuously, computing a systemic vitality index from the monitored systemic parameters;
monitoring for a divergence in the temporal trend of the vitality index of the organ of interest from the systemic reference vitality index; and
based on the detection of the divergence, raising an alarm to a physician to warn the physician of a change in the patient's condition.

2. The method of claim 1, wherein:
the organ of interest is the urethra;
the sensors are mounted in the wall of a urethral catheter.

3. The method of claim 1, wherein:
the organ of interest is an organ recently transplanted into the patient.

4. The method of claim 1, wherein:
the sensors for the organ of interest include at least three of four of sensors from the group consisting of nicotinamide adenine dinucleotide ($NADH_I$), tissue blood flow ($BF_I$), blood hemoglobin ($HbO_{2I}$), and tissue reflectance ($TR_I$).

5. The method of claim 1, further comprising the steps of:
monitoring at least two vital signs drawn from the group consisting of pulse rate, temperature, respiration rate, blood pressure, blood level of $CO_2$, and blood pH;
computing a vital signs index based on the monitored vital signs;
monitoring for a divergence in the temporal trend of the vitality index of the organ of interest from the vital signs index; and
based on the detection of the divergence, raising an alarm to a physician to warn the physician of a change in the patient's condition.

6. The method of claim 1, further comprising the step of:
computing a vitality index normalized to a steady-state observation of normal function for the specific patient.

7. A method comprising the steps of:
continuously monitoring parameters of a first tissue in a patient via a first set of sensors designed to monitor a first set of parameters of the first tissue, the tissue being a tissue from which blood is redistributed to conserve blood flow to vital organs during homeostasis, the first monitored parameters including at least nicotinamide adenine dinucleotide ($NADH_f$) level and at least one parameter from among the group consisting of tissue blood flow ($BF_f$), blood hemoglobin ($HbO_{2f}$), and tissue reflectance ($TR_f$);

substantially continuously, computing a first vitality index of the first tissue based at least in part on the first monitored parameters by the first sensors at the first tissue;

concurrently with monitoring the parameters of the first tissue, continuously monitoring a second set of parameters of a second tissue of the patient, the second tissue being different than the first tissue, the second monitored parameters of the second tissue including at least NADH ($NADH_S$) level and at least two parameters from among the group consisting of blood flow ($BF_S$), blood hemoglobin ($HbO_{2S}$), and tissue reflectance ($TR_S$);

substantially continuously, computing a second vitality index from the second monitored parameters of the second tissue;

monitoring for a divergence in the temporal trend of the first vitality index from the second vitality index; and based at least in part on the detection of the divergence, raising an alarm to a physician to warn the physician of a change in the patient's condition.

8. The method of claim 7, wherein:
the first tissue is a point in the gastrointestinal tract.

9. The method of claim 7, wherein:
the first tissue is the urethra; and
the sensors are mounted in the wall of a urethral catheter.

10. The method of claim 7, wherein:
the first tissue is an organ recently transplanted into the patient.

11. The method of claim 7, wherein:
the first set of sensors include at least three of four of sensors from the group consisting of nicotinamide adenine dinucleotide ($NADH_f$), tissue blood flow ($BF_f$), blood hemoglobin ($HbO_{2f}$), and tissue reflectance ($TR_f$).

12. The method of claim 7, wherein:
the first set of sensors include at least sensors for nicotinamide adenine dinucleotide ($NADH_f$), tissue blood flow ($BF_f$), blood hemoglobin ($HbO_{2f}$), and tissue reflectance ($TR_f$).

13. The method of claim 7, further comprising the steps of:
monitoring at least two vital signs drawn from the group consisting of pulse rate, temperature, respiration rate, blood pressure, blood level of $CO_2$, and blood pH;
computing a vital signs index based on the monitored vital signs;
monitoring for a divergence in the temporal trend of at least one of the first and second vitality indices from the vital signs index; and
based on the detection of the divergence, raising an alarm to a physician to warn the physician of a change in the patient's condition.

14. The method of claim 7, in which the second set of parameters are monitored at a highly-conserved tissue.

15. The method of claim 7, in which the second set of parameters are monitored at the brain of the patient.

16. The method of claim 7, in which the second set of parameters are monitored at the heart of the patient.

17. The method of claim 7, in which computation of at least one of the first and second vitality indices is normalized to a steady-state observation of normal function for the specific patient of claim 7.

18. The method of claim 7, in which computation of at least one of the first and second vitality indices is normalized across data obtained from many patients' sensors and accumulated in a database.

19. The method of claim 7, in which the computation of divergence of the first tissue vitality index from the second vitality index is calibrated across data obtained from many patients' sensors and accumulated in a database.

* * * * *